(12) United States Patent
Geall et al.

(10) Patent No.: US 11,759,422 B2
(45) Date of Patent: *Sep. 19, 2023

(54) PEGYLATED LIPOSOMES FOR DELIVERY OF IMMUNOGEN-ENCODING RNA

(71) Applicant: GLAXOSMITHKLINE BIOLOGICALS SA, Rixensart (BE)

(72) Inventors: Andrew Geall, Littleton, MA (US); Ayush Verma, Morrisville, NC (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 122 days.

This patent is subject to a terminal disclaimer.

(21) Appl. No.: 16/837,115

(22) Filed: Apr. 1, 2020

(65) Prior Publication Data

US 2020/0230058 A1    Jul. 23, 2020

Related U.S. Application Data

(63) Continuation of application No. 13/819,077, filed as application No. PCT/US2011/050095 on Aug. 31, 2011, now abandoned.

(Continued)

(51) Int. Cl.
*A61K 9/127*    (2006.01)
*A61K 9/00*    (2006.01)
(Continued)

(52) U.S. Cl.
CPC ............ *A61K 9/127* (2013.01); *A61K 9/0019* (2013.01); *A61K 9/10* (2013.01); *A61K 9/1271* (2013.01);
(Continued)

(58) Field of Classification Search
CPC ........ A61K 9/127; A61K 9/0019; A61K 9/10; A61K 9/1271; A61K 39/12; A61K 39/155;
(Continued)

(56) References Cited

U.S. PATENT DOCUMENTS 5,013,556 A    5/1991    Woodle et al.
5,279,833 A    1/1994    Rose
(Continued)

FOREIGN PATENT DOCUMENTS

BR    112013004879    4/2018
BR    112012001666-0    9/2019
(Continued)

OTHER PUBLICATIONS

Mockey, M. et al., "mRNA-based Cancer Vaccine: Prevention of B16 Melanoma Progression and Metastatis By Systemic Injection of MART1 mRNA HIstidylated Lipopolyplexes", Cancer Gene Therap. 2007; pp. 802-814; vol. 14.
(Continued)

*Primary Examiner* — Gollamudi S Kishore

(57) ABSTRACT

Nucleic acid immunisation is achieved by delivering RNA encapsulated within a PEGylated liposome. The RNA encodes an immunogen of interest. The PEG has an average molecular mass of between 1 kDa and 3 kDa. Thus the invention provides a liposome having a lipid bilayer encapsulating an aqueous core, wherein: (i) the lipid bilayer comprises at least one lipid which includes a polyethylene glycol moiety, such that polyethylene glycol is present on the liposome's exterior, wherein the average molecular mass of the polyethylene glycol is between 1 kDa and 3 kDa; and (ii) the aqueous core includes a RNA which encodes an immunogen. These liposomes are suitable for in vivo delivery of the RNA to a vertebrate cell and so they are useful as (Continued)

components in pharmaceutical compositions for immunising subjects against various diseases.

25 Claims, 12 Drawing Sheets

Related U.S. Application Data

(60) Provisional application No. 61/378,826, filed on Aug. 31, 2010.

(51) Int. Cl.
| | | |
|---|---|---|
| *A61K 39/39* | (2006.01) | |
| *A61K 9/10* | (2006.01) | |
| *A61K 39/155* | (2006.01) | |
| *C12N 15/88* | (2006.01) | |
| *A61K 39/12* | (2006.01) | |
| *A61K 39/00* | (2006.01) | |

(52) U.S. Cl.
CPC ............ *A61K 39/12* (2013.01); *A61K 39/155* (2013.01); *A61K 39/39* (2013.01); *C12N 15/88* (2013.01); *A61K 2039/53* (2013.01); *A61K 2039/55505* (2013.01); *A61K 2039/55555* (2013.01); *C12N 2710/16134* (2013.01); *C12N 2760/18534* (2013.01); *C12N 2770/36143* (2013.01); *C12N 2770/36171* (2013.01)

(58) Field of Classification Search
CPC ................ A61K 39/39; A61K 2039/53; A61K 2039/55505; A61K 2039/55555; C12N 15/88; C12N 2710/16134; C12N 2760/18534; C12N 2770/36143; C12N 2770/36171; A61P 31/00; A61P 31/10; A61P 31/12; A61P 33/00; A61P 37/04
See application file for complete search history.

(56) References Cited

U.S. PATENT DOCUMENTS

| | | | |
|---|---|---|---|
| 5,459,127 A | 10/1995 | Felgner et al. | |
| 5,474,914 A | 12/1995 | Spaete | |
| 5,750,390 A | 5/1998 | Thompson et al. | |
| 5,814,482 A | 9/1998 | Dubensky, Jr. et al. | |
| 5,843,723 A | 12/1998 | Dubensky, Jr. | |
| 5,885,613 A | 3/1999 | Holland | |
| 5,965,434 A | 10/1999 | Wolff et al. | |
| 5,972,704 A | 10/1999 | Draper et al. | |
| 6,009,406 A | 12/1999 | Nick | |
| 6,015,686 A | 1/2000 | Dubensky et al. | |
| 6,048,546 A | 4/2000 | Sasaki et al. | |
| 6,060,308 A | 5/2000 | Parrington | |
| 6,090,406 A | 7/2000 | Popescu et al. | |
| 6,156,558 A | 12/2000 | Johnston et al. | |
| 6,395,302 B1 | 5/2002 | Hennink et al. | |
| 6,432,925 B1 | 8/2002 | Hoon et al. | |
| 6,602,705 B1 | 8/2003 | Barnett et al. | |
| 6,610,321 B2 | 8/2003 | Huang et al. | |
| 6,790,449 B2 | 9/2004 | Collins | |
| 6,815,432 B2 | 11/2004 | Wheeler et al. | |
| 6,858,225 B2 | 2/2005 | Semple et al. | |
| 6,890,554 B2 | 5/2005 | Jessee et al. | |
| 7,250,404 B2 | 7/2007 | Feigner et al. | |
| 7,303,881 B2 | 12/2007 | Huang et al. | |
| 7,384,923 B2 | 6/2008 | Gregoriadis | |
| 7,422,902 B1 | 9/2008 | Wheeler et al. | |
| 7,442,381 B2 | 10/2008 | Smith et al. | |
| 7,557,200 B2 | 7/2009 | Wu et al. | |
| 7,604,803 B2 | 10/2009 | Bacon et al. | |
| 7,691,405 B2 | 4/2010 | Chen et al. | |
| 7,745,651 B2 | 6/2010 | Heyes et al. | |
| 7,799,565 B2 | 9/2010 | Maclachlan et al. | |
| 7,811,812 B2 | 10/2010 | Dubensky et al. | |
| 7,862,829 B2 | 1/2011 | Johnston et al. | |
| 7,977,091 B2 | 7/2011 | Dubensky et al. | |
| 8,058,069 B2 | 11/2011 | Yaworski et al. | |
| 8,338,583 B2 | 12/2012 | Michaeli | |
| 8,877,206 B2 | 11/2014 | Chen et al. | |
| 9,254,265 B2 | 2/2016 | Geall et al. | |
| 9,504,651 B2 | 11/2016 | Maclachlan et al. | |
| 9,770,463 B2 | 9/2017 | Geall et al. | |
| 9,801,897 B2 | 10/2017 | Geall et al. | |
| 9,801,987 B2 | 10/2017 | Farnan et al. | |
| 10,188,748 B2 | 1/2019 | Mulbe et al. | |
| 10,487,332 B2 | 11/2019 | Geall | |
| 10,532,067 B2 | 1/2020 | Geall et al. | |
| 10,906,867 B2 | 2/2021 | Brito et al. | |
| 11,026,964 B2 | 6/2021 | Geall et al. | |
| 11,058,762 B2 | 7/2021 | Geall et al. | |
| 11,078,237 B2 | 8/2021 | Franti et al. | |
| 11,291,635 B2 | 4/2022 | Geall et al. | |
| 11,291,682 B2 | 4/2022 | Geall et al. | |
| 11,324,770 B2 | 5/2022 | Geall et al. | |
| 2003/0091591 A1 | 5/2003 | Xiong et al. | |
| 2003/0096397 A1 | 5/2003 | Schlesinger | |
| 2003/0124134 A1 | 7/2003 | Edwards, Jr. et al. | |
| 2003/0138453 A1 | 7/2003 | O'Hagan et al. | |
| 2003/0203865 A1 | 10/2003 | Harvie | |
| 2003/0212022 A1 | 11/2003 | Vogel et al. | |
| 2003/0232058 A1 | 12/2003 | Dubensky, Jr. | |
| 2004/0142025 A1 | 7/2004 | Maclachlan et al. | |
| 2004/0208848 A1 | 10/2004 | Smith et al. | |
| 2004/0228842 A1 | 11/2004 | Lu et al. | |
| 2005/0032730 A1 | 2/2005 | Von Der Mulbe et al. | |
| 2005/0042230 A1 | 2/2005 | Anderson et al. | |
| 2005/0064026 A1 | 3/2005 | Garidel et al. | |
| 2005/0064595 A1 | 3/2005 | Maclachlan et al. | |
| 2005/0118566 A1 | 6/2005 | Escriou et al. | |
| 2005/0266550 A1 | 12/2005 | Rayner et al. | |
| 2006/0002991 A1 | 1/2006 | Essler et al. | |
| 2006/0051405 A1 | 3/2006 | MacLachlan et al. | |
| 2006/0063732 A1 | 3/2006 | Vogel et al. | |
| 2006/0083780 A1 | 4/2006 | Heyes et al. | |
| 2006/0177819 A1 | 8/2006 | Smith et al. | |
| 2006/0240554 A1 | 10/2006 | Chen et al. | |
| 2006/0251620 A1 | 11/2006 | Ivanova | |
| 2007/0014805 A1 | 1/2007 | Dalencon et al. | |
| 2007/0118094 A1 | 5/2007 | Bingham et al. | |
| 2007/0207526 A1 | 9/2007 | Coit | |
| 2008/0057080 A1 | 3/2008 | Luke et al. | |
| 2008/0085870 A1 | 4/2008 | Hermanson et al. | |
| 2008/0187545 A1 | 8/2008 | Shenk et al. | |
| 2008/0249046 A1 | 10/2008 | Maclachlan et al. | |
| 2008/0260698 A1 | 10/2008 | Weaver | |
| 2008/0311158 A1 | 12/2008 | Merola | |
| 2009/0068221 A1 | 3/2009 | Morrison | |
| 2009/0075384 A1 | 3/2009 | Kamrud | |
| 2009/0104226 A1 | 4/2009 | Perri et al. | |
| 2009/0143323 A1* | 6/2009 | Bavari | A61P 31/14 514/44 R |
| 2010/0040650 A1 | 2/2010 | Crowe et al. | |
| 2010/0092481 A1 | 4/2010 | Lanzavecchia | |
| 2010/0173980 A1 | 7/2010 | Vaillant et al. | |
| 2010/0196492 A1 | 8/2010 | Green et al. | |
| 2010/0285112 A1 | 11/2010 | Novobrantseva | |
| 2010/0324120 A1 | 12/2010 | Chen | |
| 2011/0305727 A1 | 1/2011 | Swanson | |
| 2011/0053893 A1 | 3/2011 | Wu et al. | |
| 2011/0070260 A1 | 3/2011 | Baric et al. | |
| 2011/0076335 A1 | 3/2011 | Yaworski et al. | |
| 2011/0117125 A1 | 5/2011 | Hope et al. | |
| 2011/0200582 A1 | 8/2011 | Baryza | |
| 2011/0200667 A1 | 8/2011 | Contreras et al. | |
| 2011/0229969 A1 | 9/2011 | Sandig et al. | |
| 2011/0300205 A1 | 12/2011 | Geall | |
| 2012/0030901 A1 | 2/2012 | Manninen et al. | |
| 2012/0100207 A1 | 4/2012 | Motokui et al. | |
| 2012/0156251 A1 | 6/2012 | Brito et al. | |
| 2012/0177677 A1 | 7/2012 | Carmon | |
| 2012/0195936 A1 | 8/2012 | Carten et al. | |
| 2012/0237546 A1 | 9/2012 | Singh et al. | |

(56) References Cited

U.S. PATENT DOCUMENTS

| | | |
|---|---|---|
| 2012/0251618 A1 | 10/2012 | Schrum |
| 2013/0101609 A1 | 4/2013 | O'Hagan et al. |
| 2013/0149375 A1 | 6/2013 | Geall |
| 2013/0164289 A1 | 6/2013 | McVoy et al. |
| 2013/0171185 A1 | 7/2013 | Settembre et al. |
| 2013/0171241 A1 | 7/2013 | Geall et al. |
| 2013/0177639 A1 | 7/2013 | Geall et al. |
| 2013/0177640 A1 | 7/2013 | Geall et al. |
| 2013/0183355 A1 | 7/2013 | Jain et al. |
| 2013/0189351 A1 | 7/2013 | Geall |
| 2013/0195968 A1 | 8/2013 | Geall |
| 2013/0195969 A1 | 8/2013 | Geall |
| 2013/0202684 A1 | 8/2013 | Geall |
| 2013/0225409 A1 | 8/2013 | Allen et al. |
| 2013/0245105 A1 | 9/2013 | De Fougerolles et al. |
| 2013/0295043 A1 | 11/2013 | Kallen |
| 2014/0023673 A1 | 1/2014 | Weiner |
| 2014/0030292 A1 | 1/2014 | Franti et al. |
| 2014/0044751 A1 | 2/2014 | Dormitzer |
| 2014/0141070 A1 | 5/2014 | Geall |
| 2014/0193484 A1 | 7/2014 | Bertholet Girardin et al. |
| 2014/0212498 A1 | 7/2014 | Brito et al. |
| 2014/0220083 A1 | 8/2014 | Brito et al. |
| 2014/0227346 A1 | 8/2014 | Geall et al. |
| 2014/0242152 A1 | 8/2014 | Geall et al. |
| 2014/0248314 A1 | 9/2014 | Swanson et al. |
| 2014/0255472 A1 | 9/2014 | Geall |
| 2014/0271829 A1 | 9/2014 | Lilja et al. |
| 2014/0275227 A1 | 9/2014 | Hoge et al. |
| 2014/0303232 A1 | 10/2014 | Baryza et al. |
| 2014/0348863 A1 | 11/2014 | Bianchi et al. |
| 2015/0017251 A1 | 1/2015 | Malvala et al. |
| 2016/0024157 A1 | 1/2016 | Masignani et al. |
| 2016/0129105 A1 | 5/2016 | Mülbe et al. |
| 2018/0094033 A1 | 4/2018 | Telford et al. |
| 2019/0343862 A1 | 11/2019 | Geall |
| 2020/0048636 A1 | 2/2020 | Geall |
| 2020/0069793 A1 | 3/2020 | Ciaramella |
| 2020/0113830 A1 | 4/2020 | Geall et al. |
| 2020/0113831 A1 | 4/2020 | Geall et al. |
| 2020/0230058 A1 | 7/2020 | Geall et al. |
| 2020/0323896 A1 | 10/2020 | Geall |
| 2021/0290755 A1 | 8/2021 | Geall et al. |
| 2021/0268013 A1 | 9/2021 | Geall et al. |
| 2022/0054525 A1 | 2/2022 | Geall et al. |
| 2022/0056449 A1 | 2/2022 | Geall |
| 2022/0119455 A1 | 4/2022 | Franti et al. |
| 2022/0192997 A1 | 6/2022 | Geall et al. |
| 2022/0213149 A1 | 7/2022 | Franti et al. |

FOREIGN PATENT DOCUMENTS

| | | |
|---|---|---|
| EP | 0786522 | 7/1997 |
| EP | 1083232 | 3/2001 |
| EP | 0880360 | 10/2002 |
| EP | 1392341 | 3/2004 |
| EP | 1637144 | 3/2006 |
| EP | 1764089 | 3/2007 |
| EP | 2338478 | 6/2011 |
| EP | 2510099 | 10/2012 |
| EP | 2578685 | 4/2013 |
| EP | 2791160 | 10/2014 |
| EP | 2590626 | 10/2015 |
| EP | 2591114 | 6/2016 |
| EP | 2590676 | 8/2016 |
| EP | 3336082 | 6/2018 |
| EP | 2750707 | 10/2018 |
| EP | 3318248 | 4/2019 |
| EP | 3492109 | 6/2019 |
| EP | 2591103 | 8/2019 |
| EP | 3611266 | 2/2020 |
| EP | 3682905 | 7/2020 |
| EP | 2729126 | 12/2020 |
| JP | 2000505802 | 5/2000 |
| JP | 2001514857 | 9/2001 |
| JP | 2007112768 | 5/2007 |
| JP | 2007521247 | 8/2007 |
| JP | 2008501729 | 1/2008 |
| JP | 2009510097 | 3/2009 |
| JP | 2009539845 | 11/2009 |
| JP | 2010025644 | 2/2010 |
| JP | 2010528591 | 8/2010 |
| JP | 2011504802 | 2/2011 |
| WO | 89/00812 A1 | 2/1989 |
| WO | WO9011092 | 10/1990 |
| WO | WO9219752 | 11/1992 |
| WO | WO1993024640 | 12/1993 |
| WO | WO9527721 | 10/1995 |
| WO | 96/08235 A1 | 3/1996 |
| WO | WO9617072 | 6/1996 |
| WO | WO9728818 | 8/1997 |
| WO | WO1997030170 | 8/1997 |
| WO | WO1998010748 | 3/1998 |
| WO | WO1998051278 | 11/1998 |
| WO | WO1999011808 | 3/1999 |
| WO | WO9928487 | 6/1999 |
| WO | WO9930733 | 6/1999 |
| WO | WO1999052503 | 10/1999 |
| WO | WO9955310 | 11/1999 |
| WO | WO0003683 | 1/2000 |
| WO | WO2000000617 | 1/2000 |
| WO | WO200129233 | 4/2001 |
| WO | WO200179253 | 10/2001 |
| WO | 01/93836 A3 | 12/2001 |
| WO | WO2002002606 | 1/2002 |
| WO | WO200209645 | 2/2002 |
| WO | WO2002026209 | 4/2002 |
| WO | WO2002034771 | 5/2002 |
| WO | WO2002061113 | 8/2002 |
| WO | WO02074920 | 9/2002 |
| WO | WO2002072027 | 9/2002 |
| WO | WO2002079239 | 10/2002 |
| WO | WO2002095023 | 11/2002 |
| WO | WO2002098443 | 12/2002 |
| WO | WO2003018054 | 3/2003 |
| WO | WO2003068190 | 8/2003 |
| WO | WO2004076645 | 9/2004 |
| WO | WO2004098509 | 11/2004 |
| WO | WO2005002619 | 1/2005 |
| WO | WO2005007689 | 1/2005 |
| WO | WO2005032582 | 4/2005 |
| WO | WO2005046621 | 5/2005 |
| WO | WO2005060934 | 7/2005 |
| WO | WO2005111066 | 11/2005 |
| WO | 2005/113782 A1 | 12/2005 |
| WO | 2005/121348 A1 | 12/2005 |
| WO | 2005120152 A2 | 12/2005 |
| WO | WO2005113781 | 12/2005 |
| WO | WO2006053646 | 5/2006 |
| WO | WO2006061643 | 6/2006 |
| WO | WO2006078294 | 7/2006 |
| WO | WO2006089264 | 8/2006 |
| WO | WO2006091517 | 8/2006 |
| WO | WO2006092607 | 9/2006 |
| WO | WO2006094756 | 9/2006 |
| WO | WO2006110413 | 10/2006 |
| WO | WO2006138004 | 12/2006 |
| WO | 2007014754 A1 | 2/2007 |
| WO | WO2007024708 | 3/2007 |
| WO | 2007/047749 A1 | 4/2007 |
| WO | WO2007036366 | 4/2007 |
| WO | WO2007041270 | 4/2007 |
| WO | WO2007049155 | 5/2007 |
| WO | WO2007107304 | 9/2007 |
| WO | WO2007146024 | 12/2007 |
| WO | WO2007149518 | 12/2007 |
| WO | WO2008020330 | 2/2008 |
| WO | WO2008033966 | 3/2008 |
| WO | WO2008051245 | 5/2008 |
| WO | WO2008083949 | 7/2008 |
| WO | 2008/103276 A2 | 8/2008 |
| WO | 2008103276 A2 | 8/2008 |
| WO | WO2008137758 | 11/2008 |
| WO | WO2008148068 | 12/2008 |

(56) References Cited

FOREIGN PATENT DOCUMENTS

| | | |
|---|---|---|
| WO | WO2008155141 | 12/2008 |
| WO | WO2009003975 | 1/2009 |
| WO | WO2009016515 | 2/2009 |
| WO | WO2009026328 | 2/2009 |
| WO | WO2009031043 | 3/2009 |
| WO | WO2009040443 | 4/2009 |
| WO | WO2009042794 | 4/2009 |
| WO | WO2009068485 | 6/2009 |
| WO | WO2009074861 | 6/2009 |
| WO | WO2009079185 | 6/2009 |
| WO | 2009/086558 A1 | 7/2009 |
| WO | 2009086558 A1 | 7/2009 |
| WO | WO2009104092 | 8/2009 |
| WO | 2009/111088 A2 | 9/2009 |
| WO | 2009111088 A2 | 9/2009 |
| WO | WO2009109860 | 9/2009 |
| WO | WO2009127230 | 10/2009 |
| WO | WO2009132131 | 10/2009 |
| WO | WO2009132206 | 10/2009 |
| WO | 2009146867 A1 | 12/2009 |
| WO | WO2009156852 | 12/2009 |
| WO | WO2010007463 | 1/2010 |
| WO | WO2010007533 | 1/2010 |
| WO | 2010015098 A1 | 2/2010 |
| WO | WO2010019718 | 2/2010 |
| WO | WO2010036948 | 4/2010 |
| WO | WO2010042877 | 4/2010 |
| WO | WO2010053572 | 5/2010 |
| WO | WO2010054401 | 5/2010 |
| WO | WO2010059689 | 5/2010 |
| WO | 2010088537 A3 | 8/2010 |
| WO | WO2010119343 | 10/2010 |
| WO | 2011/001780 A1 | 1/2011 |
| WO | 2011/005799 A2 | 1/2011 |
| WO | 2011005799 A2 | 1/2011 |
| WO | WO2011008974 | 1/2011 |
| WO | WO2011012316 | 2/2011 |
| WO | WO2011068810 | 6/2011 |
| WO | WO2011071860 | 6/2011 |
| WO | WO2011071931 | 6/2011 |
| WO | WO2011075656 | 6/2011 |
| WO | WO2011076807 | 6/2011 |
| WO | WO2011112717 | 9/2011 |
| WO | WO2011127316 | 10/2011 |
| WO | WO2011140627 | 11/2011 |
| WO | WO2012006369 | 1/2012 |
| WO | WO2012006372 | 1/2012 |
| WO | WO2012006376 | 1/2012 |
| WO | WO2012006377 | 1/2012 |
| WO | WO2012006378 | 1/2012 |
| WO | WO2012006380 | 1/2012 |
| WO | WO2012019168 | 2/2012 |
| WO | WO2012030901 | 3/2012 |
| WO | WO2012031043 | 3/2012 |
| WO | WO2012031046 | 3/2012 |
| WO | WO2012034025 | 3/2012 |
| WO | WO2012045075 | 4/2012 |
| WO | WO2012045082 | 4/2012 |
| WO | WO2012135805 | 10/2012 |
| WO | WO2012158736 | 11/2012 |
| WO | WO2012170889 | 12/2012 |
| WO | WO2013006825 | 1/2013 |
| WO | WO2013006837 | 1/2013 |
| WO | 2013/033563 A1 | 3/2013 |
| WO | WO2013039861 | 3/2013 |
| WO | WO2013052523 | 4/2013 |
| WO | WO2013090648 | 6/2013 |
| WO | WO2013096709 | 6/2013 |
| WO | WO2013130161 | 9/2013 |
| WO | WO2013151663 | 10/2013 |
| WO | WO2013151664 | 10/2013 |
| WO | WO2013151665 | 10/2013 |
| WO | WO2013151666 | 10/2013 |
| WO | WO2013151667 | 10/2013 |
| WO | WO2013151668 | 10/2013 |
| WO | WO2013151669 | 10/2013 |
| WO | WO2013151670 | 10/2013 |
| WO | WO2013151671 | 10/2013 |
| WO | WO2013151672 | 10/2013 |
| WO | WO2013151736 | 10/2013 |
| WO | WO2014081507 | 5/2014 |
| WO | WO2014152211 | 9/2014 |
| WO | WO2014160243 | 10/2014 |
| WO | WO2017049245 | 3/2017 |
| WO | WO2017075531 | 5/2017 |
| WO | WO2018089790 | 5/2018 |
| WO | WO2020106946 | 5/2020 |
| WO | WO2010144740 | 12/2020 |
| WO | WO2021038508 | 3/2021 |
| WO | WO2022137133 | 6/2022 |

OTHER PUBLICATIONS

Johanning, F.W., et al., "A sindbis virus mRNA polynucleotide vector achieves prolonged and high level heterologous gene expression in vivo." Nucl. Acids Res.; 1995; pp. 1495-1501; vol. 23(9).

Heyes, J. et al., "Cationic lipid saturation influences intracellular delivery of encapsulated nucleic acids." J. Controlled Release; 2005; pp. 276-287; vol. 107(2).

Jeffs, L.B., et al., "A Scalable, Extrusion-Free Method for Efficient Liposomal Encapsulation of Plasmid DNA" Pharmaceu. Research; 2005; pp. 362-372; vol. 22(3).

El Ouahabi, A., et al., "Double long-chain amidine liposome-mediated self replicating DNA transfection." FEBS Letters; 1996; pp. 108-112; vol. 380(1-2).

Taylor, G., et al., "DNA vaccination against respiratory syncytial virus in young calves." Vaccines; 2005; pp. 1242-1250; vol. 13(10).

Perri, S., et al., "An Alphavirus Replicon Particle Chimera Derived from Venezuelan Equine Encephalitis and Sindbis Viruses is a Potent Gene-Based Vaccine Delivery Vector." J. Virol.; 2003; pp. 10394-10403; vol. 77 (19).

Boxus, M., et al., "DNA Immunization with Plasmids Encoding Fusion and Nucleocapsid Proteins of Bovine Respiratory Synctial Virus Induces a Strong Cell-Mediated Immunity and Protects Calves against Challenge." J. Virol.; 2007; pp. 6879-6889; vol. 81(13).

Maurer, N., et al., "Spontaneous Entrapment of Polynucleotides upon Electrostatic Interaction with Ethanol-Destabilized Cationic Liposomes." Biophysical J.; 2001; pp. 2310-2326; vol. 80(5).

Chiaramoni, et al., "Liposome/DNA systems: correlation between hydrophobicity and DNA conformational changes." Journal of Biological Physics; 2008; pp. 179-188; vol. 34(1-2).

Elbashir, et al., "Duplexes of 21-nucleotide RNAs mediate RNA interference in cultured mammalian cells." Nature; 2001; pp. 494-498; vol. 411(6836).

Geall, et al., "Nonviral delivery of self-amplifying RNA vaccines." Proceedings of the National Academy of the USA; 2012; pp. 14604-14609; vol. 109(36).

Goncalves, et al., "The effect of liposome size on the final lipid/DNA ratio of cationic lipoplexes." Biophysical Journal; 2004; pp. 1554-1563; vol. 86(3).

Kulkarni, et al., "Factors affecting microencapsulation of drugs in liposomes.": Journal of Microencapsulation; 1995; pp. 229-246; vol. 12(3).

Semple, et al., "Efficient encapsulation of antisense oligonucleotides in lipid vesicles using ionizable aminolipids: formation of novel small multilamellar vesicle structures" Biochimica et Biophysica Acta; 2001; pp. 152-166; vol. 1510 (1-2).

Fleeton, et al., "Self-Replicative RNA Vaccines Elicit Protection against Influenza A Virus, Respiratory Syncytial Virus and a Tickborne Encephalitis Virus." Journal of Infectious Disease; 2001; pp. 1395-1398; vol. 183.

Chrai, et al., "Liposomes: A Review Part I: Manufacturing Issues", Biotech Trends, Pharmaceutical Technology; 2002; pp. 28-34.

Tseng, et al., Liposomes incorporated with cholesterol for drug release triggered by magnetic field. "Journal of Medical and Biological Engineering." 2007; pp. 29-34; vol. 27(1).

Ramana, et al., "Development of a liposomal nanodelivery system for nevirapine." Journal of Biomedical Science; 2010; 10; 57.

(56) References Cited

OTHER PUBLICATIONS

Samad, et al., Liposomal drug delivery systems: an updated review Curr. Drug Deliv.; 2007; pp. 297-305; vol. 4(4).
Silva, et al., "Effect of ultrasound parameters for unilamellar liposome preparation." Ultrasonics Sonochemistry; 2010; pp. 628-632; vol. 17(3).
Yamamoto, et al., "Current prospects for mRNA gene delivery." Eur. J of Pharma and Biopharm; 2009; pp. 484-489; vol. 71.
Mockey, M. et al., "mRNA-based cancer vaccine: prevention of B16 melanoma progression and metaqstatis by systemic injection of MART1 and mRNA histidylated lipopolyplexes" Cancer Gene Therapy; 2007; pp. 802-814; vol. 14 (9).
Levine, M. et al., "Vaccine development strategies for improving immunization: the role of modern immunology" Nature Immunol.; 2004; pp. 460-464; vol. 5(5).
Cannon, G., et al., "RNA Based Vaccines" DNA Cell Biol.; 2002; pp. 953-961; vol. 21(12).
Zhou, W.Z., et al., "RNA Melanoma Vaccine: Induction of Antitumor Immunity by Human Glycoprotein 100 mRNA Immunization" Human Gene Therapy; 1999; pp. 2719-2724; vol. 10(16).
Saeki, Y., et al. "Development and Characterization of Cationic Liposomes Conjugated with HVJ (Sendai Virus): reciprocal Effect of Cationic Lipid For In Vitro and In Vivo Gene Transfer" Human Gene Therapy; 1997; pp. 2134-2135; vol. 8(17).
Martinon, F., et al., "Inductions of virus-specific cytotoxic T lymphocytes in vivo by lipsome-entrapped mRNA" Eur. J. Immunol.; 1993; pp. 1719-1722; vol. 23.
Zhang, J., et al., Ionization Behavior of Amino Lipids for siRNA Delivery: Determination of Ionization Constants, SAR, and the Impact of Lipid pKa on Cationic Lipid-Biomembrane Interactions. Langmuir: The ACS Journal of Surfaces and Colloids, ACS; 2011; pp. 1907-1914; vol. 15(5).
Kita, H., et al., "Replication of Genetic Information with Self-Encoded Replicase in Liposomes" Chembiochem; 2008; pp. 2403-2410; vol. 9(15).
Stuart, et al., "A new liposomal formulation for antisense oligodeoxynucleotides with small size, high incorporation efficiency and good stability" Biochimica et Biophysica Acta; 2000; pp. 219-229; vol. 1463(2).
Lonez, C., et al., "Cationic liposomal lipids: From gene carriers to cell signaling" Progress in Lipid Research; 2008; pp. 340-347; vol. 47(5).
Caplen, N.J., et al. "Nucleic acid transfer using cationic lipids." Methods In Mole. Biol.; 2000; 133:1-19.
Hoerr, et al. "In vivo application of RNA leads to induction of specific cytotoxic T lymphocytes and antibodies." Eur. J. Immunol.; 2000; pp. 1-7; vol. 30.
Leitner, et al., "DNA and RNA-based vaccines: principles, progress and prospects" Vaccine; 1999; pp. 767-777; vol. 18.
Vadjy, et al., "Mucosal adjuvants and delivery systems for protein-, DNA- and RNA-based vaccines." Immunol. Cell Biol.; 2004; pp. 617-627; vol. 82(6).
Vassilev, et al., "Microparticle-mediated RNA immunization against bovine viral diarrhea virus." Vaccine; 2001; pp. 2012-2019; vol. 19.
Ying, et al., "Cancer therapy using a self-replicating RNA vaccine." Nat. Med.; 1999; pp. 823-827; vol. 5.
Taylor, et al., "DNA vaccination against respiratory syncytial virus in young calves." Vaccine; 2005; pp. 1242-1250; vol. 23(10).
Mockey, et al., "mRNA-based cancer vaccine: prevention of B16 melanoma progression and metastasis by sytemic injection of MART1 mRNA histidylated lipopolyplexes." Cancer Gene Therapy; 2007; pp. 802-814; vol. 14.
Amidi et al., "Antigen-expressing immunostimulatory liposomes as a genetically programmable synthetic vaccine", Systems and Synthetic Biology, (2011) 5:21-31.
Amidi et al., "Optimization and quantification of protein synthesis inside liposomes", J. Liposome Reserach, 2010; 20 (1): 73-83.
Bauer et al., "Toll-like receptors (TLRs) and innate immunity", Handbook of Experimental Pharmacology, ISBN 978-3-540-72166-6, 2008, pp. i-xi, 1-240, and a cover page (2008).

U.S. Appl. No. 61/223,347, filed Jul. 6, 2009, Geall et al.
U.S. Appl. No. 61/280,510, filed Nov. 4, 2009, Cullis et al.
U.S. Appl. No. 61/223,347, priority document to WO2011005799.
Aberle, "Humeral and Cellular Immune Response to RNA Immunization with Flavivirus Replicons Derived from Tick-Borne Encephalitis Virus", Journal of Virology; 2005; pp. 15107-15113; vol. 79(24).
Acheampong, Samuel et al.; "Ionization and transfection activity of n-methyl-substituted carbamoyl-cholesterol derivatives", Journal of Biophysical Chemistry, vol. 2, No. 2, 53-62; 2011.
Adler et al., "Role of human cytomegalovirus UL131A in cell type-specific virus entry and release," J. Gen. Virol., 2006, 87:2451-2460.
Aissaoui et al.: "Efficient topical delivery of plasmid DNA to lung in vivo mediated by putative triggered, PEGylated pDNA nanoparticles", Journal of Controlled Release, Elsevier, Amsterdam, NL, vol. 154, No. 3, Jun. 4, 2011 Jun. 4, 2011), pp. 275-284.
Amidi, "Induction of humoral and cellular immune responses by antigen-expressing immunostimulatory liposomes." Journal of Controlled Release; Aug. 1, 2012; p. 3, left-hand column p. 20, lines 13-14 example 1.
Anderson et al. "Incorporation of pseudouridine into mRNA enhances translation by diminishing PKR activation," Nucleic Acids Research, 38(17):5884-5892 (2010).
Annex A—Effects of Charge Ratio on SAM-LNP Formulation and In Vitro activity.
Anonymous, "Mengovirus", Wikipedia, (Apr. 25, 2020), pp. 1-2, URL: https://en.wikipedia.org/wiki/Mengovirus.
Arvin AM, Gershon AA. Live attenuated varicella vaccine. Annu Rev Microbial. 1996;50:59-100.
Atwood, et al., "Comprehensive Supramolecular Chemistry II" Gen. Prin. of SupraMol. Chem. and Mol. Recogn.; pp. 141-143.
Ausubel et al., Short protocols in molecular biology.
Auxiliary requests 1, 2 and 3 (claims 1-13) filed in relation to the Opposition of European Patent No. 2590676B1 Appln No. 11741348. 4) (6 pages).
Babiuk, S., et al., "Electroporation improves the efficacy of DNA vaccines in large animals," Vaccine; 2002, pp. 3399-3408; vol. 20(27-28).
Bagarazzi, M. L., et al., "Immunotherapy against HPV16118 generates potent TH1 and cytotoxic cellular immune responses," Science Translational Medicine; 2012; vol. 4(155), pp. 1-14.
Bailey et al., "Modulation of membrane fusion by asymmetric transbilayer distributions of amino lipids," Biochemistry, 33:12573-80 (1994).
Balasuriya et al., "Expression of the two major envelope proteins of equine arteritis virus as a heterodimer is necessary for induction of neutralizing antibodies in mice immunized with recombinant venezuelan equine encephalitis virus replicon particles," J. Virol., 2000, 74(22):10623-10630.
Barai, V.N. et al. Production of highly purified RNA from yeast using calcium. Applied Biochemistry and Microbiology. 1995; 31(5): 421-424.
Barichello JM, et al., Complexation of siRNA and pDNA with cationic liposomes: the important aspects in lipoplex preparation, Methods Mil. Biol., 2010, 605: 461-72 (Nov. 21, 2009).
Barnett et al., "Antibody-Mediated Protection against Mucosa! Simian-Human Immunodeficiency Virus Challenge of Macaques Immunized with Alphavirus Replicon Particles and Boosted with Trimeric Envelope Glycoprotein in MF59 Adjuvant," Journal of Virology, 84(12):5975-5985 (2010).
Barratt, "Therapeutic applications of colloidal drug carriers." PSTT, 2000, vol. 3, No. 5, pp. 163-171.
Bernstein et al., "Randomized, double-blind, Phase 1 trial of an alphavirus replicon vaccine for cytomegalovirus in CMV seronegative adult volunteers," Vaccine, 28:484-493 (2010).
Bettinger T et al. (2001) Nucleic Acids Research 29(18): 3882-3891.
Biochemistry/Lubert Stryer (1995) 4th Ed.: title pages and p. 23.
Birdi, K.S., (Ed.), Handbook of Surface and Colloidal Chemistry, CRC Press., Boca Raton, pp. 119-156.
Blakney, "The next generation of RNA vaccines: self-amplifying RNA." Document obtained from https://portlandpress.com/biochemist/

(56) References Cited

OTHER PUBLICATIONS article/43/4/14/229206/The-next-generation-of-RNA-vaccines-self on Sep. 20, 2021, originally published Aug. 2021, pp. 14-17. (Year: 2021).

BMGF Report, "Summary of stability data for licensed vaccines," Working in Tandem Ltd, 2012, pp. 1-17.

Bogers, et al., "Macaques Primed with Self-Amplifying RNA Vaccines Expressing HIV-1 Envelope and Boosted with Recombinant Protein Show Potent T- and B-Cell Responses" poster at the AIDS Vaccine 2012 meeting; Sep. 9-12, 2012; Boston, MA USA.

Bogers, et al., "Potent Immune Responses in Rhesus Macaques Induced by Nonviral Delivery of a Self-amplifying RNA Vaccines Expressing HIV Type 1 Envelope With a Cationic Nanoemulsion." J. Infectious Disease; 2015; pp. 947-955; vol. 211.

Bramwell, "The rational design of vaccines," (DDT. 2005; 10(22): 1527-1534).

Bringmann et al., "RNA Vaccines in Cancer Treatment," Journal of Biomedicine and Biotechnology, 2010:1-12 (2010).

Brito et al., "Self-Amplifying mRNA Vaccines", Advances in Genetics, vol. 89; p. 179-233; 2015.

Brito et al., "A Cationic Nanoemulsion for the delivery of next-generation RNA vaccines," Molecular Therapy, 2014; pp. 2118-2129, vol. 22.

Britt et al., "Cell surface expression of human cytomegalovirus (HCMV) gp55-116 (GB): use of HCMV-recombinant vaccinia virus-infected cells in analysis of the human neutralizing antibody response," J. Virol., 1990, 64(3):1079-1085.

Britt et al., "Cytomegalovirus," In Fields Virology, 3rd edition, BN Fields, DM Knipe, PM Howley (ed.), Philadelphia, PA, Lippincott-Raven, 1996, pp. 2493-2523.

Britt et al., "Human cytomegalovirus virion proteins," Hum. Immunol., 2004, 65:395-402.

Broz, et al. "Newly described pattern recognition receptors team up against intracellular pathogens", Nat. Rev. Immunol. 13:8: 551-565 (2013).

Buyens et al., "Elucidating the encapsulation of short interfering RNA in PEGylated cationic liposomes," Langmuir, 25(9) :4886-4891 (2009).

Buza, J et al., "CD14+ cells are required for IL-12 response in bovine blood mononuclear cells activated with Toll-like receptor (TLR) 7 and TLR8 ligands", Vet. Immunol. Immunopath. 126(3-4): 273-282 (2008)—XP025676816.

Carine et al., "Vaccination of calves using the BRSV nucleocapsid protein in a DNA prime-protein boost strategy stimulates cell-mediated immunity and protects the lungs against BRSV replication and pathology," Vaccine Elsevier LTD, GB, 26(37):4840-4848 (2008).

Carralot, J.P., et al., "Polarization of immunity induced by direct injection of naked sequence-stabilized mRNA vaccines", Cell. Mole. Life Sci. 61(18): 2418-2424 (2004)—XP002355208.

Certified U.S. Appl. No. 61/223,347, filed Jul. 6, 2009.

Certified U.S. Appl. No. 61/265,653, filed Dec. 1, 2009.

Certified U.S. Appl. No. 61/361,780, filed Jul. 6, 2010.

Certified U.S. Appl. No. 61/361,794, filed Jul. 6, 2010.

Cha et al., "Human cytomegalovirus clinical isolates carry at least 19 genes not found in laboratory strains," J. Virol., 1996, 70(1):78-83.

Chambers, et al., "Vaccination of mice and cattle with plasmid DNA encoding the *Mycobacterium bovis* antigent MPB83." Clinical Infection Diseases; 2000; pp. S283-S287; vol. 30(3).

Chee et al, "Hypothetical Protein UL128", UniProtKB/Swiss-Prot: P16837, Dep. Feb. 1, 1991.

Chee et al., "Analysis of the protein-coding content of the sequence of human cytomegalovirus strain AD169," Curr. Top. Microbiol. Immunol., 1990, 154:125-169.

Cheng et al., "Enhancement of Sindbis virus self-replicating RNA vaccine potency by linkage of *Mycobacterium tuberculosis* heat shock protein 70 gene to an antigen gene", Journal of Immunology, 166:6218-6226 (2001).

Cheng WF, Hung CF, Lee CN, Su YN, Chang MC, He L, Wu TC, Chen CA, Hsieh CY. Naked RNA vaccine controls tumors with down-regulated MHC class I expression through NK cells and perforin-dependent pathways. Eur J Immunol. Jul. 2004;34(7):1892-900.

Cheng, W.F., et al, "Enhancement of Sindbis Virus Self-Replicating RNA Vaccine Potency by Linkage of Herpes Simplex Virus Type 1 VP22 Protein to Antigen", J. Viral. 75(5): 2368-2376 (2001)—XP002201711.

Communication of the Board of Appeal in relation to the Opposition of European Patent No. 2590676B1 Appln No. 11741348.4) (12 pages).

Communication of the Board of Appeals pursuant to Art. 15(1) of the Rules of Procedure of the Boards of Appeal dated Mar. 25, 2021, in European Patent Application Publication No. 2590676.

Compton et al., "Receptors and immune sensors: the complex entry path of human cytomegalovirus," Trends Cell. Bio., 2004, 14(1):5-8.

Conry, et al., "Characterization of a Messenger RNA Polynucleotide Vaccine Vector." Cancer Research; 1995; pp. 1397-1400; vol. 55.

Corresponding parent application: U.S. Appl. No. 16/114,621, filed Aug. 28, 2018.

Cox, et al., "Bovine herpesvirus 1: immune responses in mice and cattle injected with plasmid DNA." Journal of Virology; 1993; pp. 5664-5667; vol. 67(9).

Crooke Stanley T., (Ed.), "Antisense Drug Technology: Principles, Strategies, and Applications," 2nd ed., chapter 9 (2008), pp. 237-270.

Cui, et al., DNA Vaccine, Advances in Genetics; 2005; pp. 257-289; vol. 54.

Cullis, Pieter; WO2011140627 (certified Priority Document U.S. Appl. No. 61/280,510).

Cavagna, et al.; "7—Signs and Work of Man"; The National Park of the Casentine Forests; 2003; pp. 175.

Davis, et al., "DNA vaccine for hepatitis B Evidence for immunogenicity in chimpanzees and comparison with other vaccines." Proc. Natl Acad Sci USA; 1996; pp. 7213-7218; vol. 93.

Davison AJ, UL115; gL [Human Herpesvirus 5]. NCBI Reference Sequence: YP_081555.1, Dep. Sep. 16, 2004.

Davison AJ, UL130 [Human Herpesvirus 5]. NCBI Reference Sequence: YP_081565.1, Dep. Sep. 16, 2004.

Davison AJ, UL131A [Human Herpesvirus 5]. NCBI Reference Sequence: YP_081566.1, Dep. Sep. 16, 2004.

Davison AJ, UL75; gH [Human Herpesvirus 5]. NCBI Reference Sequence: YP_081523.1, Dep. Sep. 16, 2004.

Davison et al., "The human cytomegalovirus genome revisited: comparison with the chimpanzee cytomegalovirus genome," J. Gen. Virol., 2003, 84:17-28.

Declaration Andrew Geall dated Sep. 11, 2014.

Declaration by Prof. Peter Liljestrom, dated Mar. 31, 2019 submitted in EP 2591114.

Declaration by Prof. Peter Liljestrom, dated Aug. 7, 2018 submitted in EP 2591114.

Declaration by Russell Johnson cited in EP2729126 on Jul. 4, 2018 and in opposition filed on Sep. 23, 2021 (4 pages).

Declaration of Prof. Liljestrom submitted to the European Patent Office in the opposition proceedings concerning EP2590676 B1.

Declaration of Professor Liljestrom dated Dec. 11, 2018 submitted in EP2590676, itself having annexes A-G.

Declaration of Russell N. Johnson dated Dec. 10, 2018.

Deering, et al., "Nucleic acid vaccines: prospects for non-viral delivery of mRNA vaccines." Expert Opinion Drug Delivery; 2014; pp. 885-899; vol. 11(6).

Defang et al., "Induction of neutralizing antibodies to Hendra and Nipah glycoproteins using a Venezuelan equine encephalitis virus in vivo expression system," Vaccine Elsevier Ltd. GB,29(2):212-220 (2010).

Diebold, S.S., et al., "Innate Antiviral Responses by Means of TLR7-Mediated Recognition of Single-Stranded RNA", Science 303(5663): 1529-1531 (2004).

Dolan et al, "Genetic Content of Wild-Type Human Cytomegalovirus", J. Gen. Virol. May 2004; 85(Pt 5):1301-12.

(56) References Cited

OTHER PUBLICATIONS

Dunn et al., "Functional profiling of a human cytomegalovirus genome," Proc. Natl. Acad. Sci. USA, 2003, 100 (24):14223-14228.
Dupuis et al., "Dendritic cells internalize vaccine adjuvant after intramuscular injection", Cellular Immunology, 186:18-27 (1998).
Dupuis et al., "Distribution of DNA vaccines determines their immunogenicity after intramuscular injection in mice," Journal of Immunology, 165:2850-2858 (2000).
Elkington et al., "Ex Vivo Profiling of CD8+-T-Cell Responses to Human Cytomegalovirus Reveals Broad and Multispecific Reactivities in Healthy Virus Carriers," Journal of Virology (2003), vol. 77, No. 9, pp. 5226-5240.
Elliott et al., "Alphavirus replicon particles encoding the fusion or attachment glycoproteins of respiratory syncytial virus elicit protective immune responses in BALB/c mice and functional serum antibodies in rhesus macaques," Vaccine Elsevier LTD, GB, 25(41):7132-7144, (2007).
Encyclopedia Britannica House Mouse; 2005, p. 963.
EP12738679.5 Third Party Observations in accordance with Article 115 EPC; Mar. 8, 2019.
Er, et al., "The encapsulation and release of guanosine from PEGylated liposomes." Journal of Liposome Research, 2009, vol. 19, No. 1, pp. 29-36.
Espuelas, Socorro, et al., "Effect of synthetic lipopeptides formulated in liposomes on the maturation of human dendritic cells," Molecular Immunology 42 (2005): 721-729, and Corrigendum, Molecular Immunology 43 (2006) 772.
Evers, M., et al, "State-of-the-Art Design and Rapid-Mixing Production Techniques of Lipid Nanoparticles for Nucleic Acid Delivery", Small Methods, 2:1-20, (2018).
Excerpt from "Chemical Book" on DLinDMA Sep. 9, 2021.
Excerpt from "Comprehensive Supermolecular Chemistry II" 2017; vol. 1.
Excerpt from PubChem: Transfectam.
Expert opinion Prof. Schubert.
Faneca, H et al., Drug Delivery Systems: Advanced Technologies Potentially Applicable in Personalised Treatment, Advances in Predictive, Preventive and Personalised Medicine 4:153-184, 2013.
Faure, et al., "Control of the in vivo Biodistribution of Hybrid Nanoparticles with Different Poly(ethylene glycol) Coatings." Small, 2009, vol. 5, No. 22, pp. 2565-2575.
Felgner, et al., "Lipofection: A Highly Efficient, Lipid-Mediated DNA-Transfection Procedure." Proc. Natl. Acad. Sci. USA; 1987pp. 7413-7417; vol. 84.
Fenske, "Liposomal Nanomedicines: An Emerging Field", Toxicologic Pathology; 2008; pp. 21-29; vol. 36, No. 1.
Final Decision and Upheld Claims from EP2591114, European Equivalent of U.S. Appl. No. 13/808,153, dated Nov. 27, 2018.
Fraenkel-Conrat et al., (Ed.), Virology second edition, Prentice-Hall Inc., Englewood Cliffs, New Jersey; 1988; from Chapter 3, "Enveloped Plus-strand RNA Viruses:Togaviridae", pp. 96-103.
Fraenkel-Conrat, "Togaviridae", Virology second edition, Prentice-Hall Inc.; 1988; p. 2 pp. 99.
Freddolino, et al, "Molecular Dynamics Simulations of the Complete Satellite Tobacco Mosaic Virus." Structure; 2006; pp. 437-449; vol. 14.
Frolov et al., "Alphavirus-based expression vectors: Strategies and applications," 93 Proceedings of the National Academy of Sciences USA (1996).
Fynan, E.F., et al., DNA vaccines: Protective immunizations by parenteral, mucosal, and gene-gun inoculations; Proc Natl Acad Sci.; 1993; pp. 11478-11482; vol. 90.
Gamvrellis A. et al. Vaccines that facilitate antigen entry into dendritic cells. Immunol Cell Biol. Oct. 2004; 82(5): 506-516.
Gao & Hui, Gene Therapy 8 (2001), 855-863.
Garcia-Valcarcel M, Fowler WJ, Harper DR, Jeffries DJ, Layton GT. Induction of neutralizing antibody and T-cell responses to varicella-zoster virus (VZV) using Ty-virus-like particles carrying fragments of glycoprotein E (gE). Vaccine. Apr.-May 1997;15(6-7): 709-19.

Geall, et al. "Using self-amplifying mRNA vaccines to facilitate a rapid response to pandemic influenza" Eur. Pharm. Review 19:3 20-23 (2014).
Geisbert, et al., "Postexposure Protection of Guinea Pigs against a Lethal Ebola Virus Challenge Is Conferred by RNA Interference", Journal of Infectious Diseases; 2006; pp. 1650-1657; vol. 193.
Genini et al., "Serum antibody response to the gH/gL/pUL 128-131 five protein complex of Serum antibody response to the gH/gL/pUL 128-131 five-protein complex of human cytomegalovirus (HCMV) in primary and reactivated HCMV infections," Journal of Clinical Virology, 52:113-118 (2011).
Giraud A, Ataman-Onal Y, Battail N, Piga N, Brand D, Mandrand B, Verrier B. Generation of monoclonal antibodies to native human immunodeficiency virus type 1 envelope glycoprotein by immunization of mice with naked RNA. J Virol Methods.Apr. 1999;79(1):75-84.
Giuliani et al., "A universal vaccine for serogroup B meningococcus," Proc. Natl. Acad. Sci. U. S. A, 2006, vol. 103, No. 29, pp. 10834-10839.
Glaxosmithkline, SAM/Protein Mixed Modality Study Data, PowerPoint presentation (2019).
Graham, Barney, "Biological challenges and technological opportunities for respiratory syncytial virus vaccine development," Immunological Reviews, 239(1):149-166 (2011).
Graham, et al., "Priming Immunization Determines T Helper Cytokine mRNA Expression Patterns in Lungs of Mice Challenged with Respiratory Syncytial Virus." The Journal of Immunology; Aug. 15, 1993; pp. 2032-2040; vol. 151, No. 4.
Granstein, et al., "Induction of Anti-Tumor Immunity with Epidermal Cells Pulsed with Tumor-Derived RNA or Intradermal Administration of RNA." Journal of Investigative Dermatology; 2000; pp. 632-636; vol. 114(4).
Greer, C, et al., "A chimeric alphavirus RNA replicon gene-based vaccine for human parainfluenza virus type 3 induces protective immunity against intranasal virus challenge", Vaccine 25(3): 481-489 (2007)—XP005798901.
Hahn et al., "Deletion Mapping of the Encephalomyocarditis Virus Primary Cleavage Site". J. Virol. Aug. 2001; 75 (15):7215-8.
Hamm et al., "Immunostimulatory RNA is a potent inducer of antigen-specific cytotoxic and hum oral immune response in vivo," International Immunology, 2007, vol. 19(3); 297-304.
Harvey et al. Kunjin Virus Replicon Vectors for Human Immunodeficiency Virus Vaccine Development 2003 Journal of Virology vol. 77 No. 14 pp. 7796-7803.
Hatakeyama, et al., "Systemic delivery of siRNA to tumors using a lipid nanoparticle containing a tumor-specific cleavable PEG-lipid." Biomaterials, 2011, vol. 32, pp. 4306-4316.
Heidel, J.D., et al., "Administration in non-human primates of escalating intravenous doses of targeted nanoparticles containing ribonucleotide reductase subunit M2 siRNA," Proc. Natl Acad Sci USA; 2007; pp. 5715-5721; vol. 104(14).
Herweijer et al., "Self-amplifying vectors for gene delivery," Advanced Drug Delivery Reviews, 27; 1997; pp. 5-16.
Hidmark et al., "Humoral Responses against Coimmunized Protein Antigen but Not against Alphavirus-Encoded Antigens Require Alpha/Beta Interferon Signaling," Journal of Virology, 80(14):7100-7110 (2006).
Hiroshi, et al., "Replication of Genetic Information with Self-Encoded Replicase in Liposomes." ChemBioChem; Oct. 13, 2008; pp. 2403-2410; vol. 9(15).
Ho, "Cytomegalovirus," In Principles and Practice of Infectious Diseases, GL Mandell, RG Douglas, and JE Bennett (ed.), Wiley, New York, NY, 1979, pp. 1307-1323.
Hobom et al., "Fast screening procedures for random transposon libraries of cloned herpesvirus genomes: mutational analysis of human cytomegalovirus envelope glycoprotein genes," J. Virol., 2000, 74(17):7720-7729.
Hoerr, I, Tissue Engineering 13(4): 886-887; 2007.
Hofmann et al., "Physiochemical Properties of Bile Acids and their Relationship to Biological Properties: An Overview of the Problem," J Lip Res., vol. 25, (1984), pp. 1477-1489.

(56) References Cited

OTHER PUBLICATIONS

Hope, et al., "Chapter 8: Reduction of Liposome Size and Preparation of unilamellar Vesicles by Extrusion Techniques," Liposome Technology; 1993; pp. 123-139; vol. 1.
Hornung, et al., "5'-Triphosphate RNA Is the Ligand for RIG-I" Science; 2006; vol. 314; pp. 994-997.
Huang, et al., "Immunization with a bovine herpesvirus 1 glycoprotein B DNA vaccine induces cytotoxic T-lymphocyte responses in mice and cattle," Journal of General Virology; 2005; pp. 887-898; vol. 86(4).
Iavarone et al., "A Point Mutation in the Amino Terminus of TLR7 Abolishes Signaling without Affecting Ligand Binding", J. Immunol, (2011), vol. 186, pp. 4213-4222.
Imagines Immunization Merriam Webster's Medical Desk Dictionary; 1993; pp. 326-327.
Immordino, et al., "Stealth liposomes: review of the basic science, rationala, and clinical application, existing and potential." International Journal of Nanomedicine, 2006, vol. 1, pp. 297-315.
International Search Report for International Application No. PCT/2012/045847 dated Oct. 10, 2012.
International Search Report for International Application No. PCT/2012/045854 dated May 9, 2014.
Johnson signed Declaration dated Oct. 22, 2020 (9 pages).
Johnson, Russell, "Effects of Charge Ratio on SAM-LNP Formulation and In Vitro activity," pp. 1-4.
Johnson, T, et al., "TLR9 agonist, but not TLR7/8, functions as an adjuvant to diminish FI-RSV vaccine-enhanced disease, while either agonist used as adjuvant during primary RSV infection increases disease severity", Vaccine 27 (23): 3045-3052 (2009).
Jones et al. "DNA vaccination protects against an influenza challenge in a double-blind randomised placebo-controlled phase 1b clinical trial" Vaccine 27 (2009): 2506-2512.
Ju J., et al., Int. J. Mol. Sci. 16:5666-5681; 2015.
Kamrud KI, Alterson K, Custer M, Dudek J, Goodman C, Owens G, Smith JF. Development and characterization of promoterless helper RNAs for the production of alphavirus replicon particle. J Gen Virol. Jul. 2010;91(Pt 7):1723-7. Epub Feb. 24, 2010.
Kariko, et al., "mRNA Is an Endogenous Ligand for Toll-like Receptor 3*"; The Journal of Biological Chemistry; 2004; vol. 279, No. 13; pp. 12542-12550.
Kariko, et al., "Suppression of RNA Recognition by Toll-like Receptors: The Impact of Nucleoside Modification and the Evolutionary Origin of RNA"; Immunity; 2005; vol. 23; pp. 165-175.
Kawano, et al., "Effects of Polyethylene Glycol Spacer Length and Ligand Density on Folate Receptor Targeting of Liposomal Doxorubicin In Vitro." Journal of Drug Delivery, 2011, vol. 2011, No. 160967, pp. 1-6.
Khan, K. H., "DNA vaccines: roles against diseases," Germs; 2013; pp. 26-35; vol. 3(1).
Kimura et al. "Recombinant Varicella-Zoster Virus Glycoproteins E and I: Immunologic Responses and Clearance of Virus in a Guinea Pig Model of Chronic Uveitis", 1998 Journal of Infectious Diseases 178:310-317.
Kimura et al. "Varicella-Zoster Virus Glycoproteins E and I Expressed in Insect Cells Form a Heterodimer That Requires the N-Terminal Domain of Glycoprotein I", 1997 Virology 233:382-391.
Kinnan, et al., "Enhanced Immunogenicity to *Mycobacterium tuberculosis* by Vaccination with an Alphavirus Plasmid Replicon Expressing Antigen 85A" Infection and Immunity; 2003; pp. 575-579; vol. 71(1).
Kirman, et al., "Enhanced Immunogenicity to *Mycobacterium tuberculosis* by Vaccination with an Alphavirus Plasmid Replicon Expressing Antigen BSA" Infection and Immunity; 2003; pp. 575-579; vol. 71(1).
Klibanov A L et al: "Amphipathic polyethyleneglycols effectively prolong the circulation time of liposomes", FEBS Letters, Elsevier, Amsterdam, NL, vol. 268, No. 1,Jul. 30, 1990 (Jul. 30, 1990), pp. 235-237.
Knipe et al., "Fields Virology," 4th edition, Lippincott Williams & Wilkins, 2001; pp. 690-692; vol. 1, p. 2.

Kofler, et al. "Mimicking live flavivirus immunization with a noninfectious RNA vaccine." Proc. Natl. Acad. Sci. USA; 2004; pp. 1951-1956; vol. 101(7).
Kornbluth at al. "Immunostimulatory combinations: designing the next generation of vaccine adjuvants," Journal of Leukocyte Biology, 2006, vol. 80, pp. 1084-1102.
Kumar et al., "Toll-like receptors and innate immunity," Biochemical and Biophysical Research Communications, 388:621-625 (2009).
Kumar, et al., "Single histidine residue in head-group region is sufficient to impart remarkable gene transfection properties to cationic lipids: evidence for histidine-mediated membrane fusion at acidic pH". Gene Therapy; 2003; vol. 10; pp. 1206-1215.
Kumar, et al., Molecular Therapy 9(S1): S258-S259, 2004.
Kutinova et al., "Immune response to vaccinia virus recombinants expressing glycoproteins gE, GB, gH, and gL of varicella-zoster virus," Virol., 2001, 280:211-220.
Kutzler, et al., "DNA vaccines; ready for prime time?" Nature Reviews; Genetics; 2008; pp. 776-788; vol. 9(10).
Lazzaro et al., "CD8 T-cell priming upon mRNA vaccination is restricted to bone-marrow-derived antigen-presenting cells and may involve antigen transfer from myocytes," Immunology, 146:312-326 (2015).
Lee et al., "Multiagent vaccines vectored by Venezuelan equine encephalitis virus replicon elicits immune responses to Marburg virus and protection against anthrax and botulinum neurotoxin in mice," Vaccine, Elsevier, Amsterdam, NL, vol. 24, No. 47-48; pp. 6886-6892; Nov. 17, 2006.
Lee, et al., "Venezuelan Equine Encephalitis Virus-Vectored Vaccines Protect Mice Against Anthrax Spore Challenge." Infection and Immunity; 2003; pp. 1491-1496; vol. 71.
Levy; "Quantitation of supercoiled circular content in plasmid DNA solutions using a fluorescence based method", Nucleic Acids Res.; 2000; 28:e57.
Li et al., "Protection against Respiratory Syncytial Virus Infection by DNA Immunization," J Exp Med., vol. 188, (1998), pp. 681-688.
Liljestrom, et al., "A new generation of animal cell expression vectors based on the Semliki Forest virus replicon," Biotechnology, 9:1356-1361 (1991).
Liljestrom, et. al., "In vitro mutagenesis of a full-length cDNA clone of Semliki Forest virus: the small 6,000-molecular-weight membrane protein modulates virus release," Journal of Virology, Aug. 1991; 65(8): 4107-4113.
Liu Y & Huang L (2010) Molecular therapy 18(4): 669-670.
Ljungberg et al., "Increased Immunogenicity of a DNA-Launched Venezuelan Equine Encephalitis Virus-Based Replicon DNA Vaccine," Journal of Virology, Dec. 2007, p. 13412-13423.
Ljungman et al., "Definitions of cytomegalovirus infection and disease in transplant recipients," Clin. Infect. Dis., 2002, 34:1094-1097.
Lobue, et al. "Multivalent norovirus vaccines induce strong mucosal and systemic blocking antibodies against multiple strains." Vaccine; 2006; pp. 5220-5234; vol. 24.
Lorenzi, et al. "Intranasal vaccination with messenger RNA as a new approach in gene therapy: use against tuberculosis," BMC Biotechnology 10.1 (2010): 1-11.
Lu, et al., "Optimization of methods to achieve mRNA-mediated transfection of tumor cells in vitro and in vivo employing cationic liposome vectors," Cancer Gene Ther., 1(4):245-252 (1994) (abstract).
Lundstrom et al., "Biology and application of alphaviruses in gene therapy", Gene Therapy; vol. 12; Suppl 1; pp. S92-S97, 2005.
Lundstrom, "Semliki Forest Virus Vectors for Gene Therapy," Expert Opinion on Biological Therapy, vol. 3, No. 5, (2003), pp. 771-777.
Lv et al., "Toxicity of cationic lipids and cationic polymers in gene delivery." Journal of Controlled Release, vol. 114 (2006), pp. 100-109. (Year: 2006).
Lyubchenko, et al., "Visualization of supercoiled DNA with atomic force microscopy in situ" Proc. Natl. Acad Sci. USA; 1997; pp. 496-501; vol. 94.
Macagno et al., "Isolation of Human Monoclonal Antibodies That Potently Neutralize Human Cytomegalovirus Infection by Targeting Different Epitopes on the gH/gL/UL128-131A Complex", 2010 Journal of Virology 84 (2):1005-1013.

(56) References Cited

OTHER PUBLICATIONS

MacLachlan, I., "Liposomal formulations for nucleic acid delivery", Antisense Drug Technologies, 2nd Edition, Chapter 9, 237-270, 2007.
Mahato RI, Water insoluble and soluble lipids for gene delivery, Adv. Drug Delivery Rev.,2005, 57(5):699-712.
Malone et al., "Cationic liposome-mediated RNA transfection ", Proc. Natl. Acad. Sci. (PNAS) USA: Biochemistry; 86:16; 6077-6081; 1989.
Manning, et al., "Infectivity of Liposomally Encapsulated Nucleic Acids Isolated From EMC Virus and Scrapie-Infected Mouse Brain," Intervirology; vol. 20; 1983; pp. 164-168.
Martin, et al., "Characterization of formaldehyde-inactivated poliovirus preparations made from live-attenuated strains." Journal of General Virology; 2003; pp. 1781-1788; vol. 84.
Matsuura, et al., "Polycation liposome-mediated gene transfer in vivo," Biochimica et Biophysica Acta, vol. 1612, 2003, pp. 136-143.
McGlone, et al., "Pig Production: Biological Principles and Applications" Chapter 8; 2000; pp. 99.
Merriam-Webster definition of "virion" (downloaded Mar. 14, 2016).
Mocarski et al., "Cytomegalovirus and their replication," In Fields Virology, 4th edition, vol. 2, 2001, DM Knipe and PM Howley (ed.), Lippincott Williams and Wilkins, Philadelphia, PA, pp. 2629-2673.
Mok et al., "Venezuelan equine encephalitis virus replicon particles encoding respiratory syncytial virus surface glycoproteins induce protective mucosal responses in mice and cotton rats," Journal of Virology, The American Society for Microbiology, 81(24):13710-13722 (2007).
Morris-Downes, et al., "A recombinant Semliki Forest virus particle vaccine encoding the prME and NS1 proteins of louping ill virus is effective in a sheep challenge model." Vaccine; 2001; pp. 3877-3884; vol. 19.
Mosca et al., "Molecular and cellular signatures of human vaccine adjuvants," Proc. Natl. Acad. Sci. USA, 105:10501-10506 (2008).
Mossman, "Protection against Lethal Simian Immunodeficiency Virus SIVsmmPBj14 Disease by a Recombinant Semliki Forest Virus gp160 Vaccines and by a gp120 Subunit Vaccine." J. Virology; 1996; pp. 1953-1960; vol. 70.
Murphy et al., "Coding potential of laboratory and clinical strains of cytomegalovirus," Proc. Natl. Acad. Sci. USA, 2003, 100(25):14976-14981.
Na Slund et al "Role of innate signalling pathways in the immunogenicity of alphaviral replicon-based vaccines," Virology Journal, 8(1):36 (2011).
Narang, et al., Bioconjugate Chem. 16 (2005), 156-166.
NCBI reference sequence. "*Homo sapiens* coagulation factor VIII (F8), transcript variant 1, mRNA." Mar. 2016, pp. 1-18.
Notice of Opposition in relation to European Patent No. 259110381 (Appln No. 11736498.4) dated May 28, 2020 (44 pages).
Notice of Opposition in relation to European Patent No. 2591103B1 (Appln No. 11736498.4) dated May 27, 2020 (17 pages).
Obata, "Evaluation of pH-responsive liposomes containing amino acid-based zwitterionic lipids for improving intracellular drug delivery in vitro and in vivo", Journal of Controlled Release; 2010; pp. 267-276; vol. 142, No. 2.
Office Action issued in U.S. Appl. No. 13/808,080, dated May 25, 2022.
Office Action issued in U.S. Appl. No. 17/560,019, dated May 31, 2022.
Office Action issued in U.S. Appl. No. 17/560,116, dated May 31, 2022.
O'Hagan et al., "Induction of potent immune responses by cationic microparticles with adsorbed human immunodeficiency virus DNA vaccines," J Virology, (2001), vol. 75, pp. 9037-9043.
Opponents arguments by Dr. Georg Schnappauf filed on Jan. 14, 2022, in opposition to European Patent No. 2591103.
Opponents arguments by Janssen Vaccines & Prevention B.V. filed on Jan. 14, 2022 in opposition to European Patent No. 2591103.
Opposition Document D60—Declaration of Russell N. Johnson from EP2591114, European Equivalent of U.S. Appl. No. 13/808,153, filed Aug. 8, 2018.
Organism overview of Encephalomyocarditis virus and of Poliovirus obtained from PubMed "Encephalomyocarditis virus." retrieved on Jun. 4, 2019 from https://www.ncbi.nlm.mih.gov/genome/?term=encephalomyocarditis+virus, and "Enterovirus C" retrieved on Jun. 4, 2019 from https://www.ncbi.nlm.nih.gov/genome/?term=poliovirus[orgn].
Ott, et al., "A Cationic sub-micron emulsion [lv159/DOTAP] is an effective delivery system for DNA vaccines," Journal of Controlled Release; 2002; pp. 1-5; vol. 79(1-3).
Oussoren, et al., "Lymphatic Uptake and Biodistribution of Liposomes After Subcutaneous Injection: III. Influence of Surface Modification with Poly(ethyleneglycol)." Pharmaceutical Research, 1997, vol. 14, No. 10, pp. 1479-1484.
Papahadjopoulos, et al., "Cochleate Lipid Cylinders: Formation by Fusion of Unilamellar Lipid Vesicles" Biochim et Biophys Acta; 1975; pp. 483-491; vol. 394.
Papahadjopoulos, et al., "Incorporation of Macromolecules within Large Unilamellar Vesicles (LUV)" Annals NY Academy of Sciences; 1978; pp. 259-267.
Pascolo, "Vaccination With Messenger RNA." Methods in Molecular Medicine, 2006, vol. 127, pp. 23-40.
Patentee's Reply to Opposition in relation to European Patent No. 2591103B1 (Appln No. 11736498.4) dated Oct. 23, 2020 (28 pages).
Peng et al., "The gH-gL complex of herpes simplex virus (HSV) stimulates neutralizing antibody and protects mice against HSV type 1 challenge," J. Virol., 1998, 72(1):65-72.
Phumiamorn, et al., "Induction of humoral and cell-mediated immunity to hepatitis B surface antigen by a novel adjuvant activity of Oka varicella vaccine." Journal of General Virology; 2003; pp. 287-291; vol. 84.
Pomeroy et al., "Cyotmegalovirus: epidemiology and infection control," Am. J. Infect. Control, 1987, 15(3):107-119.
Preliminary Opposition Opinion from EP2591114 (EP Appl. 11736497.6), European Equivalent of U.S. Appl. No. 13/808,153, dated Feb. 23, 2018.
Pschyrembel, Klinisches Wortenbuch Immunisiserung, Immunreaktion; 1997; pp. 747-748.
Pushko, P. et al., Virology, 239: 389-401(1997).
Qa'Dan et al., "ph-Induced Conformational Changes in Clostridium Difficile Toxin B," Infect & Immun., vol. 68, (2000), pp. 2470-2474.
Rayner, et al., "Alphavirus vectors and vaccination", Reviews in Medical Virology; 2002; pp. 279-296; vol. 12.
Reap et al., Development and preclinical evaluation of an alphavirus replicon particle vaccine for cytomegalovirus, Vaccine, Elsevier LTD, GB, 25(42):7441-7449, (2007).
Reap et al., "Cellular and humoral immune responses to alphavirus replicon vaccines expressing cytomegalovirus pp65, IE1 and gB proteins," Clin. Vacc. Immunol., 2007, 14(6):748-755.
Ren et al., "Immunogene therapy of recurrent glioblastoma multiforme with a liposomally encapsulated replication-incompetent Semliki forest virus vector carrying the human interleukin-12 gene—a phase 1/11 clinical protocol", J. Neuro-Oncology, 2003, 64:147-154.
Rishi R Goel, et al., "Distinct antibody and memory B cell responses in SARS-COV-2 naïve and recovered individuals after mRNA vaccination," Science Immunology, vol. 6, eabi6950, Apr. 2021, pp. 1-13; 2021.
Rodriguez A, et al. Cancer Chemother Pharmacol 74:151-166, 2014.
Rodriguez-Gascon et al., Development of nucleic acid vaccines: use of self-amplifying RNA in lipid nanoparticles, International Journal of Nanomedicine, 2014, vol. 9(1), 1833-1843.
Roldao A Mellado MC Castilho LR Carrondo MJ Alves PM. Virlike particles in vaccine development. Expert Rev Vaccines. Oct. 2010;9(10):1149-76.
Rubin, "Clinical approach to infection in the compromised host," In Infection in the Organ Transplant Recipient, 4th edition, R Rubin and LS Young (ed.), Kluwer Academic Press, New York, NY, 2002, pp. 573-679.
Russell Johnson Declaration.

(56) References Cited

OTHER PUBLICATIONS

Ryckman et al., "Characterization of the human cytomegalovirus gH/gL/UL128-131 complex that mediates entry into epithelial and endothelial cells," J. Virol., 2008, 82(1):60-70.
Ryckman et al., "Human cytomegalovirus TR strain glycoprotein O acts as a chaperone promoting gH/gL incorporation into virions, but is not present in virions," J. Virol., 2010, 84(5):2597-2609.
Sacco, et al, "The Average Body Surface Area of Adult Cancer Patients in the UK: A Multicentre Retrospective Study." PloS ONE; 2010; pp. 1-6; vol. 5(1).
Saccoccio, Frances Maria, "Thesis: CMV Vaccine Development based on Epithelial Entry Mediators UL128, UL130, and UL131," Jun. 3, 2011, Retrieved from the Internet: URL: https//digarchiveJibrary. vcu.edu/bitstreamjhandle/10156/3452/SACCOCCIO FRANCES PhD. pdf?sequence=1-1 retrieved on Mar. 18, 2014] Impact on future vaccine design; p. 160 (2011). Chapter: Peptides to UL130 and UL131. Neutralize CMV Infection of Mucosal Epithelial Cells; p. 96.
Sadzuka et al., J. Liposome Res., 13(2), 157-172 (2003).
Saenz-Badillos, et. al., "RNA as a tumor vaccine: a review of the literature", Experimental Dermatology; 200 1; pp. 143-154; vol. 10, Issue 3.
Sawai et al., "A Novel Method of Cell-Specific mRNA Transfection" 64 Molecular Genetics and Metabolism 44-51 (1998).
Saxena et al., "Induction of immune responses and protection in mice against rabies using a self-replicating RNA vaccine encoding rabies virus glycoprotein," Veterinary Microbiology; vol. 136(1-2); 2009; pp. 36-44.
Schedin-Weiss et al., "Antiangiogenic Forms of Antithrombin Specifically Bind to the Anticoagulant Heparin Sequence," Biochemistry, vol. 47, (2008), pp. 13610-13619.
Scheel, et al., "Toll-like receptor-dependent activation of several human blood cell types by protamine-condensed rnRNA"; European Journal of Immunology; 2005; pp. 1557-1566.
Schirrmacher et al., "Intra-pinna anti-tumor vaccination with self-replicating infectious RNA or with DNA encoding a model tumor antigen and a cytokine" Gene Therapy; 2000; pp. 1137-1146; vol. 7.
Schleiss MR. Cytomegalovirus vaccine development. Curr Top Microbiol Immunol. 2008;325:361-82.
Schlesinger et al., "Alphavirus vectors for gene expression and vaccines," Current Opinion in Biotechnology, 1999, 10:434-439.
Schoenmaker, et al., mRNA-lipid nanoparticle COVID-19 vaccines: Structure and stability, International Journal of Pharmaceutics 601; 120586, pp. 1-13; 2021.
Search Report issued in EP Application No. 21298987.3, dated May 25, 2022.
Semple et al., "Rational design of cationic lipids for siRNA delivery," Nature Biotechnology, v. 28 :172-176 (2010).
Shade RO Blundell MC Cotmore SF Tattersall P Astell CR. unknown protein [Human parvovirus B19]. GenBank: AAA66867.1 Dep. 05171995.
Sharma, et al., "To scale or not to scale: the principles of does extrapolation." British Journal of Pharmacology; 2009; pp. 907-921; vol. 157.
Shimamura et al., "Human cytomegalovirus infection elicits a glycoprotein M (gM)/gN-specific virus-neutralizing antibody response," J. Virol., 2006, 80(9):4591-4600.
Singh et al., "The Effect of CTAB Concentration in Cationic PLG Microparticles on DNA Adsorption and in Vivo Performance," Pharmaceutical Research, (2003), vol. 20, pp. 247-251.
Singh, et al., "Cationic microparticles: A potent delivery system for DNA vaccines" Proc Natl Acad Sci USA; 2000; pp. 811-816; vol. 97(2).
Smerdou, et al., "Non-viral amplification systems for gene transfer: Vectors based on alphaviruses," Curr Opin Mal Ther; 1999; pp. 244-251; vol. 1(2).
Smith Korsholm, Karen, et al. "The adjuvant mechanism of cationic dimethyldioctadecylammonium liposomes," Immunology 121(2) (2007): 216-226.

Soong et al., "PEG Molecular Weight and Lateral Diffusion of PEG-ylated Lipids in Magnetically Aligned Bicelles," BBA, (2007), pp. 1805-1814.
Spelios et al., Biophys. Chem. 129 (2007), 137-147.
Sriwongsitanont, et al. "Physiochemical Properties of PEG-Grafted Liposomes." Chem Pharm Bull; 2002; pp. 1238-1244; vol. 50(9).
Stagno et al., "Cytomegalovirus," In Infectious Diseases of the Fetus and Newborn Infant, 6th edition, JS Remington and JO Klein (ed.), WB Saunders, Philadelphia, PA, 1995, pp. 312-353.
Stedman's Medical Dictionary; 27th Edition; Lippincott, Williams & Wilkins; published 2000, p. 1963.
Strauss, J. H. et al., Microbiological Reviews, 58(3): 491-562 (1994) (excerpt).
Strejan, "Suppression of Chronic-Relapsing Experimental Allergic Encephalomyelitis in Strain-13 Guinea Pigs by Administration of Liposome-Associated Myelin Basic Protein", Journal of Neuroimmunology; vol. 7; 1984; pp. 27-41.
Submission filed by the patentee (then applicant) in the examination proceedings (Jun. 26, 2017).
Sugiyama, T., "Immunoadjuvant effects of polyadenylic:polyuridylic acids through TLR3 and TLR7", Int. Immunolo. 20 (1): 1-9 (2008)—XP002665154.
Szoka, et al., "Procedure for preparation of liposomes with large internal aqueous space and high capture by reverse-phase evaporation," Proc Natl Acad Sci U S A, 75(9) (1978): 4194-4198.
Tannous, et al., Secreted blood reporters: Insights and applications, Biotechnol. Adv., 2011, 29(6):997-1003.
ThermoFisher Scientific, "Ribosomal RNA Sizes", submitted in EP Opposition against Application No. EP 2591103 on Jan. 14, 2022, 1 page.
Third Party Observations under Art. 115 EPC Nov. 3, 2016, from EP Appl. No. 11736499.2; pp. 1-17.
Thompson et al., "Mucosal and systemic adjuvant activity of alphavirus replicon particles," Proceedings of the National Academy of Sciences,103{10):3722-3727 (2006).
Tonkin, D. R. et al., Vaccine, 28(18): 3238-3246 (2010).
Torchilin, et al., "Poly(ethylene glycol) on the liposome surface: on the mechanism of polymer-coated liposome longevity." Biochimica et Biophysica Acta, 1994, vol. 1195, pp. 11-20.
Tranchant, I et al. (2004) J Gene Med 6: S24-S35.
Tubulekas et al., "Alphavirus expression vectors and their use as recombinant vaccines: a minireview" 190 Gene 191-195 (1997).
U S. Appl. No. 17/560,019, filed Dec. 22, 2021.
U.S. Appl. No. 17/511,762, filed Oct. 27, 2021.
U.S. Appl. No. 17/512,258, filed Oct. 27, 2021.
U.S. Appl. No. 17/560,052, filed Dec. 22, 2021.
U.S. Appl. No. 17/560,059, filed Dec. 22, 2021.
U.S. Appl. No. 17/560,092, filed Dec. 22, 2021.
U.S. Appl. No. 17/560,116, filed Dec. 22, 2021.
U.S. Appl. No. 17/560,138, filed Dec. 22, 2021.
U.S. Appl. No. 61/529,878, filed Aug. 31, 2011.
Uddin SN, Biotechnology and Molecular Biology Review 2(3): 058-067, 2007.
Ulmer, et al., "Heterologous Protection Against Influenza by Injection of DNA Encoding a Viral Protein." Science; 1993; pp. 1745-1749; vol. 259.
U.S. Appl. No. 61/505,088.
U.S. Appl. No. 16/714,877, filed Dec. 16, 2019.
U.S. Appl. No. 17/808,519, filed Jun. 23, 2022.
U.S. Appl. No. 17/848,294, filed Jun. 23, 2022.
U.S. Appl. No. 17/848,299, filed Jun. 23, 2022.
U.S. Appl. No. 17/848,337, filed Jun. 23, 2022.
U.S. Appl. No. 61/361,828, filed Jul. 6, 2010.
Van Bleek et al., "RSV 2010: Recent advances in research on respiratory syncytial virus and other pneumoviruses," Vaccine, 29{43):7285-7291 (2011).
Varnum et al., "Identification of proteins in human cytomegalovirus (HCMV) particles: the HCMV proteome," J. Virol., 2004, 78(20):10960-10966.
Vasiljeva et al., "Identification of a novel function of the alphavirus capping apparatus," Journal of Biological Chemistry, 2000; 275(23):17281-17287.

(56) References Cited

OTHER PUBLICATIONS

Vignuzzi, et al., "Naked RNA immunization with replicons derived from poliovirus and Semliki Forest virus genomes for the generation of a cytotoxic T cell response against the influenza A virus nucleoprotein." Journal of General Virology; 2001; pp. 1737-1747; vol. 82(7).
Wang et al., "Human cytomegalovirus virion protein complex required for epithelial and endothelial cell tropism," Proc. Natl. Acad. Sci. USA, 2005, 102(5):18153-18158.
Wang, et al., "pH-sensitive immunoliposomes mediate target-cell-specific delivery and controlled expression of a foreign gene in mouse." Proc. Natl. Acad. Sci. USA; 1987; pp. 7851-7855; vol. 84.
Ward, et al., "Generation of CTL responses using Kunjin replicon RNA" Immunology and Cell Biology; 2003; pp. 73-78; vol. 81(1).
Weide, et al., "Direct Injection of Protamine-protected mRNA: Results of a Phase 1/2 Vaccination Trial in Metastatic Melanoma Patients." Journal of Immunotherapy; 2009; pp. 498-507; vol. 32(5).
Weide, et al., "Results of the First Phase 1111 Clinical Vaccination Trial with Direct Injection of mRNA," Journal of Immunotherapy; 2008; pp. 180-188; vol. 31(2).
Whitehead et al., "Knocking down barriers: advances in siRNA delivery" Nature Reviews Drug Discovery; 2009; pp. 129-138; vol. 8.
Wille et al., "A human cytomegalovirus gO-null mutant fails to incorporate gH/gL into the virion envelope and is unable to enter fibroblasts and epithelial and endothelial cells," J. Virol., 2010, 84(5):2585-2596.
Wilson et al., "Biological properties of poliovirus encapsulated in lipid vesicles: Antibody resistance and infectivity in virus-resistant cells", Proc. Natl. Acad. Sci. USA; 1977; pp. 3471-3475; vol. 74, No. 8.
Wilson, et al., "The Introduction of Poliovirus RNA into Cells via Lipid Vesicles (Liposomes)." Cell, 1979, vol. 17, pp. 77-84.
Wilson, Kaley et al.; "The combination of stabilized plasmid lipid particles and lipid nanoparticle encapsulated CpG containing oligodexoynucleotides as a systemic genetic vaccine", The Journal of Gene Medicine; 11; p. 14-25; 2009.
Wloch, et al., "Safety and Immunogenicity of A Bivalent of CMV DNA Vaccine in Healthy in Healthy Adult Subjects." J Infect Dis; 2008; pp. 1634-1642; vol. 197(12).
Xiong et al., "Sindbis virus: an efficient, broad host range vector for gene expression in animal cells," Science, 243:1188-1191 (1989).
Xu et al., "Characterization of immune Responses Elicited in Macaques Immunized Sequentially with Chimeric VEE/ SIN Alphavirus Replicon Particles Expressing SIVGag and/or HIVEnv and with Recombinant HIVgp140Env Protein," Aids Research and Human Retroviruses, Mary Ann Liebert, 22(10):1022-1030 (2006).
Xu et al., "Sequential priming and boosting with heterologous HIV immunogens predominantly stimulated T cell immunity against conserved epitopes," Aids; 20(18); 2293-2303; Nov. 28, 2006.
Xu, et al., "Clinical Trials and Translational Medicine Commentary: Drug Delivery Trends in Clinical Trials and Translational Medicine: Challenges and Opportunities in the Delivery of Nucleic Acid-Based Therapeutics," Journal of Pharmaceutical Sciences, vol. 100, No. 1, (2011), pp. 38-52.
Xu, Y., et al., Physicochemical characterization and purification of cationic lipoplexes, Biophys J., 1999, 77(1):341-53.
Yang, J-P., et al., "Overcoming the inhibitory effect of serum on lipofection by increasing the charge ratio of cationic liposome to DNA," Gene Therapy, vol. 4, 1997, pp. 950-960; 1997.
Yi, et al., "A Cationic Lipid Emulsion/DNA Complex as a Physically Stable and Serum-Resistant Gene Delivery." Pharmaceutical Research; 2000; pp. 314-320; vol. 17.
Yoder, et al., "Role of Complement in Neutralization of Respiratory Syncytial Virus" J Med Virol., 2004; pp. 688-694; vol. 72.
Yoffe, "Predicting the sizes of large RNA molecules" PNAS; vol. 105; 2008; pp. 16153-16158.
Yoneyama, et al., "RIG-I family RNA helicases: cytoplasmic sensor for antiviral innate immunity," Cytokine & Growth Factor Review S, (2007), vol. 18, pp. 545-551.

Yoon, et al., "DNA-Mediated Immunization of Mice with Plasmid Encoding HBs Antigen." J. Korean Med Sci; 1999; pp. 187-192; vol. 14.
Yu et al., Journal of Pharmaceutical Sciences 98(9): 3278-3289; 2009.
Zhao, QQ., et al., N/P ratio significantly influences the transfection efficiency and cytotoxicity of a polyethylenimine/chitosan/DNA complex, Biol. Pharm. Bull., 2009, 32(4):706-10.
Weissig, Liposomes: Methods and Protocols, vol. 1: Pharmaceutical Nanocarriers: Methods and Protocols, Humana Press, vol. 1.
Zhou, X., et al., "Self-replicating Semliki Forest virus RNA as recombinant vaccine", Vaccine 12(16): 1510-1514 (1994).
Zhu et al. "Vaccines for Gonorrhea: Can We Rise to the Challenge?" Frontiers in Microbiology, vol. 2, Jan. 1, 2011, 13 pages.
Zhu et al., Science, 261: 209-211 (1993).
Zhu L & Mahato RI, Expert Opin Drug Deliv. 7(10): 1209-1226, 2010.
Zimmermann et al., "RNAi-mediated gene silencing in non-human primates," Nature, vol. 441, pp. 111-114 (2006).
Zuckerman, "Principles and Practice of Travel Medicine," 2001, pp. 165-183.
Zuckerman, The importance of injecting vaccines into muscle, BMJ, vol. 321, pp. 1237-1238 (2000).
Patel et al., "The Importance of Apparent pKa in the Development of Nanoparticles Encapsulating siRNA and mRNA," Trends Pharmacol Sci., vol. 42, No. 6, (2021), pp. 448-460.
Eastman et al., "Influence of Phospholipid Asymmetry on Fusion between Large Unilamellar Vesicles," Biochemistry, vol. 31, (1992), pp. 4262-4268.
Declaration by Russell Johnson dated Sep. 21, 2022 in opposition filed in EP2591103, Int'l filing date Jul. 6, 2012, (2 pages).
Hwang et al., "alpha-Methylprednisolone Conjugated Cyclodextrin Polymer-Based Nanoparticles for Rheumatoid Arthritis Therapy," International Journal of Nanomedicine, 2008, 3(3), 359-371.
Bettinger, T., et al., "Recent Developments in RNA-Based strategies for cancer gene therapy", Current Opinion in Molecular Therapeutics, Current Drugs, London, GB, vol. 3, No. 2, Apr. 1, 2001, pp. 116-124.
Van Der Velden, W., et al., "Vector Design for Optimal Protein Expression", Sep. 1, 2001, p. 576.
Geldmacher et al: "Therapeutic vaccination for cancer immunotherapy: Antigen selection and clinical responses", Human Vaccines, vol. 7, No. sup1, Jan. 1, 2011 (Jan. 1, 2011), pp. 115-119.
Pascolo S., "Messenger RNA-based vaccines", Expert Opinion on Biological the, Informa Healthcare, Ashley, London; GB, vol. 4, No. 8, Aug. 1, 2004 (Aug. 1, 2004), pp. 1285-1294.
EP12722942.5 (Moderna's submission of Jul. 9, 2018).
Agris et al., (1999) "Thermodynamic Contribution of Nucleoside Modifications to Yeast tRNAphe Anticodon Stem Loop Analogs," Acta Biochimica Polonica, vol. 46, No. 1, pp. 163-172.
Anderson et al., Nucleic Acids Research (2011), 39(21), 9329, published online on Aug. 3, 2011.
Andries et al., (2015) Sep. 3, 2015 "N(1)-Methylpseudouridine-Incorporated mRNA Outperforms Pseudouridine-Incorporated mRNA by Providing Enhanced Protein Expression and Reduced Immunogenicity in Mammalian Cell Lines and Mice," Journal of Controlled Release, vol. 217, pp. 337-344.
Annex to the communication in Opposition against EP 3 492 109 B1 by the Opposition Division Apr. 13, 2022.
A-Plus™ Poly(A) Polymerase Tailing Kit Protocol Nov. 16, 2006 (Capture Date).
Application underlying the present patent as filed with the application No. EP 18 153 312.6.
Aso and Yoshioka: "Effect of freezing rate on physical stability of lyophilized cationic liposomes", Chem Pharm. Bull. 53(3) 301-204 (2005).
BioRad Product catalog post-published evidence.
Brand et al., Biochem. J. (1978), 169, 71-77.
Chang et al. 2008 Nov. 19, 2007 "Synthesis and Solution Conformation Studies of 3-substituted Uridine and Pseudouridine Derivatives," Bioorganic & Medicinal Chemistry, vol. 16, pp. 2676-2686.
Chatterjee et al., (2012) Mar. 2012 "The Archaeal COG1901/DUF358 SPOUT-Methyltransferase Members, Together with

(56) References Cited

OTHER PUBLICATIONS

Pseudouridine Synthase Pus10, Catalyze the Formation of 1-Methylpseudouridine at Position 54 of tRNA," RNA, vol. 18, pp. 421-433.
Chen et al. "An Overview of Liposome Lyophilization and its Future Potential," Journal of Controlled Release 142 (2010) 299-311.
Christ: "Gefriertrocknung mit System" (with D6a, a timestamp, showing that this document was available as of Jan. 22, 2010).
Christ: "Smart Freeze Drying" Manual Jan. 2010.
Cortesi et al.: Effect of DNA complexation and freeze-drying on the physicochemical characteristics of cationic liposomes, Antisense & Nucleic Acid Drug Development 10:205-215(2000).
CRC Handbook of Chemistry and Physics, 101st Edition, CRC Press 2020—Section 6 vapor pressure of ice.
CV Dr Olatokumbo Ogunleye.
Declaration from Dr Olatokumbo Ogunleye.
Drug Discovery Handbook, edited by Shayne Cox Gad, Wiley Interscience, 2005; Chapter 27: RNA-based therapies, pp. 1259 to 1308.
Earl and Townsend (1977) Jun. 1977 "A Chemical Synthesis of the Nucleoside I-Methylpseudouridine," J. Heterocyclic Chem, vol. 15, pp. 699-700.
Eberhardt et al. "Modulation of mRNA Stability as a Novel Therapeutic Approach," Pharmacology & Therapeutics 114 (2007) 56-73.
Excerpt of textbook "The immune system" by Peter Parham, Third edition, (2009) Cover page, Table contents and pp. 49 and 50 common general knowledge.
F.F. Davis, F.W. Allen (1957) "Ribonucleic Acids from Yeast which Contain a Fifth Nucleotide".
https://www.convertunits.com/from/atmosphere+[standard]/to/mtorr.
Janeway CA Jr, Travers P, Walport M, et al. Immunobiology: The Immune System in Health and Disease. 5th edition. New York: Garland Science; 2001. Induced innate responses to infection. Part I, Chapter 2, "Induced innate responses to infection" pp. 87-106. Available from: https://www.ncbi.nlm.nih.oov/books/NBK27122/.
Jones et al.: "Long-term storage of DNA-free RNA for use in vaccine studies", BioTechniques 43:675-681 (Nov. 2007).
Kariko (2008) "Incorporation of Pseudouridine into mRNA yields Superior Nonimmunogenic Vector with Increased Translational Capacity and Biological Stability," Mol Ther., vol. 16, No. 11, pp. 1833-1840.
Kariko and Weissman, (2007) "Naturally Occurring Nucleoside Modifications Suppress the Immunostimulatory Activity of RNA: Implication for Therapeutic RNA Development," Curr Opin Drug Disc & Dev., vol. 10, No. 5, pp. 524-532.
Kariko et al., (2005) "Suppression of RNA Recognition by Toll-Like Receptors: The Impact of Nucleoside Modification and the Evolutionary Origin of RNA," Immunity, vol. 23, pp. 165-175.
Kariko et al., (2012) "Increased Erythropoiesis in Mice Injected with Submicrogram Quantities of Pseudouridine—Containing mRNA Encoding Erythropoietin," Mal Ther 20(5):948-53.
Kariko et al., Nucleic Acids Research (2011), 39 (21), e142, published online on Sep. 2, 2011.
Kariko, Muramatsu, Welsh, Ludwig, Kato, Akira and Weissman (2008) Incorporation of Pseudouridine Into mRNA Yields Superior Nonimmunogenic Vector With Increased Translational Capacity and Biological Stability. Molecular Therapy vol. 16 No. 11, 1833-1840.
Kierzek & Kierzek et al., (2001) Jun. 21, 2001 "Influence of N6-Isopentenyladenosine (k6A) on Thermal Stability of RNA Duplexes," Biophysical Chemistry, vol. 91, pp. 135-140.
Molina et al.: The stability of lyophilized lipid/DNA complexes during prolonged storage, Journal of Pharmaceutical Sciences, vol. 93, No. 9, Sep. 2004.
Montana et al. "Employment of Cationic Solid-Lipid Nanoparticles as RNA Carriers," Bioconjugate Chem. 2007, 18, 302-308.
Motorin & Helm (2009) Dec. 8, 2009 "RNA Nucleotide Methylation," Advanced Review, vol. 2, pp. 611-631.
Motorin & Helm (2011) Sep./Oct. 2011 "5-Methylcytosine in RNA: Detection, Enzymatic Formation and Biological Functions," Nucleic Acids Research, vol. 38, No. 5, pp. 1415-1430.
MRNA-Only™ Prokaryotic mRNA Poly(A)-Tailing.
Kit Protocol Nov. 16, 2006 (Capture Date).
Nucleic Acids in Innate Immunity, Various Authors (2008) CRC Press.
Operating manual freeze-dryer Alpha 1-4 LCS plus and Alpha 2-4 LSC plus by Christ, revised version of Dec. 16, 2013.
Pang et al., (1982) Apr. 1982 "Structure of a Modified Nucleoside in Archaebacterial tRNA which Replaces Ribosylthymine," The Journal of Biological Chemistry, vol. 257, No. 7, pp. 3589-3592.
Parent application PCT/US2012/041663 in the form as published as WO 2012/170889 A1.
Post-filed evidence submitted on Jun. 12, 2014 during prosecution of EP2578685 B1 (D1a).
Post-filing experimental evidence submitted by the Patentee during the examination phase of EP 18 153 312.6 on Apr. 5, 2019.
Reichman et al., (1977) Feb. 1977 The Journal of Antibiotics, vol. XXX, No. 2, pp. 129-131.
Reijenga et al., "Development of Methods for the Determination of pKa Values," Analytical Chemistry Insights, vol. 8, (2013), pp. 53-71.
Robbins et al., (2007) Sep. 1, 2007 "2'-O-Methyl-Modified RNAs Act as TLR7 Antagonists," Mol. Ther. vol. 15, No. 9, pp. 1663-1669.
Sahin et al., Nature Reviews Drug Discovery (2014), 13, 759-780, published online on Sep. 19, 2014.
Schlake et al., "Developing mRNA-Vaccine Technologies," RNA Biology (2012), 9 (11), 1319-1330, published in Nov. 2012.
Size Homogeneity of a Liposome Preparation is Crucial for Liposome Biodistribution in Vivo.
D. Liu and L. Huang Journal of Liposome Research 2(1): 57-66 (1992).
Su et al In Vitro and in Vivo mRNA Delivery using Lipid-Enveloped pH-Responsive Polymer Nanoparticles, Molecular Pharmaceutics, vol. 8, (2011) pp. 774-787.
Submitted claims to the EPO on Sep. 30, 2008 in the case EP 06 81 3536.7 (EP1979364) prior art under Art. 54(2) EPC.
Tang et al. "Design of Freeze-Drying Processes for Pharmaceuticals: Practical Advice," Pharmaceutical Research, vol. 21, No. 2, Feb. 2004.
Tcherepanova et al, "Ectopic Expression of a Truncated CD40L Protein from Synthetic Post-Transcriptionally Capped RNA in Dendritic Cells Induces High Levels of IL-I2 Secretion," BMC Molecular Biology 2008, 9:90.
The International Association for the Properties of Water and Steam, Pizer\ Czech Republic, Sep. 2011.
U.S. Appl. No. 61/494,745, filed Jun. 8, 2011.
U.S. Appl. No. 61/494,882, filed Jun. 8, 2011.
Van Winden EC, "Freeze-drying of liposomes: theory and practice "Methods Enzymol. 2003; 367:99-110.
VirTis Advantage Plus marketing brochure 2008.
VirTis Advantage Plus specification sheet 2013.
Weissman et al., "HIV Gag mRNA Transfection of Dendritic Cells (DC) Delivers Encoded Antigen to MHC Class I and II Molecules, Causes DC Maturation, and Induces a Potent Human in Vitro Primary Immune Response," The Journal of Immunology, 2000, 165 (8), 4710, published on Oct. 15, 2000.
Wisse et al. 2008 "The Size of Endothelial Fenestrae in Human Liver Sinusoids: Implications for Hepatocyte-Directed Gene Transfer," Gene Therapy, vol. 15, pp. 1193-1199.
Yadava et al., Effect of lyophilization and freeze-thawing on the stability of siRNA-liposome complexes. AAPS Pharm Sci Tech, vol. 9. No. 2, Jun. 2008.
Yarian et al., (1999) Sep. 1, 1999 "Structural and Functional Roles of the N1- and N3-Protons of Ψ at tRNA's Position 39," Nucleic Acids Research, vol. 27, No. 17, pp. 3542-3549.
Zust et al., (2011) Feb. 2011 "Ribose 2'-O-Methylation Provides a Molecular Signature for the Distinction of Self and Non-self mRNA Dependent on the RNA Sensor Mda5," Nature Immunology, vol. 12, No. 2, pp. 137-144.
U.S. Appl. No. 61/404,413, filed Oct. 1, 2010.

(56) References Cited

OTHER PUBLICATIONS

U.S. Appl. No. 61/542,533, filed Oct. 2, 2011.
U.S. Appl. No. 61/570,690, filed Dec. 14, 2011.
U.S. Appl. No. 61/576,705, filed Dec. 16, 2011.
U.S. Appl. No. 61/578,271, filed Dec. 21, 2011.
U.S. Appl. No. 61/618,862, filed Apr. 2, 2012.
Mann et al., "DNA Transfer into Vascular Smooth Muscle using Fusigenic Sendai Virus (HJV)-Liposomes," Molecular and Cellular Biochemistry, vol. 172, (1997), pp. 3-12.
Kitajima et al., "Efficient Transfer of Synthetic Ribozymes into Cells using Hemagglutinating Virus of Japan (HVJ)-Cationic Liposomes," The Jounral of Biological Chemistry, vol. 272, No. 43, (1997), pp. 27099-27106.
Willis et al., "Liposome-Anchored Vascular Endothelial Growth Factor Aptamers," Bioconjugate Chem., vol. 9, (1998), pp. 573-582.
Bai et al., "Gene Transfer to Vein Graft Wall by HVJ-Liposome Method: Time Course and Localization fo Gene Expression," Ann Thorac Surg, vol. 66, (1998), pp. 814-820.
Mandal et al., "Delivery of Macromolecules into Cytosol using Liposomes Containing Hemolysin," Methods in Enzymology, vol. 372, (2003), pp. 319-339.
Kawauchi et al., "Gene Therapy for Attenuating Cardiac Allograft Arteriopathy using Ex Vivo E2F Decoy Transfection by HVJ-AVE-Liposome Method in Mice and Nonhuman Primates," Circulation Research, (2000), pp. 1063-1068.
Hobo et al., "Improving Dendritic Cell Vaccine Immunogenicity by Silencing PD-1 Ligands using siRNA-lipid Nanoparticles Combined with Antigen mRNA Electroporation," Cancer Immunol Immunother, vol. 62, (2013), pp. 285-297.
Hobo et al., "Immunogenicity of Dendritic Cells Pulsed with MAGE3, Survivin and B-Cell Maturation Antigen mRNA for Vaccination of Multiple Myeloma Patients," Cancer Immunol Immunother, vol. 62, (2013), pp. 1381-1392.
Kreiter et al., "Tumor Vaccination using Messenger RNA: Prospects of a Future Therapy," Current Opinion in Immunology, vol. 23, (2011), pp. 399-406.
Zimmer et al., "RNA Replicons—A New Approach for Influenza Virus Immunoprophylaxis," Viruses, vol. 2, (2010), pp. 413-434.
Dwarki et al., "Cationic Liposome-Mediated RNA Transfection," Methods in Enzymology, vol. 217, (1993), pp. 644-654.
Leroueil PR, et al., "Wide varieties of cationic nanoparticles induce defects in supported lipid bilayers" Nano Lett. Feb. 2008;8(2):420-4. Epub Jan. 25, 2008. (Year: 2008).
Szebeni J, et. al., "Activation of complement by therapeutic liposomes and other lipid excipient-based therapeutic products: prediction and prevention," Adv Drug Deliv Rev. Sep. 16, 2011;63(12):1020-30. Epub Jul. 14, 2011. (Year: 2011).
Szebeni J., "Complement activation-related pseudoallergy: a stress reaction in blood triggered by nanomedicines and biolocials," Mol Immunol. Oct. 2014;61(2):163-73. Epub Aug. 12, 2014. (Year: 2014).
Bahl K, Senn JJ, Yuzhakov 0, Bulychev A, Brito LA, Hassett KJ, Laska ME, et. al. "Preclinical and Clinical Demonstration of Immunogenicity by mRNA Vaccines against H10N8 and H7N9 Influenza Viruses," Mol Ther. Jun. 7, 2017;25(6):1316-1327. Epub Apr. 27, 2017. Erratum in: Mol Ther. Aug. 3, 2022;30(8):2874. (Year: 2017).
Szebeni J, Storm G. "Complement activation as a bioequivalence issue relevant to the development of generic liposomes and other nanoparticulate drugs," Biochem Biophys Res Commun. Dec. 18, 2015;468(3):490-7. doi: 10.1016/j.bbrc.2015.06.177. Epub Jul. 14, 2015. PMID: 26182876. (Year: 2015).
Ernsting MJ, Murakami M, Roy A, Li SD. "Factors controlling the pharmacokinetics, biodistribution and intratumoral penetration of nanoparticles," J Control Release. Dec. 28, 2013;172(3):782-94. doi: 10.1016/j.jconrel.2013.09.013. Epub Sep. 25, 2013. PMID: 24075927; PMCID: PMC3891171. (Year: 2013).
Chen S, Tam YYC, Lin PJC, Sung MMH, Tam YK, Cullis PR. "Influence of particle size on the in vivo potency of lipid nanoparticle formulations of siRNA," J Control Release. Aug. 10, 2016;235:236-244. doi: 10.1016/j.jconrel.2016.05.059. Epub May 26, 2016. PMID: 27238441. (Year: 2016).
Xue HY, Guo P, Wen WC, Wong HL. "Lipid-Based Nanocarriers for RNA Delivery," Curr Pharm Des. 2015;21(22):3140-7. doi: 10.2174/1381612821666150531164540. PMID: 26027572; PMCID: PMC4618487. (Year: 2015).
Hassett KJ, Benenato KE, Jacquinet E, Lee A, Woods A, Yuzhakov 0, Himansu S, Deterling J, Geilich BM, Ketova T, Mihai C, Lynn A, McFadyen I, et al., "Optimization of Lipid Nanoparticles for Intramuscular Administration of mRNA Vaccines," Mol Ther Nucleic Acids. Apr. 15, 2019;15:1-11. Epub Feb. 7, 2019. (Year: 2019).
Poveda C, Biter AB, Bottazzi ME, Strych U. "Establishing Preferred Product Characterization for the Evaluation of RNA Vaccine Antigens," Vaccines (Basel). Sep. 27, 2019;7(4):131. doi: 10.3390/vaccines7040131. PMID: 31569760; PMCID: PMC6963847. (Year: 2019).
Durbin AF, Wang C, Marcotrigiano J, Gehrke L. "RNAs Containing Modified Nucleotides Fail To Trigger RIG-I Conformational Changes for Innate Immune Signaling," mBio. Sep. 20, 2016;7(5):e00833-16. doi: 10.1128/mBio.00833-16. PMID: 27651356; PMCID: PMC5030355. (Year: 2016).
Woodward M, Marko A, Galea S, Eagel B, Straus W, "Varicella Virus Vaccine Live: A 22-Year Review of Postmarketing Safety Data," Open Forum Infect Dis. Aug. 1, 2019;6(8):ofz295. doi: 10.1093/ofid/ofz295. PMID: 31392326; PMCID: PMC6685817. (Year: 2019).
Depledge DP, Yamanishi K, Gomi Y, Gershon AA, Breuer J. "Deep Sequencing of Distinct Preparations of the Live Attenuated Varicella-Zoster Virus Vaccine Reveals a Conserved Core of Attenuating Single-Nucleotide Polymorphisms," J Viral. Sep. 12, 2016;90 (19):8698-704. (Year: 2016).
Shah RA, Limmer AL, Nwannunu CE, Patel RR, Mui UN, Tyring SK. "Shingrix for Herpes Zoster: A Review," Skin Therapy Lett. Jul. 2019;24(4):5-7. PMID: 31339679. (Year: 2019).
Freer G, Pistello M. "Varicella-zoster virus infection: natural history, clinical manifestations, immunity and current and future vaccination strategies," New Microbial. Apr. 2018;41(2):95-105. Epub Mar. 2, 2018. PMID: 29498740. (Year: 2018).
Monslow MA, Elbashir S, Sullivan NL, Thiriot DS, Ahl P, Smith J, et. al. "Immunogenicity generated by mRNA vaccine encoding VZV gE antigen is comparable to adjuvanted subunit vaccine and better than live attenuated vaccine in nonhuman primates," Vaccine. Aug. 10, 2020;38(36):5793-5802. Epub Jul. 20, 2020. (Year: 2020).
Office Action issued in U.S. Appl. No. 17/560,052, dated Jul. 12, 2022.
Office Action issued in U.S. Appl. No. 17/560,138, dated Aug. 23, 2022.
Office Action issued in U.S. Appl. No. 17/560,092, dated Aug. 4, 2022.
Office Action issued in U.S. Appl. No. 17/560,059, dated Jul. 15, 2022.
Office Action issued in U.S. Appl. No. 17/696,143, dated Aug. 30, 2022.
Office Action issued in U.S. Appl. No. 17/511,762, dated Sep. 15, 2022.
Office Action issued in U.S. Appl. No. 16/837,115, dated Apr. 22, 2022.
Office Action issued in U.S. Appl. No. 16/714,891, dated May 26, 2022.
McGown, "UV Absorbance Measurements of DNA in Microplates," BioTechniques, vol. 28, (2000), pp. 60-64.
Office Action, dated Nov. 23, 2022, in U.S. Appl. No. 17/560,019.
Office Action, dated Nov. 23, 2022, in U.S. Appl. No. 17/560,052.
Office Action, dated Nov. 25, 2022, in U.S. Appl. No. 17/560,059.
Office Action, dated Dec. 8, 2022, in U.S. Appl. No. 17/560,116.
Felgner et al., "Cationic Lipid-Mediated Transfection in Mammalian Cells: Lipofection," J Tiss Cult Meth., vol. 15, (1993), pp. 63-38.
Akinc et al., "The Onpattro Story and the Clinical Translation of Nanomedicines Containing Nucleic Acid-Based Drugs," Nature Nanotechnology, vol. 14, (2019), pp. 1084-1087.

(56) References Cited

OTHER PUBLICATIONS

Ambegia et al., "Stabilized Plasmid-Lipid Particles Containing PEG-diacylglycerols Exhibit Extended Circulation Lifetimes and Tumor Selective Gene Expression," Biochimica et Piophysica Acta., vol. 1669, (2005), pp. 155-163.
Banerjee, "5'Terminal Cap Structure in Eucaryotic Messenger Ribonucleic Acids," Microbiological Reviews, vol. 44, No. 2, (1980), pp. 175-205.
Declaration of Kimberly J. Hassett, dated Nov. 18, 2021.
Cox et al., "Plasmid DNA and Messenger RNA for Therapy," Handbook of Pharmaceutical Biotechnology, Chapter 7.2, (2007), pp. 971-1011.
Bangs et al., "Mass Spectrometry of mRNA Cap 4 from Trypanosomatids Reveals Two Novel Nucleosides, The Journal of Biological Chemistry," vol. 267, No. 14, (1992), pp. 9805-9815.
Excerpt from Moderna's 2018 10-K.
Pascolo, "Vaccination with Messenger RNA (mRNA)," Handboook of Experimental Pharmacology, vol. 183, (2008), pp. 221-235.
Furuichi et al., "Viral and Cellular mRNA Capping: Past and Prospects," Advances in Virus Research, vol. 55, (2000), pp. 135-184.
Fechter et al., "Recognition of mRNA Cap Structures by Viral and Cellular Proteins," Journal fo General Virology, vol. 86, (2005), pp. 1239-1249.
Pardi et al., "Nucleoside-Modified mRNA Vaccines Induce Potent T Follicular Helper and Germinal Center B Cell Responses," Journal of Experimental Medicine, vol. 215, No. 6, (2018), pp. 1571-1588.
Morais et al., "The Critical Contribution of Pseudouridine to mRNA COVID-19 Vaccines," Frontiers in Cell and Development Biology, vol. 9, (2021), pp. 1-9.
Hess et al., "Vaccination with mRNAs encoding Tumor-Associated Antigens and Granulocyte-Macrophage Colony-Stimulating Factor Efficiently Primes CTL Responses, but is Insufficient to Overcome Tolerance to a Model Tumor/Self Antigen,," Cancer Immunol Immunother, vol. 55, (2006), pp. 672-683.
Lambert et al., "Intradermal Vaccine Delivery: Will New Delivery Systems Transform Vaccine Administration?" Vaccine, vol. 26, (2008), pp. 3197-3208.
Li et al., Low-pH-Sensitive Poly(ethylene glycol) (PEG)-Stabilized Plasmid Nanolipoparticles: Effects of PEG Chain Length, Lipid Composition and Assembly Conditions on Gene Delivery, The Journal of Gene Medicine, vol. 7, (2005), pp. 67-79.
Patentee Submission to EPO in EP Application No. 11758014.2, dated Nov. 13, 2018.
Roos, "Europe Approves Sanofi's Intradermal Flu Vaccine," University of Minnesota Center for Infections Disease Research and Policy [online: cidrap.umn.edu/news-perspective/2009/02/europe-approves-sanofis-intradermal-flu-vaccine], (2009), pp. 1-2.
"ProductInfoNow," Modern Drug Discovery, vol. 6, No. 6, (2003), pp. 57-62.
Print-out of the entry for the m7G(5')ppp(5')G RNA Cap Structure Analog from the New England Biolabs homepage, from Apr. 2010, pp. 1-2.
Print-out of the entry for the ScriptCap™ m7G Capping System from the Epicentre Biotechnologies homepage from Nov. 2006, pp. 1-2.
Santos et al., "Design of Peptide-Targeted Liposomes Containing Nucleic Acids," Biochimica et Biophysica Acta, vol. 1798, (2010), pp. 433-441.
Spikevax Patient Information, European Medicines Agency, (2022), pp. 1-5.
Sticchi et al., "The Intradermal Vaccination: Past Experiences and Current Perspectives," J Prev Med Hyg, vol. 51, (2010), pp. 7-14.
Van den Berg et al., "Shielding the Cationic Charge of Nanoparticle-Formulated Dermal DNA Vaccines is Essential for Antigen Expression and Immunogenicity," Journal of Controlled Release, vol. 141, (2010), pp. 234-240.
Sonoke et al., "Tumor Regression in Mice by Delivery of Liposomes," Cancer Research, vol. 68, (2008), pp. 8843-8851.
Kim et al., "Enhanced siRNA Delivery using Cationic Liposomes with new Polyarginine-Conjugated PEG-Lipid," International Journal of Pharmaceutics, vol. 392, (2010), pp. 141-147.
Office Action, dated Dec. 21, 2022, issued in U.S. Appl. No. 16/656,929.
Office Action, dated Jan. 20, 2023, issued in U.S. Appl. No. 17/512,258.
Office Action, dated Jan. 24, 2023, issued in U.S. Appl. No. 17/696,143.

\* cited by examiner

FIG. 3
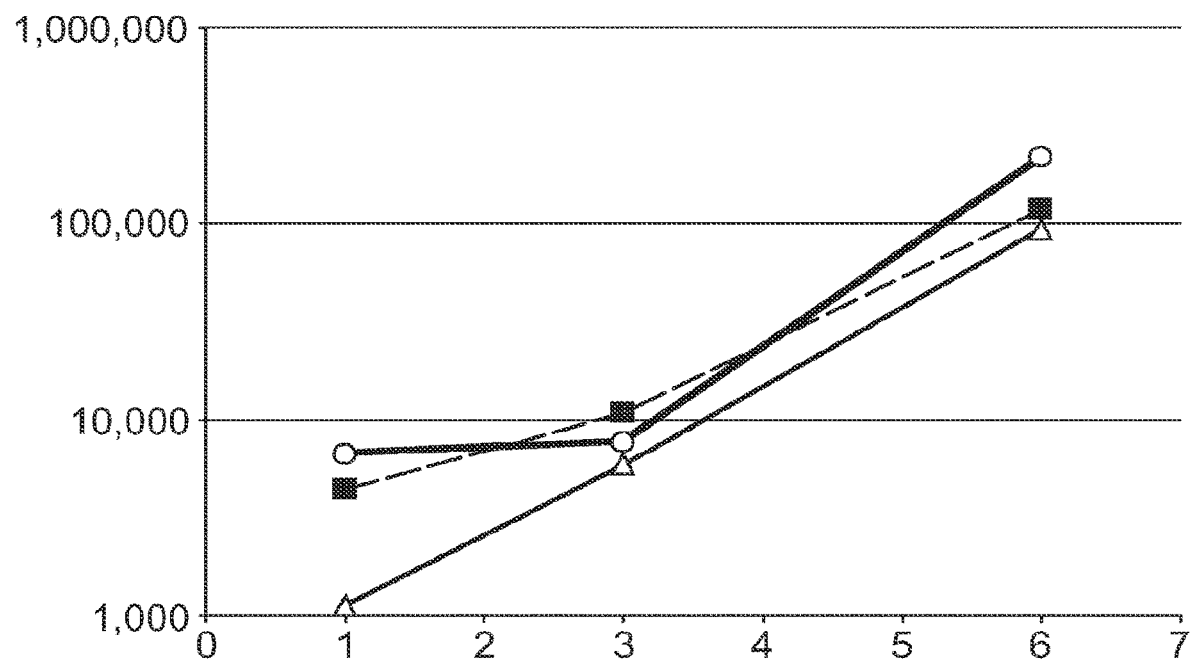
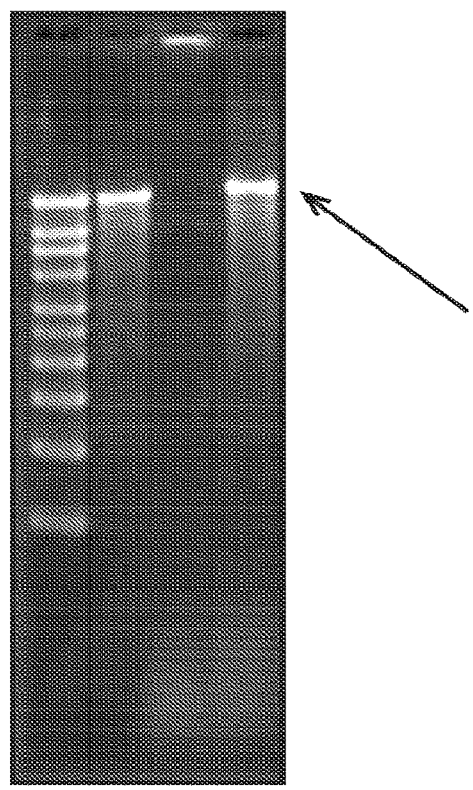
FIG. 4

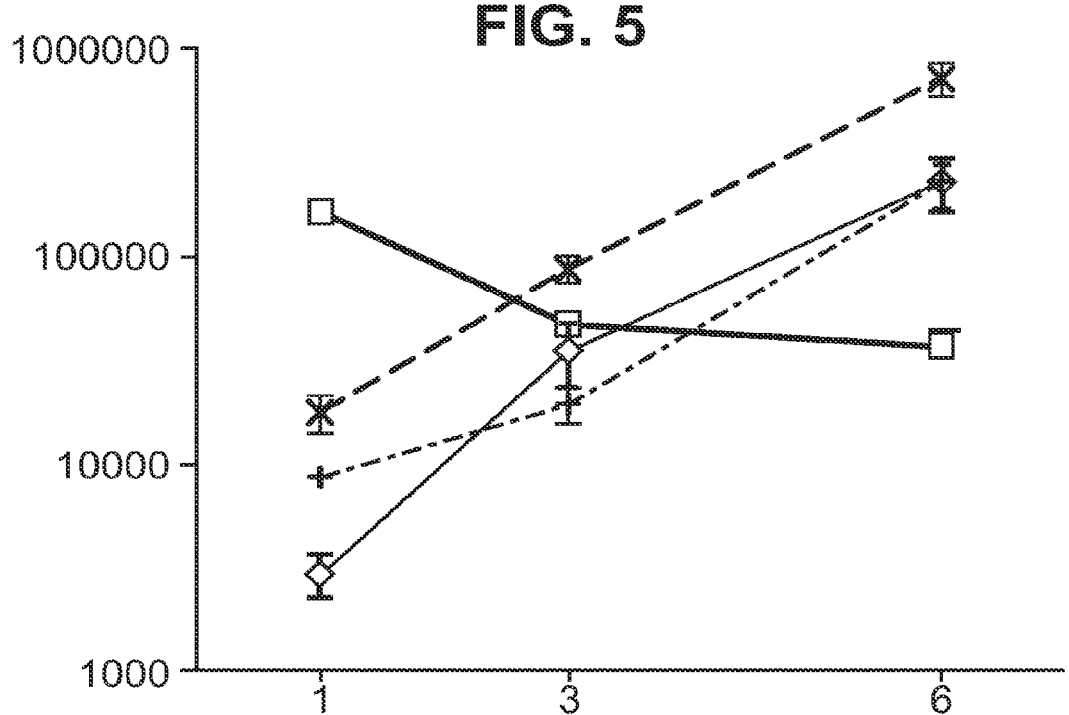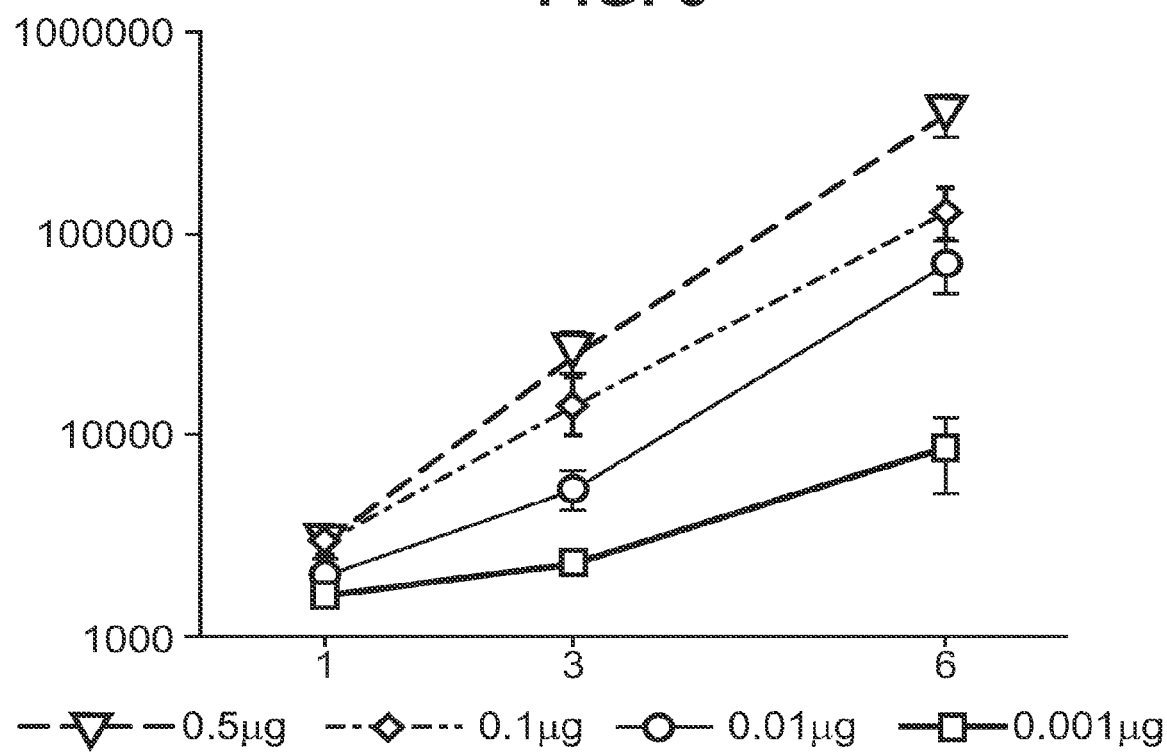

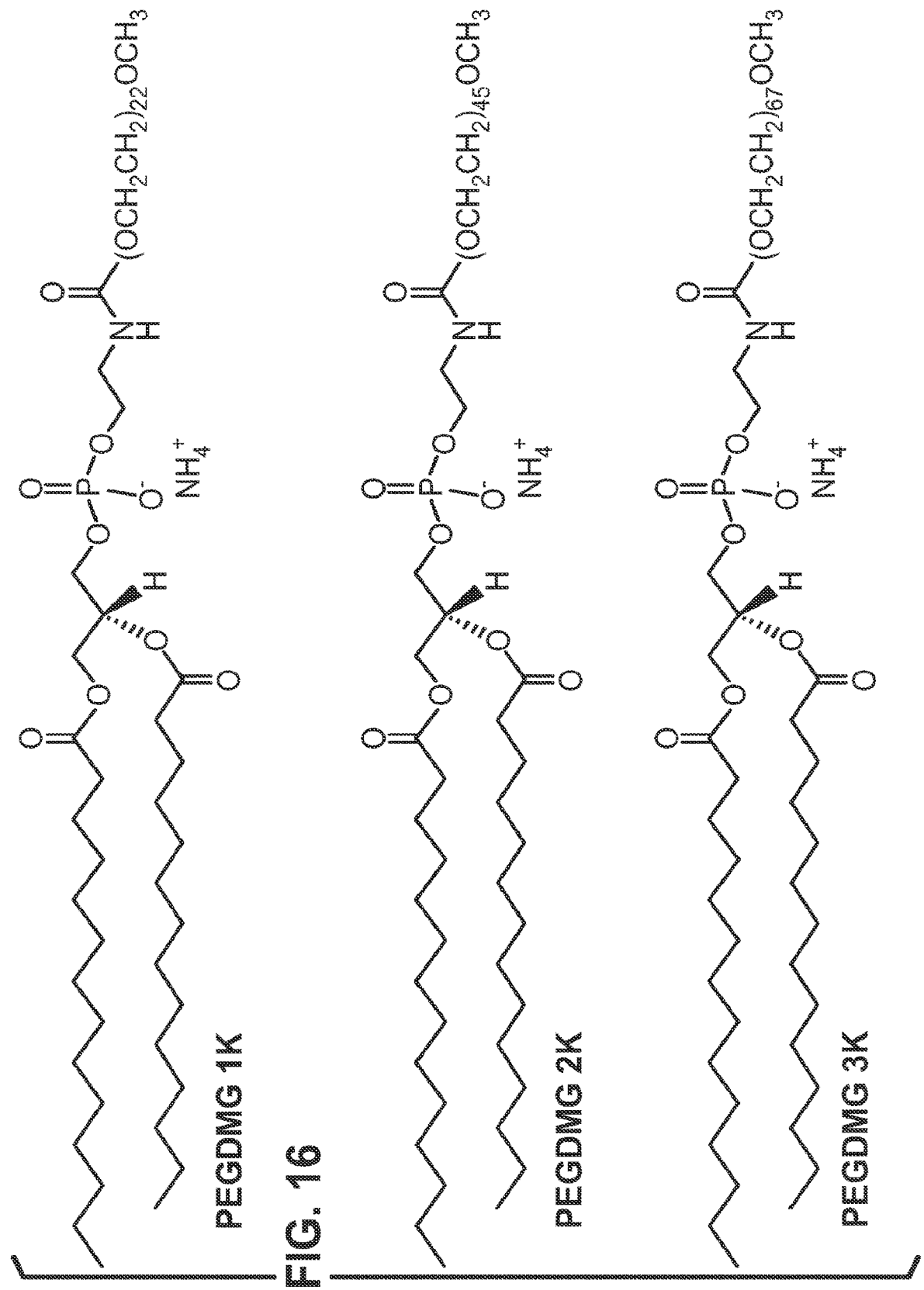

PEGYLATED LIPOSOMES FOR DELIVERY OF IMMUNOGEN-ENCODING RNA

This application is a continuation of U.S. Ser. No. 13/819,077 filed Apr. 16, 2013, which was filed pursuant to 35 U.S.C. § 371 as a United States National Phase Application of International Application No. PCT/US2011/050095 filed Aug. 31, 2011, which claims the benefit of U.S. provisional application No. 61/378,826, which was filed Aug. 31, 2010, the complete contents of which are hereby incorporated herein by reference for all purposes.

TECHNICAL FIELD

This invention is in the field of non-viral delivery of RNA for immunisation.

BACKGROUND ART

The delivery of nucleic acids for immunising animals has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

There remains a need for further and improved nucleic acid vaccines and, in particular, for improved ways of delivering nucleic acid vaccines.

DISCLOSURE OF THE INVENTION

According to the invention, nucleic acid immunisation is achieved by delivering RNA encapsulated within a liposome. The RNA encodes an immunogen of interest. The liposome includes a PEGylated lipid i.e. the lipid is modified by covalent attachment of a polyethylene glycol. PEG provides the liposomes with a coat which can confer favourable pharmacokinetic characteristics e.g. it can increase stability and prevent non-specific adsorption of the liposomes. The inventors have found that the length of the PEG can affect in vivo expression of encapsulated RNA and so the invention uses liposomes which comprise PEG which has an average molecular mass of between 1 kDa and 3 kDa. PEG with a lower molecular weight (e.g. 500 or 750 Da) does not form stable liposomes.

Thus the invention provides a liposome within which RNA encoding an immunogen of interest is encapsulated, wherein the liposome comprises at least one lipid which includes a polyethylene glycol moiety, such that polyethylene glycol is present on the liposome's exterior, wherein the average molecular mass of the polyethylene glycol is between 1 kDa and 3 kDa. These liposomes are suitable for in vivo delivery of the RNA to a vertebrate cell and so they are useful as components in pharmaceutical compositions for immunising subjects against various diseases.

The invention also provides a process for preparing a RNA-containing liposome, comprising a step of mixing RNA with one or more lipids, under conditions such that the lipids form a liposome in which the RNA is encapsulated, wherein at least one lipid includes a polyethylene glycol moiety which becomes located on the liposome's exterior during the process, and wherein the average molecular mass of the polyethylene glycol is between 1 kDa and 3 kDa.

The Liposome

The invention utilises liposomes within which immunogen-encoding RNA is encapsulated. Thus the RNA is (as in a natural virus) separated from any external medium. Encapsulation within the liposome has been found to protect RNA from RNase digestion. The liposomes can include some external RNA (e.g. on their surface), but at least half of the RNA (and ideally all of it) is encapsulated in the liposome's core. Encapsulation within liposomes is distinct from, for instance, the lipid/RNA complexes disclosed in reference 1, where RNA is mixed with pre-formed liposomes.

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic and others are cationic. Suitable classes of phospholipid include, but are not limited to, phosphatidylethanolamines, phosphatidylcholines, phosphatidylserines, and phosphatidyl-glycerols, and some useful phospholipids are listed in Table 1. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC, DSPC, dodecylphosphocholine, 1,2-dioleoyl-sn-glycero-3-phosphatidylethanolamine (DOPE), and 1,2-diphytanoyl-sn-glycero-3-phosphoethanolamine (DPyPE). The lipids can be saturated or unsaturated. The use of at least one unsaturated lipid for preparing liposomes is preferred. If an unsaturated lipid has two tails, both tails can be unsaturated, or it can have one saturated tail and one unsaturated tail. A lipid can include a steroid group in one tail e.g. as in RV05.

Thus in one embodiment the invention provides a liposome having a lipid bilayer encapsulating an aqueous core, wherein: (i) the lipid bilayer comprises at least one lipid which includes a polyethylene glycol moiety, such that polyethylene glycol is present on the liposome's exterior, wherein the average molecular mass of the polyethylene glycol is between 1 kDa and 3 kDa; and (ii) the aqueous core includes a RNA which encodes an immunogen.

Liposomes of the invention can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMG (anionic, saturated). Where a mixture of lipids is used, not all of the component lipids in the mixture need to be amphiphilic e.g. one or more amphiphilic lipids can be mixed with cholesterol.

Where a liposome of the invention is formed from a mixture of lipids, it is preferred that the proportion of those lipids which are PEGylated as described herein is less than 10% of the total amount of lipids e.g. between 0.5-5%, between 1-4%, or about 2%. For instance, useful liposomes are shown below in which 2% of the total lipid is a PEG-DMG. The remainder can be made of e.g. cholesterol (e.g. 35-50% cholesterol) and/or cationic lipid (e.g. 30-70%)

and/or DSPC (e.g. 5-15%). Such mixtures are used below. These percentage values are mole percentages.

Thus a liposome can be formed from a cationic lipid (e.g. DlinDMA, RV05), a zwitterionic lipid (e.g. DSPC, DPyPE), a cholesterol, and a PEGylated lipid. A mixture of DSPC, DlinDMA, PEG-DMG and cholesterol is used in the examples, as well as several further mixtures.

At least one lipid within the liposome includes a polyethylene glycol moiety. Liposomes which include these PEGylated lipids will have PEG oriented so that it is present on at least the exterior of the liposome (but some PEG may also be exposed to the liposome's interior i.e. to the aqueous core). This orientation can be achieved by attaching the PEG to an appropriate part of the lipid. For instance, in an amphiphilic lipid the PEG would be attached to the hydrophilic head, as it is this head which orients itself to the lipid bilayer's aqueous-facing exterior. PEGylation in this way can be achieved by covalent attachment of a PEG to a lipid e.g. using techniques such as those disclosed in reference 2 and 3.

Thus the PEGylated lipids will comprise the PEG structure:

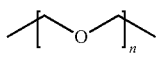

where n provides a molecular weight for the PEG of between 1 kDa and 3 kDa e.g. between 23 and 68, or about 45 for a 2 kDa PEGylation (e.g. see FIG. 16).

The PEG moiety can terminate with an —O-methyl group, and so a PEGylated lipid may comprise:

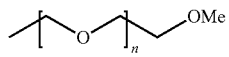

Including attachment to a nitrogen in a lipid's head group, therefore, a PEGylated lipid useful with the invention may comprise:

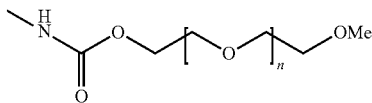

One suitable PEGylated lipid for use with the invention is PEG-DMG, as used in the examples. FIGS. 17A to 17E show further useful PEGylated lipids. PEGylated cholesterol can also be used. Other PEGylated lipids can be used e.g. lipids of Formula (X):

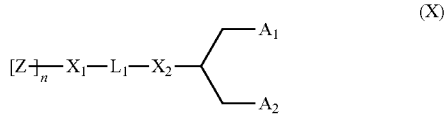

wherein:
Z is a hydrophilic head group component selected from PEG and polymers based on poly(oxazoline), poly (ethylene oxide), poly(vinyl alcohol), poly(glycerol), poly(N-vinylpyrrolidone), poly[N-(2-hydroxypropyl) methacrylamide] and poly(amino acid)s, wherein the polymer may be linear or branched, and wherein the polymer may be optionally substituted;

Z is polymerized by n subunits;

n is a number-averaged degree of polymerization between 10 and 200 units of Z (and can be optimized for different Z groups);

$L_1$ is an optionally substituted $C_{1-10}$ alkylene or $C_{1-10}$ heteroalkylene linker including zero, one or two of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—), wherein R' is independently selected from —H, —NH—, —NH$_2$, —O—, —S—, a phosphate or an optionally substituted $C_{1-10}$ alkylene;

$X_1$ and $X_2$ are independently selected from a carbon or a heteroatom selected from —NH—, —O—, —S— or a phosphate;

$A_1$ and $A_2$ are either independently selected from a $C_{6-30}$ alkyl, $C_{6-30}$ alkenyl, and $C_{6-30}$ alkynyl, wherein $A_1$ and $A_2$ may be the same or different, or $A_1$ and $A_2$ together with the carbon atom to which they are attached form an optionally substituted steroid.

A liposome of the invention will typically include a large number of PEG moieties, which may be the same or different. The average molecular mass of the PEG in a liposome of the invention is between 1 kDa and 3 kDa e.g. between 1.5-2.5 kDa, between 1.7-2.3 kDa, between 1.8-2.2 kDa, between 1.9-2.1 kDa, or 2 kDa. Thus the PEG can be a PEG which is commonly known as "PEG 2000" or "PEG 2k", although the shorter "PEG 1000" and longer "PEG 3000" can also be used.

The PEG will usually comprise linear polymer chains but, in some embodiments, the PEG may comprise branched polymer chains.

It is also possible for a single lipid molecule to include more than one PEG group e.g. attached to different carbon atoms in a lipid's head group (e.g. see FIG. 18). In these circumstances the reference to the molecular mass of PEG in a liposome is the molecular mass per lipid molecule rather than per PEG substituent. Thus, in a liposome in which the sole PEGylated lipid has the structure shown in FIG. 18, where the boxed molecular weight is 2 kDa and is made up of two chains of 1 kDa each, the average molecular mass of the PEG is 2 kDa not 1 kDa.

In some embodiments the PEG may be a substituted PEG e.g. in which one or more carbon atoms in the polymer is substituted by one or more alkyl, alkoxy, acyl or aryl groups.

In some embodiments the PEG may include copolymer groups e.g. one or more propylene monomers, to form a PEG polypropylene polymer.

As an alternative to PEGylation, a lipid may be modified by covalent attachment of a moiety different from PEG. For instance, in some embodiments a lipid may include a polyphosphazene. In some embodiments a lipid may include a poly(vinyl pyrrolidone). In some embodiments a lipid may include a poly(acryl amide). In some embodiments a lipid may include a poly(2-methyl-2-oxazoline). In some embodiments a lipid may include a poly(2-ethyl-2-oxazoline). In some embodiments a lipid may include a phosphatidyl polyglycerol. In some embodiments a lipid may include a poly[N-(2-hydroxypropyl) methacrylamide]. In some embodiments a lipid may include a polyalkylene ether polymer, other than PEG.

Liposomes are usually divided into three groups: multi-lamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes of the invention are ideally LUVs with a diameter in the range of 60-180 nm, and preferably in the range of 80-160 nm.

A liposome of the invention can be part of a composition comprising a plurality of liposomes, and the liposomes within the plurality can have a range of diameters. For a composition comprising a population of liposomes with different diameters: (i) at least 80% by number of the liposomes should have diameters in the range of 60-180 nm, and preferably in the range of 80-160 nm, and/or (ii) the average diameter (by intensity e.g. Z-average) of the population is ideally in the range of 60-180 nm, and preferably in the range of 80-160 nm. The diameters within the plurality should ideally have a polydispersity index <0.2. The liposome/RNA complexes of reference 1 are expected to have a diameter in the range of 600-800 nm and to have a high polydispersity.

Techniques for preparing suitable liposomes are well known in the art e.g. see references 4 to 6. One useful method is described in reference 7 and involves mixing (i) an ethanolic solution of the lipids (ii) an aqueous solution of the nucleic acid and (iii) buffer, followed by mixing, equilibration, dilution and purification. Preferred liposomes of the invention are obtainable by this mixing process. To obtain liposomes with the desired diameter(s), mixing can be performed using a process in which two feed streams of aqueous RNA solution are combined in a single mixing zone with one stream of an ethanolic lipid solution, all at the same flow rate e.g. in a microfluidic channel as described below.

The RNA

Liposomes of the invention include a RNA molecule which (unlike siRNA, as in reference 2) encodes an immunogen. After in vivo administration of the particles, RNA is released from the particles and is translated inside a cell to provide the immunogen in situ.

The RNA is +-stranded, and so it can be translated by cells without needing any intervening replication steps such as reverse transcription. It can also bind to TLR7 receptors expressed by immune cells, thereby initiating an adjuvant effect.

Preferred +-stranded RNAs are self-replicating. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is a huge amplification in the number of the introduced replicon RNAs and so the encoded immunogen becomes a major polypeptide product of the cells.

One suitable system for achieving self-replication is to use an alphavirus-based RNA replicon. These +-stranded replicons are translated after delivery to a cell to give of a replicase (or replicase-transcriptase). The replicase is translated as a polyprotein which auto-cleaves to provide a replication complex which creates genomic --strand copies of the +-strand delivered RNA. These --strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a Sindbis virus, a Semliki forest virus, an eastern equine encephalitis virus, a Venezuelan equine encephalitis virus, etc. Mutant or wild-type viruses sequences can be used e.g. the attenuated TC83 mutant of VEEV has been used in replicons [8].

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, it is preferred that a self-replicating RNA molecule of the invention does not encode alphavirus structural proteins. Thus a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

A RNA molecule useful with the invention may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly-A tail. It may also include a poly-A polymerase recognition sequence (e.g. AAUAAA) near its 3' end.

A RNA molecule useful with the invention will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

A RNA molecule useful with the invention can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in reference 9, the self-replicating RNA can include (in addition to any 5' cap structure) one or more nucleotides having a modified nucleobase. Thus the RNA can comprise m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6.-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluricjine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-O-methyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a self-replicating RNA can include one or more modified pyrimidine nucleobases, such as pseudouridine and/or 5-methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the RNA may include a 5' cap comprising a 7'-methylguanosine, and the first 1, 2 or 3 5' ribonucleotides may be methylated at the 2' position of the ribose.

A RNA used with the invention ideally includes only phosphodiester linkages between nucleosides, but in some embodiments it can contain phosphoramidate, phosphorothioate, and/or methylphosphonate linkages.

Ideally, a liposome includes fewer than 10 different species of RNA e.g. 5, 4, 3, or 2 different species; most preferably, a liposome includes a single RNA species i.e. all RNA molecules in the liposome have the same sequence and same length.

The amount of RNA per liposome can vary. The number of individual self-replicating RNA molecules per liposome is typically ≤50 e.g. <20, <10, <5, or 1-4 per liposome.

The Immunogen

RNA molecules used with the invention encode a polypeptide immunogen. After administration of the liposomes the RNA is translated in vivo and the immunogen can elicit an immune response in the recipient. The immunogen may elicit an immune response against a bacterium, a virus, a fungus or a parasite (or, in some embodiments, against an allergen; and in other embodiments, against a tumor antigen). The immune response may comprise an antibody response (usually including IgG) and/or a cell-mediated immune response. The polypeptide immunogen will typically elicit an immune response which recognises the corresponding bacterial, viral, fungal or parasite (or allergen or tumour) polypeptide, but in some embodiments the polypeptide may act as a mimotope to elicit an immune response which recognises a bacterial, viral, fungal or parasite saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Unlike references 1 and 10, the RNA encodes an immunogen. For the avoidance of doubt, the invention does not encompass RNA which encodes a firefly luciferase or which encodes a fusion protein of E. coli β-galactosidase or which encodes a green fluorescent protein (GFP). Such polypeptides may be useful as markers, or even in a gene therapy context, but the invention concerns delivery of RNA for eliciting an immunological response system. Thus the immunogen also is not a self protein which is delivered to supplement or substitute for a defective host protein (as in gene therapy). Also, the RNA is not total mouse thymus RNA.

In some embodiments the immunogen elicits an immune response against one of these bacteria:

Neisseria meningitidis: useful immunogens include, but are not limited to, membrane proteins such as adhesins, autotransporters, toxins, iron acquisition proteins, and factor H binding protein. A combination of three useful polypeptides is disclosed in reference 11.

Streptococcus pneumoniae: useful polypeptide immunogens are disclosed in reference 12. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

Streptococcus pyogenes: useful immunogens include, but are not limited to, the polypeptides disclosed in references 13 and 14.

Moraxella catarrhalis.

Bordetella pertussis: Useful pertussis immunogens include, but are not limited to, pertussis toxin or toxoid (PT), filamentous haemagluttinin (FHA), pertactin, and agglutinogens 2 and 3.

Staphylococcus aureus: Useful immunogens include, but are not limited to, the polypeptides disclosed in reference 15, such as a hemolysin, esxA, esxB, ferrochrome-binding protein (sta006) and/or the sta011 lipoprotein.

Clostridium tetani: the typical immunogen is tetanus toxoid.

Corynebacterium diphtheriae: the typical immunogen is diphtheria toxoid.

Haemophilus influenzae: Useful immunogens include, but are not limited to, the polypeptides disclosed in references 16 and 17.

Pseudomonas aeruginosa

Streptococcus agalactiae: useful immunogens include, but are not limited to, the polypeptides disclosed in reference 13.

Chlamydia trachomatis: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in reference 18. LcrE [19] and HtrA [20] are two preferred immunogens.

Chlamydia pneumoniae: Useful immunogens include, but are not limited to, the polypeptides disclosed in reference 21.

Helicobacter pylori: Useful immunogens include, but are not limited to, CagA, VacA, NAP, and/or urease [22].

Escherichia coli: Useful immunogens include, but are not limited to, immunogens derived from enterotoxigenic E. coli (ETEC), enteroaggregative E. coli (EAggEC), diffusely adhering E. coli (DAEC), enteropathogenic E. coli (EPEC), extraintestinal pathogenic E. coli (ExPEC) and/or enterohemorrhagic E. coli (EHEC). ExPEC strains include uropathogenic E. coli (UPEC) and meningitis/sepsis-associated E. coli (MNEC). Useful UPEC polypeptide immunogens are disclosed in references 23 and 24. Useful MNEC immunogens are disclosed in reference 25. A useful immunogen for several E. coli types is AcfD [26].

Bacillus anthracis

Yersinia pestis: Useful immunogens include, but are not limited to, those disclosed in references 27 and 28.

Staphylococcus epidermis

Clostridium perfringens or Clostridium botulinums

Legionella pneumophila

Coxiella burnetii

Brucella, such as B. abortus, B. canis, B. melitensis, B. neotomae, B. ovis, B. suis, B. pinnipediae.

Francisella, such as F. novicida, F. philomiragia, F. tularensis.

Neisseria gonorrhoeae

Treponema pallidum

Haemophilus ducreyi

Enterococcus faecalis or Enterococcus faecium

Staphylococcus saprophyticus

Yersinia enterocolitica

Mycobacterium tuberculosis

Rickettsia

Listeria monocytogenes

Vibrio cholerae

Salmonella typhi

Borrelia burgdorferi

Porphyromonas gingivalis

Klebsiella

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: Viral immunogens include, but are not limited to, those derived from Orthopoxvirus such as Variola vera, including but not limited to, Variola major and Variola minor.

Picornavirus: Viral immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: Viral immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: Viral immunogens include, but are not limited to, those derived from a Heparnavirus, such as hepatitis A virus (HAV).

Filovirus: Viral immunogens include, but are not limited to, those derived from a filovirus, such as an Ebola virus (including a Zaire, Ivory Coast, Reston or Sudan ebolavirus) or a Marburg virus.

Togavirus: Viral immunogens include, but are not limited to, those derived from a Togavirus, such as a Rubivirus, an Alphavirus, or an Arterivirus. This includes rubella virus.

Flavivirus: Viral immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral immunogens include, but are not limited to, those derived from a Pestivirus, such as Bovine viral diarrhea (BVDV), Classical swine fever (CSFV) or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a Lyssavirus (e.g. a Rabies virus) and Vesiculovirus (VSV).

Caliciviridae: Viral immunogens include, but are not limited to, those derived from Caliciviridae, such as Norwalk virus (Norovirus), and Norwalk-like Viruses, such as Hawaii Virus and Snow Mountain Virus.

Coronavirus: Viral immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: Viral immunogens include, but are not limited to, those derived from an Oncovirus, a Lentivirus (e.g. HIV-1 or HIV-2) or a Spumavirus.

Reovirus: Viral immunogens include, but are not limited to, those derived from an Orthoreovirus, a Rotavirus, an Orbivirus, or a Coltivirus.

Parvovirus: Viral immunogens include, but are not limited to, those derived from Parvovirus B19.

Herpesvirus: Viral immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral immunogens include those derived from adenovirus serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae*, Microsporidia, *Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, Curvularia spp, *Helminthosporium* spp, *Fusarium* spp, *Aspergillus* spp, *Penicillium* spp, *Monilinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale,* and *Sorghum*, the orders of Asterales and Urticales including herbs of the genera *Ambrosia, Artemisia*, and *Parietaria*. Other important inhalation allergens are those from house dust mites of the genus *Dermatophagoides* and Euroglyphus, storage mite e.g. Lepidoglyphys, Glycyphagus and Tyrophagus, those from cockroaches, midges and fleas e.g. Blatella, *Periplaneta, Chironomus* and *Ctenocephalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-ab1 (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

Liposomes of the invention are useful as components in pharmaceutical compositions for immunising subjects against various diseases. These compositions will typically include a pharmaceutically acceptable carrier in addition to the liposomes. A thorough discussion of pharmaceutically acceptable carriers is available in reference 29.

A pharmaceutical composition of the invention may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. In some embodiments such agonist(s) are also encapsulated with the RNA inside liposomes, but in other embodiments they are unencapsulated.

Pharmaceutical compositions of the invention may include the liposomes in plain water (e.g. w.f.i.) or in a buffer e.g. a phosphate buffer, a Tris buffer, a borate buffer, a succinate buffer, a histidine buffer, or a citrate buffer. Buffer salts will typically be included in the 5-20 mM range.

Pharmaceutical compositions of the invention may have a pH between 5.0 and 9.5 e.g. between 6.0 and 8.0.

Compositions of the invention may include sodium salts (e.g. sodium chloride) to give tonicity. A concentration of 10±2 mg/ml NaCl is typical e.g. about 9 mg/ml.

Compositions of the invention may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 µM e.g. 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably sterile.

Pharmaceutical compositions of the invention are preferably non-pyrogenic e.g. containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions comprise an immunologically effective amount of liposomes, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The liposome and RNA content of compositions of the invention will generally be expressed in terms of the amount of RNA per dose. A preferred dose has ≤100 μg RNA (e.g. from 10-100 μg, such as about 10 μg, 25 μg, 50 μg, 75 μg or 100 μg), but expression can be seen at much lower levels e.g. ≤1 μg/dose, ≤100 ng/dose, ≤10 ng/dose, ≤1 ng/dose, etc The invention also provides a delivery device (e.g. syringe, nebuliser, sprayer, inhaler, dermal patch, etc.) containing a pharmaceutical composition of the invention. This device can be used to administer the composition to a vertebrate subject.

Liposomes of the invention do not contain ribosomes.

Methods of Treatment and Medical Uses

In contrast to the particles disclosed in reference 10, liposomes and pharmaceutical compositions of the invention are for in vivo use for eliciting an immune response against an immunogen of interest.

The invention provides a method for raising an immune response in a vertebrate comprising the step of administering an effective amount of a liposome or pharmaceutical composition of the invention. The immune response is preferably protective and preferably involves antibodies and/or cell-mediated immunity. The method may raise a booster response.

The invention also provides a liposome or pharmaceutical composition of the invention for use in a method for raising an immune response in a vertebrate.

The invention also provides the use of a liposome of the invention in the manufacture of a medicament for raising an immune response in a vertebrate.

By raising an immune response in the vertebrate by these uses and methods, the vertebrate can be protected against various diseases and/or infections e.g. against bacterial and/or viral diseases as discussed above. The liposomes and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; unlike reference 1, intraglossal injection is not typically used with the present invention). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

Formula (X)

Compounds of formula (X) contains a hydrophilic polymer head group linked to a lipid moiety. They can be described as "stealth lipids" and they have formula:

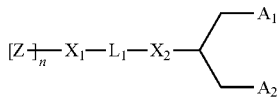

wherein:
Z is a hydrophilic head group component selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein the polymer may be linear or branched, and wherein the polymer may be optionally substituted;
wherein Z is polymerized by n subunits;
n is a number-averaged degree of polymerization between 10 and 200 units of Z, wherein n is optimized for different polymer types;
$L_1$ is an optionally substituted $C_{1-10}$ alkylene or $C_{1-10}$ heteroalkylene linker including zero, one or two of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—),
wherein R' is independently selected from —H, —NH—, —NH$_2$, —O—, —S—, a phosphate or an optionally substituted $C_{1-10}$ alkylene;
$X_1$ and $X_2$ are independently selected from a carbon or a heteroatom selected from —NH—, —O—, —S— or a phosphate;
$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or $A_1$ and $A_2$ together with the carbon atom to which they are attached form an optionally substituted steroid.

In one embodiment, the compound of formula (X) has formula (X')

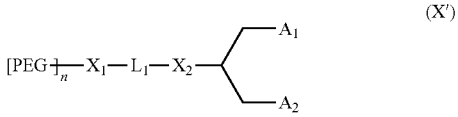

wherein
PEG is a poly(ethylene glycol) subunit, wherein the PEG may be linear or branched;

n is a number-averaged degree of polymerization between 10 and 200 units of PEG, preferably around 45 units;
$L_1$ is an optionally substituted $C_{1-10}$ heteroalkylene linker containing one or two of an ether, ester, succinate, carbamate, carbonate, urea, amine, amide, imine, thioether, xanthate, and phosphodiester;
$X_1$ and $X_2$ are oxygen;
$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

The lipids of formulae (X) and (X'), when formulated with cationic lipids to form liposomes, can increase the length of time for which a liposome can exist in vivo (e.g. in the blood). They can shield the surface of a liposome surface and thereby reduce opsonisation by blood proteins and uptake by macrophages. Further details are in references 30 and 31. In one embodiment, the lipid comprises a group selected from PEG (sometimes referred to as poly(ethylene oxide)) and polymers based on poly(oxazoline), poly(vinyl alcohol), poly(glycerol), poly(N-vinylpyrrolidone), poly[N-(2-hydroxypropyl)methacrylamide] and poly(amino acid)s.

Suitable PEGylated lipids for use with the invention include polyethyleneglycol-diacylglycerol or polyethyleneglycol-diacylglycamide (PEG-DAG) conjugates including those comprising a dialkylglycerol or dialkylglycamide group having alkyl chain length independently comprising from about C4 to about C40 saturated or unsaturated carbon atoms. The dialkylglycerol or dialkylglycamide group can further comprise one or more substituted alkyl groups. The PEGylated lipid can be selected from PEG-dilaurylglycerol, PEG-dimyristoylglycerol (catalog #GM-020 from NOF), PEG-dipalmitoylglycerol, PEG-distearoylglycerol, PEG-dilaurylglycamide, PEG-dimyristylglycamide, PEG-dipalmitoyl-glycamide, and PEG-disterylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), 1,2-dimyristoyl-sn-glycero-3-phosphoethanolamine-N-[methoxy (polyethylene glycol)-2000](catalog #880150P from Avanti Polar Lipids). Other useful PEGylated lipids are S001, S002, S003, S004, S005, S006, S007, S008, S009, S010, S011, and CS-020SA (NOF); S010 and S011 are disclosed in ref. 32 under the labels IVa and IVc, respectively. In ref. 32, a different synthesis from that reported herein is used to prepare IVa and IVc.

Chemical Terms and Definitions

Halo

The term "halogen" (or "halo") includes fluorine, chlorine, bromine and iodine.

Alkyl, Alkylene, Alkenyl, Alkynyl, Cycloalkyl Etc.

The terms "alkyl", "alkylene", "alkenyl" and "alkynyl" are used herein to refer to both straight and branched chain acyclic forms. Cyclic analogues thereof are referred to as cycloalkyl, etc.

The term "alkyl" includes monovalent, straight or branched, saturated, acyclic hydrocarbyl groups. In one embodiment alkyl is $C_{1-10}$ alkyl, in another embodiment $C_{1-6}$ alkyl, in another embodiment $C_{1-4}$ alkyl, such as methyl, ethyl, n-propyl, i-propyl or t-butyl groups.

The term "cycloalkyl" includes monovalent, saturated, cyclic hydrocarbyl groups. In one embodiment cycloalkyl is $C_{3-10}$ cycloalkyl, in another embodiment $C_{3-6}$ cycloalkyl such as cyclopentyl and cyclohexyl.

The term "alkoxy" means alkyl-O—.

The term "alkenyl" includes monovalent, straight or branched, unsaturated, acyclic hydrocarbyl groups having at least one carbon-carbon double bond and, in one embodiment, no carbon-carbon triple bonds. In one embodiment alkenyl is $C_{2-10}$ alkenyl, in another embodiment $C_{2-6}$ alkenyl, in another embodiment $C_{2-4}$ alkenyl.

The term "cycloalkenyl" includes monovalent, partially unsaturated, cyclic hydrocarbyl groups having at least one carbon-carbon double bond and, in one embodiment, no carbon-carbon triple bonds. In one embodiment cycloalkenyl is $C_{3-10}$ cycloalkenyl, in another embodiment $C_{5-10}$ cycloalkenyl, e.g. cyclohexenyl or benzocyclohexyl.

The term "alkynyl" includes monovalent, straight or branched, unsaturated, acyclic hydrocarbyl groups having at least one carbon-carbon triple bond and, in one embodiment, no carbon-carbon double bonds. In one embodiment, alkynyl is $C_{2-10}$ alkynyl, in another embodiment $C_{2-6}$ alkynyl, in another embodiment $C_{2-4}$ alkynyl.

The term "cycloalkynyl" includes monovalent, partially unsaturated, cyclic hydrocarbyl groups having at least one carbon-carbon triple bond and, in one embodiment, no carbon-carbon double bonds. In one embodiment cycloalkynyl is $C_{3-10}$ cycloalkenyl, in another embodiment $C_{5-10}$ cycloalkynyl.

The term "alkylene" includes divalent, straight or branched, saturated, acyclic hydrocarbyl groups. In one embodiment alkylene is $C_{1-10}$ alkylene, in another embodiment $C_{1-6}$ alkylene, in another embodiment $C_{1-4}$ alkylene, such as methylene, ethylene, n-propylene, i-propylene or t-butylene groups.

The term "alkenylene" includes divalent, straight or branched, unsaturated, acyclic hydrocarbyl groups having at least one carbon-carbon double bond and, in one embodiment, no carbon-carbon triple bonds. In one embodiment alkenylene is $C_{2-10}$ alkenylene, in another embodiment $C_{2-6}$ alkenylene, in another embodiment $C_{2-4}$ alkenylene.

The term "alkynylene" includes divalent, straight or branched, unsaturated, acyclic hydrocarbyl groups having at least one carbon-carbon triple bond and, in one embodiment, no carbon-carbon double bonds. In one embodiment alkynylene is $C_{2-10}$ alkynylene, in another embodiment $C_{2-6}$ alkynylene, in another embodiment $C_{2-4}$ alkynylene.

Heteroalkyl Etc.

The term "heteroalkyl" includes alkyl groups in which up to six carbon atoms, in one embodiment up to five carbon atoms, in another embodiment up to four carbon atoms, in another embodiment up to three carbon atoms, in another embodiment up to two carbon atoms, in another embodiment one carbon atom, are each replaced independently by O, $S(O)_q$, N, $P(O)_r$ or Si (and preferably O, $S(O)_q$ or N), provided at least one of the alkyl carbon atoms remains. The heteroalkyl group may be C-linked or hetero-linked, i.e. it may be linked to the remainder of the molecule through a carbon atom or through O, $S(O)_q$, N, $P(O)_r$ or Si.

The term "heterocycloalkyl" includes cycloalkyl groups in which up to six carbon atoms, in one embodiment up to five carbon atoms, in another embodiment up to four carbon atoms, in another embodiment up to three carbon atoms, in another embodiment up to two carbon atoms, in another embodiment one carbon atom, are each replaced independently by O, $S(O)_q$ or N, provided at least one of the cycloalkyl carbon atoms remains. Examples of heterocycloalkyl groups include oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxazepanyl, 1,4-dithiepanyl, 1,4-thiazepanyl and 1,4-diazepanyl. The heterocycloalkyl group may be C-linked or N-linked, i.e. it may be linked to the remainder of the molecule through a carbon atom or through a nitrogen atom.

The term "heteroalkenyl" includes alkenyl groups in which up to three carbon atoms, in one embodiment up to two carbon atoms, in another embodiment one carbon atom, are each replaced independently by O, $S(O)_q$ or N, provided at least one of the alkenyl carbon atoms remains. The heteroalkenyl group may be C-linked or hetero-linked, i.e. it may be linked to the remainder of the molecule through a carbon atom or through O, $S(O)_q$ or N.

The term "heterocycloalkenyl" includes cycloalkenyl groups in which up to three carbon atoms, in one embodiment up to two carbon atoms, in another embodiment one carbon atom, are each replaced independently by O, $S(O)_q$ or N, provided at least one of the cycloalkenyl carbon atoms remains. Examples of heterocycloalkenyl groups include 3,4-dihydro-2H-pyranyl, 5-6-dihydro-2H-pyranyl, 2H-pyranyl, 1,2,3,4-tetrahydropyridinyl and 1,2,5,6-tetrahydropyridinyl. The heterocycloalkenyl group may be C-linked or N-linked, i.e. it may be linked to the remainder of the molecule through a carbon atom or through a nitrogen atom.

The term "heteroalkynyl" includes alkynyl groups in which up to three carbon atoms, in one embodiment up to two carbon atoms, in another embodiment one carbon atom, are each replaced independently by O, $S(O)_q$ or N, provided at least one of the alkynyl carbon atoms remains. The heteroalkynyl group may be C-linked or hetero-linked, i.e. it may be linked to the remainder of the molecule through a carbon atom or through O, $S(O)_q$ or N.

The term "heterocycloalkynyl" includes cycloalkynyl groups in which up to three carbon atoms, in one embodiment up to two carbon atoms, in another embodiment one carbon atom, are each replaced independently by O, $S(O)_q$ or N, provided at least one of the cycloalkynyl carbon atoms remains. The heterocycloalkenyl group may be C-linked or N-linked, i.e. it may be linked to the remainder of the molecule through a carbon atom or through a nitrogen atom.

The term "heteroalkylene" includes alkylene groups in which up to three carbon atoms, in one embodiment up to two carbon atoms, in another embodiment one carbon atom, are each replaced independently by O, $S(O)_q$ or N, provided at least one of the alkylene carbon atoms remains.

The term "heteroalkenylene" includes alkenylene groups in which up to three carbon atoms, in one embodiment up to two carbon atoms, in another embodiment one carbon atom, are each replaced independently by O, $S(O)_q$ or N, provided at least one of the alkenylene carbon atoms remains.

The term "heteroalkynylene" includes alkynylene groups in which up to three carbon atoms, in one embodiment up to two carbon atoms, in another embodiment one carbon atom, are each replaced independently by O, $S(O)_q$ or N, provided at least one of the alkynylene carbon atoms remains.

Aryl

The term "aryl" includes monovalent, aromatic, cyclic hydrocarbyl groups, such as phenyl or naphthyl (e.g. 1-naphthyl or 2-naphthyl). In general, the aryl groups may be monocyclic or polycyclic fused ring aromatic groups. Preferred aryl are $C_6$-$C_{14}$ aryl.

Other examples of aryl groups are monovalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

The term "arylalkyl" means alkyl substituted with an aryl group, e.g. benzyl.

The term "arylene" includes divalent aromatic, cyclic hydrocarbyl groups, such as phenylene. In general, the arylene groups may be monocyclic or polycyclic fused ring aromatic groups. Preferred arylene are $C_6$-$C_{14}$ arylene. Other examples of arylene groups are divalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

Heteroaryl

The term "heteroaryl" includes monovalent, heteroaromatic, cyclic hydrocarbyl groups additionally containing one or more heteroatoms independently selected from O, S, N and $NR^N$, where $R^N$ is defined below (and in one embodiment is H or alkyl (e.g. $C_{1-6}$ alkyl)).

In general, the heteroaryl groups may be monocyclic or polycyclic (e.g. bicyclic) fused ring heteroaromatic groups. In one embodiment, heteroaryl groups contain 5-13 ring members (preferably 5-10 members) and 1, 2, 3 or 4 ring heteroatoms independently selected from O, S, N and $NR^N$. In one embodiment, a heteroaryl group may be 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members and 1, 2, 3 or 4 heteroatoms selected from O, S, N or $NR^N$.

In one embodiment, 5-membered monocyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 5 ring members are carbon atoms).

Examples of 5-membered monocyclic heteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl, pyridyl, pyrimidinyl, pyridazinyl, pyrazinyl, 1,3,5 triazinyl, 1,2,4 triazinyl, 1,2,3 triazinyl and tetrazolyl.

Examples of 6-membered monocyclic heteroaryl groups are pyridinyl, pyridazinyl, pyrimidinyl and pyrazinyl.

In one embodiment, 6-membered monocyclic heteroaryl groups contain 1 or 2 ring members which are =N— atoms (where the remainder of the 6 ring members are carbon atoms).

Bicyclic heteroaromatic groups include fused-ring heteroaromatic groups containing 9-13 ring members and 1, 2, 3, 4 or more heteroatoms selected from O, S, N or $NR^N$.

In one embodiment, 9-membered bicyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 9 ring members are carbon atoms).

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,2-a]pyridinyl, pyrrolo[1,2-b]pyridazinyl and imidazo[1,2-c]pyrimidinyl.

In one embodiment, 10-membered bicyclic heteroaryl groups contain 1-3 ring members which are =N— atoms (where the remainder of the 10 ring members are carbon atoms).

Examples of 10-membered fused-ring bicyclic heteroaryl groups are quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

The term "heteroarylalkyl" means alkyl substituted with a heteroaryl group.

The term "heteroarylene" includes divalent heteroaromatic, cyclic hydrocarbyl groups additionally containing one or more heteroatoms independently selected from O, S, N and $NR^N$, where $R^N$ is defined below (and in one embodiment is H or alkyl (e.g. $C_{1-6}$ alkyl)). In general, the heteroarylene groups may be monocyclic or polycyclic (e.g. bicyclic) fused ring heteroaromatic groups. In one embodiment, heteroarylene groups contain 5-13 ring members (preferably 5-10 members) and 1, 2, 3 or 4 ring heteroatoms independently selected from O, S, N and $NR^N$. In one embodiment, a heteroarylene group may be 5, 6, 9 or 10 membered, e.g. 5-membered monocyclic, 6-membered monocyclic, 9-membered fused-ring bicyclic or 10-membered fused-ring bicyclic. The term "heteroarylene" includes divalent derivatives of each of the heteroaryl groups discussed above.

The terms "aryl", "aromatic", "heteroaryl" and "heteroaromatic" also include groups that are partially reduced. Thus, for example, "heteroaryl" includes fused species in which one of the rings has been reduced to a saturated ring (e.g. 1,2,3,4-tetrahydro-1,8-naphthyridin-2-yl).

General

Unless indicated explicitly otherwise, where combinations of groups are referred to herein as one moiety, e.g. arylalkyl, the last mentioned group contains the atom by which the moiety is attached to the rest of the molecule.

Where reference is made to a carbon atom of an alkyl group or other group being replaced by O, $S(O)_q$, N or $P(O)_r$, what is intended is that:

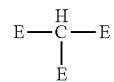

is replaced by

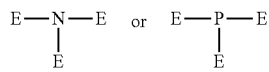

(wherein E cannot be H);

—CH= is replaced by —N= or —$P(O)_r$=;

≡C—H is replaced by ≡N or ≡$P(O)_r$; or

—$CH_2$— is replaced by —O—, —$S(O)_q$—, —$NR^N$— or —$P(O)_rR^N$—, where $R^N$ is H or optionally substituted $C_{1-6}$ alkyl, $C_{1-6}$ heteroalkyl, $C_{3-6}$ cycloalkyl, $C_{3-6}$ heterocycloalkyl, $C_{2-6}$ alkenyl, $C_{2-6}$ heteroalkenyl, $C_{3-6}$ cycloalkenyl, $C_{3-6}$ heterocycloalkenyl, phenyl, or heteroaryl containing 5 or 6 ring members. $R^N$ is preferably H, $C_{1-6}$ alkyl or $C_{3-6}$ cycloalkyl.

q is independently 0, 1 or 2. In one embodiment, q is 0.

r is independently 0 or 1. In one embodiment, r is 0.

Where reference is made to a carbon atom being replaced by Si, what is intended is that the carbon atom is swapped for a silicon atom but that the bonds otherwise remain the same. Thus, for example, —$CH_2$— is replaced by —$SiH_2$—; —CH= is replaced by —SiH=; and ≡C—H is replaced by ≡Si—H.

By way of clarification, in relation to the above mentioned heteroatom containing groups (such as heteroalkyl etc.), where a numerical of carbon atoms is given, for instance $C_{3-6}$ heteroalkyl, what is intended is a group based on $C_{3-6}$ alkyl in which one or more of the 3-6 chain carbon atoms is replaced by O, $S(O)_q$ or N. Accordingly, a $C_{3-6}$ heteroalkyl group would, for example, contain less than 3-6 chain carbon atoms. As another example, a pyridyl group would be classed as a $C_6$ heteroaryl group even though it contains 5 carbon atoms.

Substitution

Groups of the compounds of the invention (e.g. alkyl, cycloalkyl, alkoxy, alkenyl, cycloalkenyl, alkynyl, alkylene, alkenylene, heteroalkyl, heterocycloalkyl, heteroalkenyl, heterocycloalkenyl, heteroalkynyl, heteroalkylene, heteroalkenylene aryl, arylalkyl, arylheteroalkyl, heteroaryl, heteroarylalkyl or heteroarylheteroalkyl groups etc.) may be substituted or unsubstituted, in one embodiment unsubstituted. Typically, substitution involves the notional replacement of a hydrogen atom with a substituent group, or two hydrogen atoms in the case of substitution by =O.

Where substituted, there will generally be 1 to 5 substituents on each group, in one embodiment 1 to 3 substituents, in one embodiment 1 or 2 substituents, in one embodiment 1 substituent. One embodiment includes more than one substituent on the same atom, e.g. an acetal group.

In one embodiment, the substituent(s) is/are independently $Sub^1$ or $Sub^2$ (in one embodiment $Sub^2$) wherein:

$Sub^1$ is independently halogen, trihalomethyl, trihaloethyl, —$NO_2$, —CN, —$N^+(R^s)_2O^-$, —$CO_2H$, —$CO_2R^s$, —$SO_3H$, —$SOR^s$, —$SO_2R^s$, —$SO_3R^s$, —OC(=O)$OR^s$, —C(=O)H, —C(=O)$R^s$, —OC(=O)$R^s$, =O, —$NR^s_2$, —C(=O)$NH_2$, —C(=O)$NR^s_2$, —N($R^s$)C(=O)$OR^s$, —N($R^s$)C(=O)$NR^s_2$, —OC(=O)$NR^s_2$, —N($R^s$)C (=O)$R^s$, —C(=S)$NR^s_2$, —$NR^sC$(=S)$R^s$, —$SO_2NR^s_2$, —$NR^sSO_2R^s$, —N($R^s$)C(=S)$NR^s_2$, —N($R^s$)$SO_2NR^s_2$, —$R^s$ or —$Z^sR^s$, wherein:

$Z^s$ is independently O, S or $NR^s$;

$R^s$ is independently H or $C_{1-6}$ alkyl, $C_{1-6}$ heteroalkyl, -$(Alk^a)_f$—$C_{3-6}$ cycloalkyl, -$(Alk^a)_f$—$C_{3-6}$ heterocycloalkyl, $C_{2-6}$ alkenyl, $C_{2-6}$ heteroalkenyl, -$(Alk^a)_f$—$C_{3-6}$ cycloalkenyl, -$(Alk^a)_f$—$C_{3-6}$ heterocycloalkenyl, $C_{2-6}$ alkynyl, $C_{2-6}$ heteroalkynyl, -$(Alk^a)_f$—$C_{6-14}$ aryl, -$(Alk^a)_f$—$C_{6-14}$ aryl or -$(Alk^a)_f$-heteroaryl (where heteroaryl contains 5-13 ring members), where f is 0 or 1;

$Alk^a$ is $C_{1-6}$ alkylene or $C_{1-6}$ heteroalkylene; and $R^s$ is optionally substituted itself (in one embodiment unsubstituted) by 1 to 3 substituents $Sub^2$;

$Sub^2$ is independently halogen, trihalomethyl, trihaloethyl, —$NO_2$, —CN, —$N^+(C_{1-6}$ alkyl$)_2O^-$, —$CO_2H$, —$CO_2C_{1-6}$ alkyl, —$SO_3H$, —$SOC_{1-6}$ alkyl, —$SO_2C_{1-6}$ alkyl, —$SO_3C_{1-6}$ alkyl, —OC(=O)$OC_{1-6}$ alkyl, —C(=O)H, —C(=O)$C_{1-6}$ alkyl, —OC(=O)$C_{1-6}$ alkyl, =O, —N($C_{1-6}$ alkyl$)_2$, —C(=O)$NH_2$, —C(=O)N($C_{1-6}$ alkyl$)_2$, —N($C_{1-6}$ alkyl)C(=O)O($C_{1-6}$ alkyl), —N($C_{1-6}$ alkyl)C(=O)N($C_{1-6}$ alkyl$)_2$, —OC(=O)N($C_{1-6}$ alkyl$)_2$, —N($C_{1-6}$ alkyl)C(=O)$C_{1-6}$ alkyl, —C(=S)N($C_{1-6}$ alkyl$)_2$, —N($C_{1-6}$ alkyl)C(=S)$C_{1-6}$ alkyl, —$SO_2N(C_{1-6}$ alkyl$)_2$, —N($C_{1-6}$ alkyl)$SO_2C_{1-6}$ alkyl, —N($C_{1-6}$ alkyl)C(=S)N($C_{1-6}$ alkyl) 2, —N($C_{1-6}$ alkyl)$SO_2N(C_{1-6}$ alkyl$)_2$, —$C_{1-6}$ alkyl, —$C_{1-6}$ heteroalkyl, —$C_{3-6}$ cycloalkyl, —$C_{3-6}$ heterocycloalkyl, —$C_{2-6}$ alkenyl, —$C_{2-6}$ heteroalkenyl, —$C_{3-6}$ cycloalkenyl, —$C_{3-6}$ heterocycloalkenyl, —$C_{2-6}$ alkynyl, —$C_{2-6}$ heteroalkynyl, —$C_{6-14}$ aryl, —$C_{5-13}$ heteroaryl, —$Z^t$—$C_{1-6}$ alkyl, —$Z^t$—$C_{3-6}$ cycloalkyl, —$Z^t$—$C_{2-6}$ alkenyl, —$Z^t$—$C_{3-6}$ cycloalkenyl, or —$Z^t$—$C_{2-6}$ alkynyl; and $Z^t$ is independently O, S, NH or N($C_{1-6}$ alkyl).

While $R^s$ in $Sub^1$ can be optionally substituted by 1 to 3 substituents $Sub^2$, $Sub^2$ is unsubstituted. However, in one embodiment, R is unsubstituted.

In one embodiment, $R^s$ is H or $C_{1-6}$ alkyl, optionally substituted by 1 to 3 substituents $Sub^2$.

In one embodiment, $Sub^2$ is independently halogen, trihalomethyl, trihaloethyl, —$NO_2$, —CN, —$N^+(C_{1-6}$ alkyl$)_2$ $O^-$, —$CO_2H$, —$SO_3H$, —$SOC_{1-6}$ alkyl, —$SO_2C_{1-6}$ alkyl, —C(=O)H, —C(=O)$C_{1-6}$ alkyl, =O, —N($C_{1-6}$ alkyl$)_2$, —C(=O)$NH_2$, —$C_{1-6}$ alkyl, —$C_{3-6}$ cycloalkyl, —$C_{3-6}$ heterocycloalkyl, —$Z^t$—$C_{1-6}$ alkyl or —$Z^t$—$C_{3-6}$ cycloalkyl.

In one embodiment, where the substituted group is acyclic (e.g. alkyl, heteroalkyl, alkenyl etc.), $Sub^1$ is not —$R^s$ and $Sub^2$ is not —$C_{1-6}$ alkyl, —$C_{1-6}$ heteroalkyl, —$C_{2-6}$ alkenyl, —$C_{2-6}$ heteroalkenyl, —$C_{2-6}$ alkynyl or —$C_{2-6}$ heteroalkynyl.

Where a group other than $Sub^2$ has at least 2 positions which may be substituted, the group may be substituted by both ends of an alkylene, alkenylene, alkynylene, heteroalkylene, heteroalkenylene or heteroalkynylene chain (in one embodiment containing 1 to 6 atoms, in a further embodiment 3 to 6 atoms, and in a further embodiment 3 or 4 atoms) to form a cyclic moiety. That chain is optionally substituted by 1 to 3 substituents $Sub^2$. In one embodiment that chain is not substituted. Thus, the terms optionally substituted "cycloalkyl", "cycloalkenyl", "cycloalkynyl", "heterocycloalkyl", "heterocycloalkenyl", "heterocycloalkynyl", "aryl" and "heteroaryl" include fused species. E.g. "optionally substituted cycloalkyl" includes a species in which two cycloalkyl rings are fused, and "optionally substituted heteroaryl" includes a species in which a heterocycloalkyl ring is fused to the aromatic ring (e.g. 5,6,7,8-tetrahydro-1,8-naphthyridin-2-yl).

Where a group other than $Sub^2$ has an atom which may be substituted twice, that atom may be substituted by both ends of an alkylene, alkenylene, alkynylene, heteroalkylene, heteroalkenylene or heteroalkynylene chain (in one embodiment containing 2 to 8 atoms, in a further embodiment 3 to 6 atoms, and in a further embodiment 4 or 5 atoms) to form a cyclic moiety. That chain is optionally substituted by 1 to 3 substituents $Sub^2$. In one embodiment that chain is not substituted. Thus, the terms optionally substituted "cycloalkyl", "cycloalkenyl", "cycloalkynyl", "heterocycloalkyl", "heterocycloalkenyl", "heterocycloalkynyl", "aryl" and "heteroaryl" include spiro species.

By way of clarification, when a group has a heteroatom, a substituent may be bonded to the heteroatom. Thus, for example, "optionally substituted heteroalkyl" includes —$CH_2$—N($Sub^1$)—$CH_2$—, —CH($Sub^1$)—NH—$CH_2$— and —CH($Sub^1$)—N($Sub^1$)—$CH_2$— etc.

Modifier Terms

When a list is preceded by a modifier, it is intended that the modifier is to be understood as applying to each of the items in the list. For example, the phrase "optionally substituted $C_{3-20}$-heterocycloalkyl, $C_{3-20}$-heterocycloalkenyl, $C_{3-20}$-heterocycloalkynyl or $C_{5-20}$-heteroaryl group" means that each of the four items in the list, namely the $C_{3-20}$-heterocycloalkyl group, the $C_{3-20}$-heterocycloalkenyl group, the $C_{3-20}$-heterocycloalkynyl group and the $C_{6-20}$-heteroaryl group, may be optionally substituted.

When a group is characterised by a first modifier and then, later on, the same group is characterised by a subsequent modifier, what is meant is that the group is characterised by both modifiers simultaneously. For example, if a group is described as a "$C_{3-20}$-heterocycloalkynyl" (the first modifier) group and then later the same group is described as a "$C_{5-16}$" (the subsequent modifier) group, what is meant is a $C_{5-16}$ heterocycloalkynyl group.

Steroids

As used herein, the term "steroid" refers to any group comprising the following structure (which structure is referred to herein as the "steroid skeleton").

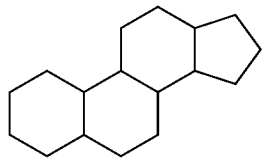 [SMILES: C1CCC2C(C1)CCC1C3CCCC3CCC21]

Purely for the purposes of illustration, the steroid skeleton has been drawn above as fully saturated. The term steroid, however, is also intended to cover instances where there is unsaturation in the steroid skeleton. For example, the term steroid covers a group which comprises the fully unsaturated (mancude) basic skeleton, 15H-cyclopenta[a]phenanthrene:

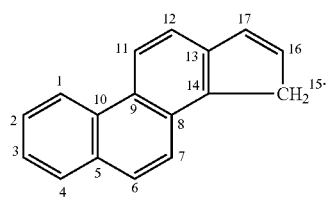

The term steroid also covers a group which comprises a partially unsaturated steroid skeleton.

The term steroid also covers "seco" derivatives of the steroid skeleton, i.e. groups in which ring cleavage has been effected; "nor" and "homo" derivatives of the steroid skeleton which involve ring contraction and expansion, respectively (see Systemic Nomenclature of Organic Chemistry, by D. Hellwinkel, published by Springer, 2001, ISBN: 3-540-41138-0, page 203 for "seco" and page 204 for "nor" and "homo"). In one embodiment, however, such seco derivatives are not encompassed by the term "steroid". In another embodiment, such nor derivatives are not encompassed by the term "steroid". In another embodiment, such homo derivatives are not encompassed by the term "steroid". Thus in one embodiment, such seco, nor and homo derivatives are not encompassed by the term "steroid".

The term steroid also covers instances where one or more of the carbon atoms in the structure labelled steroid skeleton is replaced by a heteroatom. In one such embodiment, up to six carbon atoms, in one embodiment up to five carbon atoms, in another embodiment up to four carbon atoms, in another embodiment up to three carbon atoms, in another embodiment up to two carbon atoms, in another embodiment one carbon atom, are each replaced independently by O, $S(O)_q$, N, $P(O)_r$ or Si (and preferably O, $S(O)_q$ or N). In one embodiment, however, the term "steroid" comprises species in which the "steroid basic skeleton" contains no heteroatoms.

A steroid ring system is numbered according to the convention set out below.

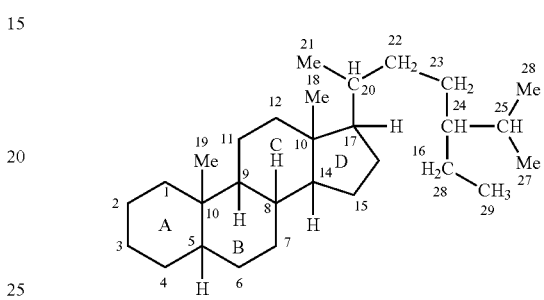

The term steroid encompasses sterols, steroid hormones, bile acids and salts of bile acids. A sterol is any steroid with a hydroxyl group at the 3-position of the A-ring.

Unsaturation

In accordance with standard use, the omega-3 position refers to the third bond from the (methyl) terminal of the chain; the omega-6 position refers to the sixth bond from the (methyl) terminal of the chain and the omega-9 position refers to the ninth bond from the (methyl) terminal of the chain.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 33-39, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to charge, to cations, to anions, to zwitterions, etc., are taken at pH 7.

TLR3 is the Toll-like receptor 3. It is a single membrane-spanning receptor which plays a key role in the innate immune system. Known TLR3 agonists include poly(I:C). "TLR3" is the approved HGNC name for the gene encoding this receptor, and its unique HGNC ID is HGNC:11849. The RefSeq sequence for the human TLR3 gene is GI:2459625.

TLR7 is the Toll-like receptor 7. It is a single membrane-spanning receptor which plays a key role in the innate immune system. Known TLR7 agonists include e.g. imiquimod. "TLR7" is the approved HGNC name for the gene encoding this receptor, and its unique HGNC ID is HGNC: 15631. The RefSeq sequence for the human TLR7 gene is GI:67944638.

TLR8 is the Toll-like receptor 8. It is a single membrane-spanning receptor which plays a key role in the innate immune system. Known TLR8 agonists include e.g. resiquimod. "TLR8" is the approved HGNC name for the gene encoding this receptor, and its unique HGNC ID is HGNC: 15632. The RefSeq sequence for the human TLR8 gene is GI:20302165.

The RIG-I-like receptor ("RLR") family includes various RNA helicases which play key roles in the innate immune system[40]. RLR-1 (also known as RIG-I or retinoic acid inducible gene I) has two caspase recruitment domains near its N-terminus. The approved HGNC name for the gene encoding the RLR-1 helicase is "DDX58" (for DEAD (Asp-Glu-Ala-Asp) box polypeptide 58) and the unique HGNC ID is HGNC:19102. The RefSeq sequence for the human RLR-1 gene is GI:77732514. RLR-2 (also known as MDA5 or melanoma differentiation-associated gene 5) also has two caspase recruitment domains near its N-terminus. The approved HGNC name for the gene encoding the RLR-2 helicase is "IFIH1" (for interferon induced with helicase C domain 1) and the unique HGNC ID is HGNC: 18873. The RefSeq sequence for the human RLR-2 gene is GI: 27886567. RLR-3 (also known as LGP2 or laboratory of genetics and physiology 2) has no caspase recruitment domains. The approved HGNC name for the gene encoding the RLR-3 helicase is "DHX58" (for DEXH (Asp-Glu-X-His) box polypeptide 58) and the unique HGNC ID is HGNC:29517. The RefSeq sequence for the human RLR-3 gene is GI:149408121.

PKR is a double-stranded RNA-dependent protein kinase. It plays a key role in the innate immune system. "EIF2AK2" (for eukaryotic translation initiation factor 2-alpha kinase 2) is the approved HGNC name for the gene encoding this enzyme, and its unique HGNC ID is HGNC:9437. The RefSeq sequence for the human PKR gene is GI:208431825.

BRIEF DESCRIPTION OF DRAWINGS

FIG. 3 shows protein expression (as relative light units, RLU) at days 1, 3 and 6 after delivery of RNA in liposomes with PEGs of different lengths: 1 kDa (triangles); 2 kDa (circles); 3 kDa (squares).

FIG. 4 shows a gel with stained RNA. Lanes show (1) markers (2) naked replicon (3) replicon encapsulated in liposome (4) liposome treated with RNase then subjected to phenol/chloroform extraction.

FIG. 5 shows protein expression at days 1, 3 and 6 after delivery of RNA as a virion-packaged replicon (squares), as naked RNA (diamonds), or in liposomes (+=0.1 μg, x=1 μg).

FIG. 6 shows protein expression at days 1, 3 and 6 after delivery of four different doses of liposome-encapsulated RNA.

FIG. 16 shows structures of three PEG-conjugated DMG lipids (1-3 kDa).

MODES FOR CARRYING OUT THE INVENTION

RNA Replicons

Figure 1:
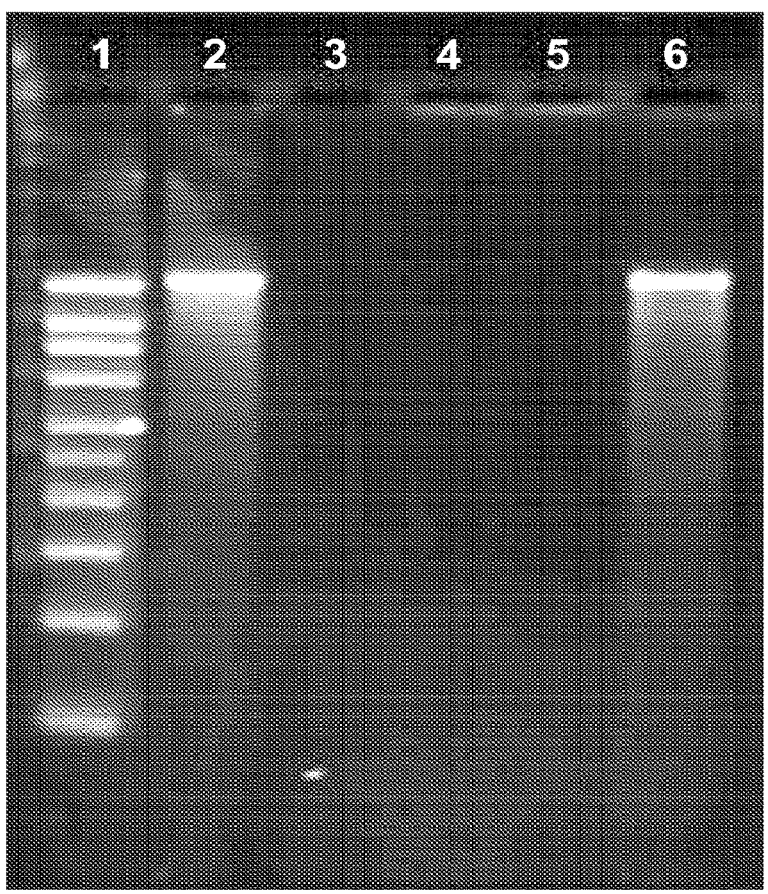
FIG. 1 shows a gel with stained RNA. Lanes show (1) markers (2) naked replicon (3) replicon after RNase treatment (4) replicon encapsulated in liposome (5) liposome after RNase treatment (6) liposome treated with RNase then subjected to phenol/chloroform extraction.

Various replicons are used below. In general these are based on a hybrid alphavirus genome with non-structural proteins from venezuelan equine encephalitis virus (VEEV), a packaging signal from VEEV, and a 3' UTR from Sindbis virus or a VEEV mutant. The replicon is about 10 kb long and has a poly-A tail.

Plasmid DNA encoding alphavirus replicons (named: pT7-mVEEV-FL.RSVF or A317; pT7-mVEEV-SEAP or A306; pSP6-VCR-GFP or A50) served as a template for synthesis of RNA in vitro. The replicons contain the alphavirus genetic elements required for RNA replication but lack those encoding gene products necessary for particle assembly; the structural proteins are instead replaced by a protein of interest (either a reporter, such as SEAP or GFP, or an immunogen, such as full-length RSV F protein) and so the replicons are incapable of inducing the generation of infectious particles. A bacteriophage (T7 or SP6) promoter upstream of the alphavirus cDNA facilitates the synthesis of the replicon RNA in vitro and a hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion).

The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260nm}$. Integrity of the in vitro transcripts was confirmed by denaturing agarose gel electrophoresis.

Liposomal Encapsulation

RNA was encapsulated in liposomes made essentially by the method of references 7 and 41. The liposomes were made of 10% DSPC (zwitterionic), 40% DlinDMA (cationic), 48% cholesterol and 2% PEG-conjugated DMG. These proportions refer to the % moles in the total liposome.

DlinDMA (1,2-dilinoleyloxy-N,N-dimethyl-3-aminopropane) was synthesized using the procedure of reference 2. DSPC (1,2-Distearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N—(N',N'-dimethylaminoethane)-carbamoyl]cholesterol hydrochloride) were from Avanti Polar Lipids.

Figure 2:
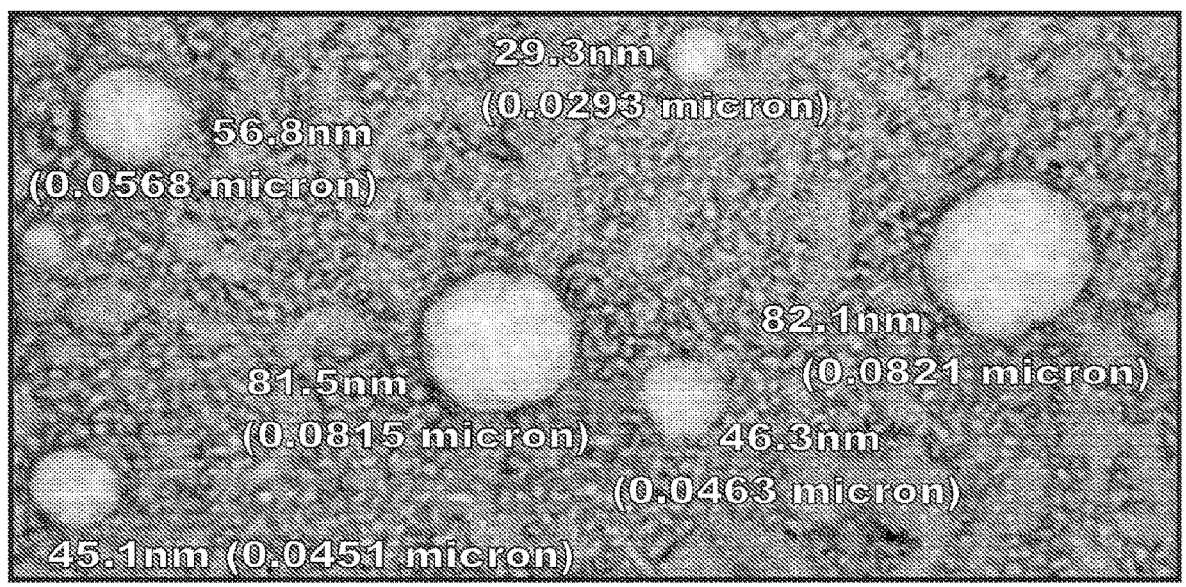
FIG. 2 is an electron micrograph of liposomes.

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was diluted with 6 ml buffer then filtered. The resulting product contained liposomes, with ~95% encapsulation efficiency. FIG. 2 shows an example electron micrograph of liposomes prepared by these methods. These liposomes contain encapsulated RNA encoding full-length RSV F antigen. Dynamic light scattering of one batch showed an average diameter of 141 nm (by intensity) or 78 nm (by number).

In one particular encapsulation method, fresh lipid stock solutions in ethanol were prepared. 37 mg of DlinDMA, 11.8 mg of DSPC, 27.8 mg of Cholesterol and 8.07 mg of PEG-conjugated DMG were weighed and dissolved in 7.55 mL of ethanol. Five different conjugated PEGs were used: PEG-500, PEG-750, PEG-1000, PEG-2000 or PEG-3000. The freshly prepared lipid stock solution was gently rocked at 37° C. for about 15 min to form a homogenous mixture. Then, 226.7 μL of the stock was added to 1.773 mL ethanol to make a working lipid stock solution of 2 mL. A 2 mL working solution of RNA was also prepared from a stock solution of ~1 μg/μL in 100 mM citrate buffer (pH 6). Three 20 mL glass vials (with stir bars) were rinsed with RNase Away solution and washed with plenty of MilliQ water before use to decontaminate the vials of RNAses. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL of citrate buffer (pH 6) was loaded in another 3 cc syringe. Syringes containing RNA and the lipids were connected to a T mixer (PEEK™ 500 μm ID junction) using FEP tubing (fluorinated ethylene-propylene; all FEP tubing used had a 2 mm internal diameter and a 3 mm outer diameter; obtained from Idex Health Science). The outlet from the T mixer was also FEP tubing. The third syringe containing the citrate buffer was connected to a separate piece of tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 hour. Then the mixture was loaded in a 5 cc syringe, which was fitted to a piece of FEP tubing and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, liposomes were concentrated to 2 mL and dialyzed against 10-15 volumes of 1×PBS using a Tangential Flow Filtration (TFF) system before recovering the final product. The TFF system and hollow fiber filtration membranes were purchased from Spectrum Labs and were used according to the manufacturer's guidelines. Hollow fiber filtration membranes with a 100 kD pore size cutoff and 20 $cm^2$ surface area were used. For in vitro and in vivo experiments, formulations were diluted to the required RNA concentration with 1×PBS.

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1×TE buffer (from kit) before addition of the dye. Separately, liposomes were diluted 10× or 100× in 1×TE buffer containing 0.5% Triton X before addition of the dye (to disrupt the liposomes and thus to assay total RNA). Thereafter an equal amount of dye was added to each solution and then ~180 μL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

To obtain smaller liposomes the syringe/tube method was replaced by a method in which the lipid and RNA solutions are mixed in channels on a microfluidic chip. Fresh lipid stock solutions in ethanol were prepared. 37 mg of DlinDMA, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 226.7 μL of the stock was added to 1.773 mL ethanol to make a working lipid stock solution of 2 mL. A 4 mL working solution of RNA was also prepared from a stock solution of ~1 μg/μL in 100 mM citrate buffer (pH 6). Four 20 mL glass vials (with stir bars) were rinsed with RNase Away solution and washed with plenty of MilliQ water before use to decontaminate the vials of RNAses. Two of the vials were used for the RNA working solution (2 mL in each vial) and the others for collecting the lipid and RNA mixes. The working lipid and RNA solutions were heated at 37° C. for 10 min before being loaded into 3 cc luer-lok syringes. Syringes containing RNA and the lipids were connected to a Mitos Droplet junction Chip (a glass microfluidic device obtained from Syrris, Part no. 3000158) using PTFE tubing 0.03 inches ID×1/16 inch OD, (Syrris) using a 4-way edge connector. Two RNA streams and one lipid stream were driven by syringe pumps and the mixing of the ethanol and aqueous phase was done at the X junction (100 μm×105 μm) of the chip. The flow rate of all three streams was kept at 1.5 mL/min, hence the ratio of total aqueous to ethanolic flow rate was 2:1. The tube outlet was positioned to collect the mixtures in a 20 mL glass vial (while stirring). The stir bar was taken out and the ethanol/aqueous solution was allowed to equilibrate to room temperature for 1 hour. Then the mixture was loaded in a 5 cc syringe which was fitted to a piece of PTFE tubing 0.03 inches ID×1/16 inches OD and in another 5 cc syringe with equal length of PTFE tubing, an equal volume of 100 mM citrate buffer (pH 6) was loaded. The two syringes were driven at 3 mL/min flow rate using a syringe pump and the final mixture collected in a 20 mL glass vial (while stirring). Next, liposomes were concentrated to 2 mL and dialyzed against 10-15 volumes of 1×PBS using the TFF system before recovering the final product. Hollow fiber filtration membranes with a 100 kDa pore size cutoff and 20 cm² surface area were used. For in vitro and in vivo experiments, formulations were diluted to the required RNA concentration with 1×PBS. Whereas liposomes prepared using the syringe/tube method with 75 µg RNA had a Z-average diameter (Zav) of 148 nm and a polydispersity index (pdI) of 0.122, the chip mixing gave liposomes with a Zav of 97 nm and a pdI of 0.086. The proportion of encapsulated RNA decreased slightly from 90% to 87%.

Encapsulation in liposomes was shown to protect RNA from RNase digestion. Experiments used 3.8 mAU of RNase A per microgram of RNA, incubated for 30 minutes at room temperature. RNase was inactivated with Proteinase K at 55° C. for 10 minutes. A 1:1 v/v mixture of sample to 25:24:1 v/v/v, phenol:chloroform:isoamyl alcohol was then added to extract the RNA from the lipids into the aqueous phase. Samples were mixed by vortexing for a few seconds and then placed on a centrifuge for 15 minutes at 12k RPM. The aqueous phase (containing the RNA) was removed and used to analyze the RNA. Prior to loading (400 ng RNA per well) all the samples were incubated with formaldehyde loading dye, denatured for 10 minutes at 65° C. and cooled to room temperature. Ambion Millennium markers were used to approximate the molecular weight of the RNA construct. The gel was run at 90 V. The gel was stained using 0.1% SYBR gold according to the manufacturer's guidelines in water by rocking at room temperature for 1 hour. FIG. 1 shows that RNase completely digests RNA in the absence of encapsulation (lane 3). RNA is undetectable after encapsulation (lane 4), and no change is seen if these liposomes are treated with RNase (lane 4). After RNase-treated liposomes are subjected to phenol extraction, undigested RNA is seen (lane 6). Even after 1 week at 4° C. the RNA could be seen without any fragmentation (FIG. 4, arrow). Protein expression in vivo was unchanged after 6 weeks at 4° C. and one freeze-thaw cycle. Thus liposome-encapsulated RNA is stable.

To assess in vivo expression of the RNA a reporter enzyme (SEAP; secreted alkaline phosphatase) was encoded in the replicon, rather than an immunogen. Expression levels were measured in sera diluted 1:4 in 1×Phospha-Light dilution buffer using a chemiluminescent alkaline phosphate substrate. 8-10 week old BALB/c mice (5/group) were injected intramuscularly on day 0, 50 µl per leg with 0.1 µg or 1 µg RNA dose. The same vector was also administered without the liposomes (in RNase free 1×PBS) at 1 µg. Virion-packaged replicons were also tested. Virion-packaged replicons used herein (referred to as "VRPs") were obtained by the methods of reference 42, where the alphavirus replicon is derived from the mutant VEEV or a chimera derived from the genome of VEEV engineered to contain the 3' UTR of Sindbis virus and a Sindbis virus packaging signal (PS), packaged by co-electroporating them into BHK cells with defective helper RNAs encoding the Sindbis virus capsid and glycoprotein genes.

As shown in FIG. 5, encapsulation increased SEAP levels by about ½ log at the 1 µg dose, and at day 6 expression from a 0.1 µg encapsulated dose matched levels seen with 1 µg unencapsulated dose. By day 3 expression levels exceeded those achieved with VRPs (squares). Thus expressed increased when the RNA was formulated in the liposomes relative to the naked RNA control, even at a 10× lower dose. Expression was also higher relative to the VRP control, but the kinetics of expression were very different (see FIG. 5). Delivery of the RNA with electroporation resulted in increased expression relative to the naked RNA control, but these levels were lower than with liposomes.

Figure 10:
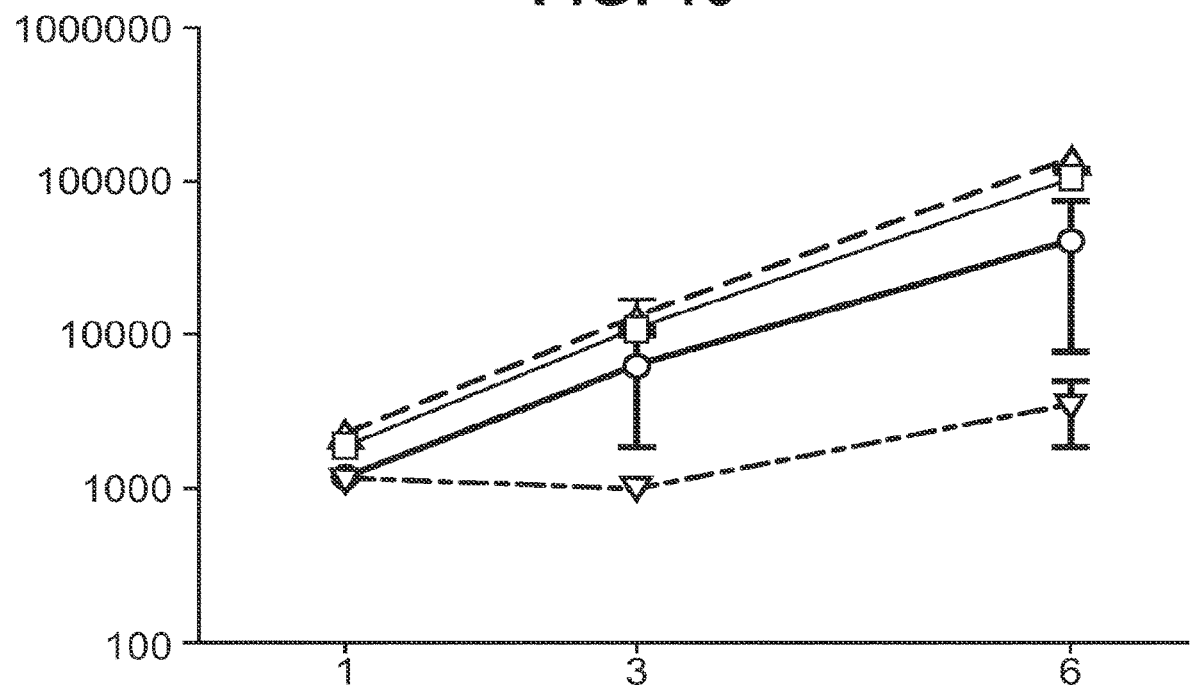
FIG. 10 shows expression levels after delivery of a replicon as naked RNA (circles), liposome-encapsulated RNA (triangle & square), or as a lipoplex (inverted triangle).

To assess whether the effect seen in the liposome groups was due merely to the liposome components, or was linked to the encapsulation, the replicon was administered in encapsulated form (with two different purification protocols, 0.1 µg RNA), or mixed with the liposomes after their formation (a non-encapsulated "lipoplex", 0.1 µg RNA), or as naked RNA (1 µg). FIG. 10 shows that the lipoplex gave the lowest levels of expression, showing that shows encapsulation is essential for potent expression.

Further SEAP experiments showed a clear dose response in vivo, with expression seen after delivery of as little as 1 ng RNA (FIG. 6). Further experiments comparing expression from encapsulated and naked replicons indicated that 0.01 µg encapsulated RNA was equivalent to 1 µg of naked RNA. At a 0.5 µg dose of RNA the encapsulated material gave a 12-fold higher expression at day 6; at a 0.1 µg dose levels were 24-fold higher at day 6.

Rather than looking at average levels in the group, individual animals were also studied. Whereas several animals were non-responders to naked replicons, encapsulation eliminated non-responders.

Further experiments replaced DlinDMA with DOTAP. Although the DOTAP liposomes gave better expression than naked replicon, they were inferior to the DlinDMA liposomes (2- to 3-fold difference at day 1).

Figure 7:
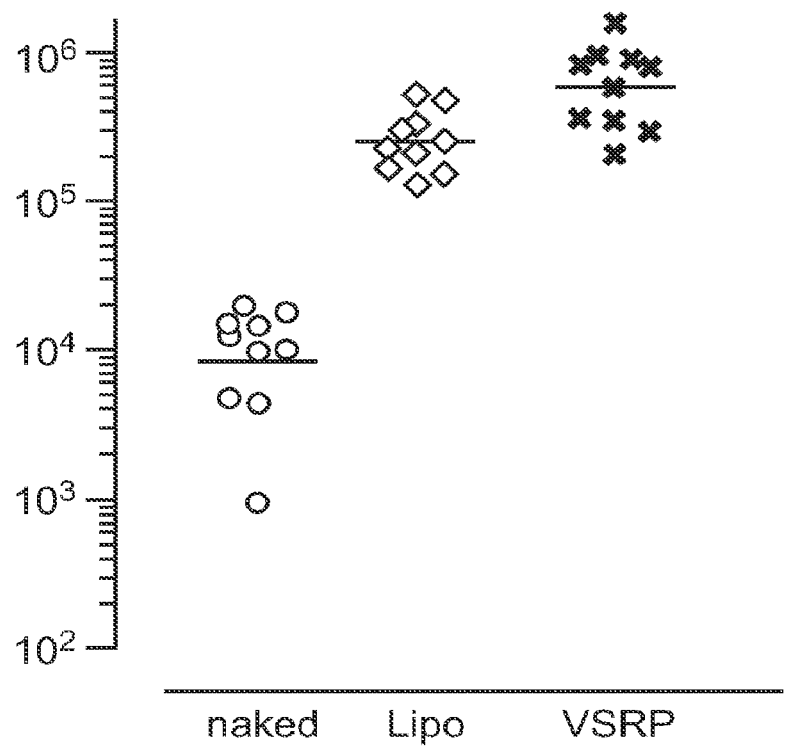
FIG. 7 shows anti-F IgG titers in animals receiving virion-packaged replicon (VRP or VSRP), 1 μg naked RNA, and 1 μg liposome-encapsulated RNA.
Figure 8:
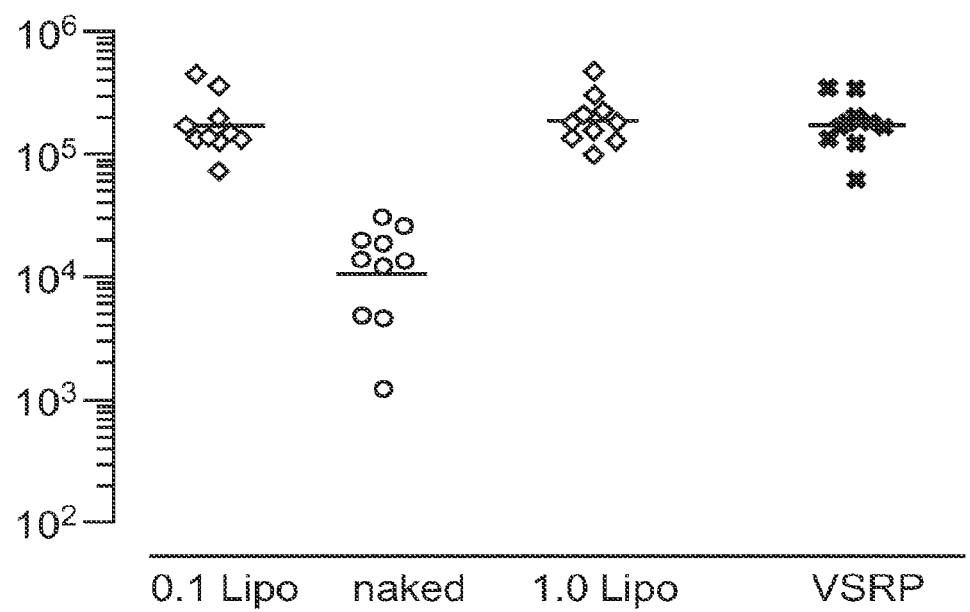
FIG. 8 shows anti-F IgG titers in animals receiving VRP, 1 μg naked RNA, and 0.1 g or 1 μg liposome-encapsulated RNA.
Figure 9:
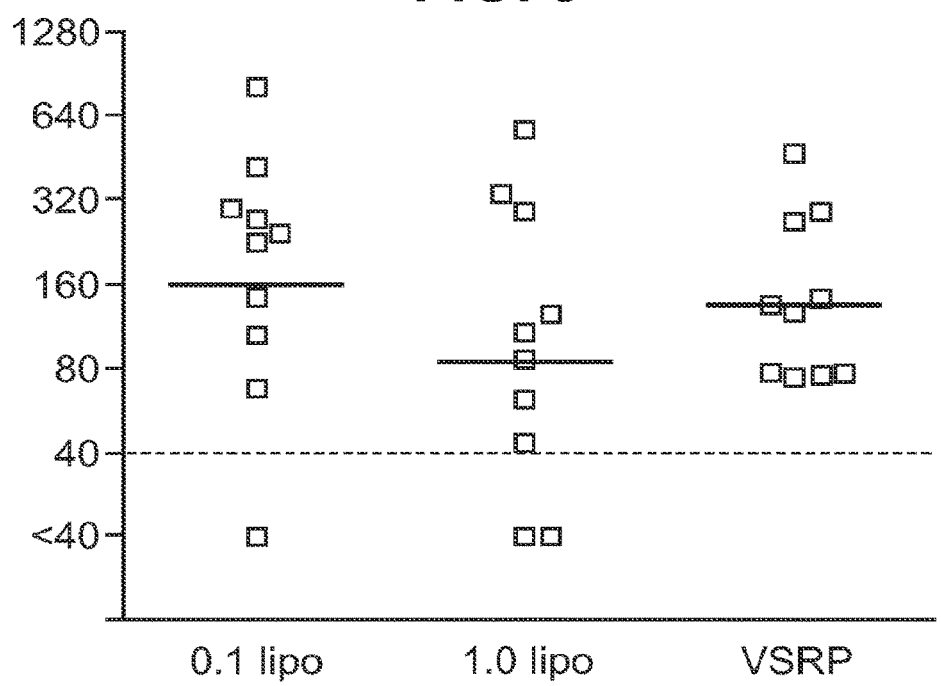
FIG. 9 shows neutralising antibody titers in animals receiving VRP or either 0.1 g or 1 μg liposome-encapsulated RNA.
Figure 12:
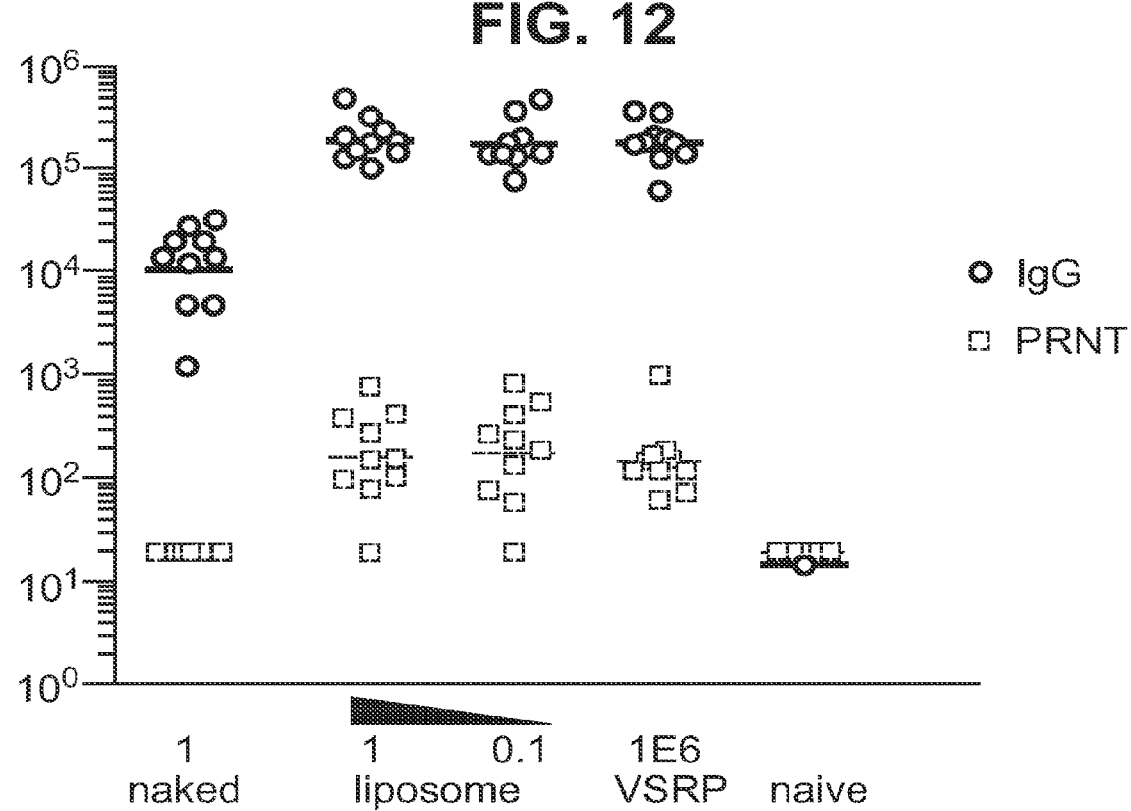
FIG. 12 shows F-specific IgG titers (circles) and PRNT titers (squares) after delivery of a replicon as naked RNA (1 μg), liposome-encapsulated RNA (0.1 or 1 μg), or packaged as a virion (VRP, $10^6$ IU). Titers in naïve mice are also shown. Solid lines show geometric means.

To assess in vivo immunogenicity a replicon was constructed to express full-length F protein from respiratory syncytial virus (RSV). This was delivered naked (1 µg), encapsulated in liposomes (0.1 or 1 µg), or packaged in virions (10⁶ IU; "VRP") at days 0 and 21. FIG. 7 shows anti-F IgG titers 2 weeks after the second dose, and the liposomes clearly enhance immunogenicity. FIG. 8 shows titers 2 weeks later, by which point there was no statistical difference between the encapsulated RNA at 0.1 µg, the encapsulated RNA at 1 µg, or the VRP group. Neutralisation titers (measured as 60% plaque reduction, "PRNT60") were not significantly different in these three groups 2 weeks after the second dose (FIG. 9). FIG. 12 shows both IgG and PRNT titers 4 weeks after the second dose.

Figure 13:
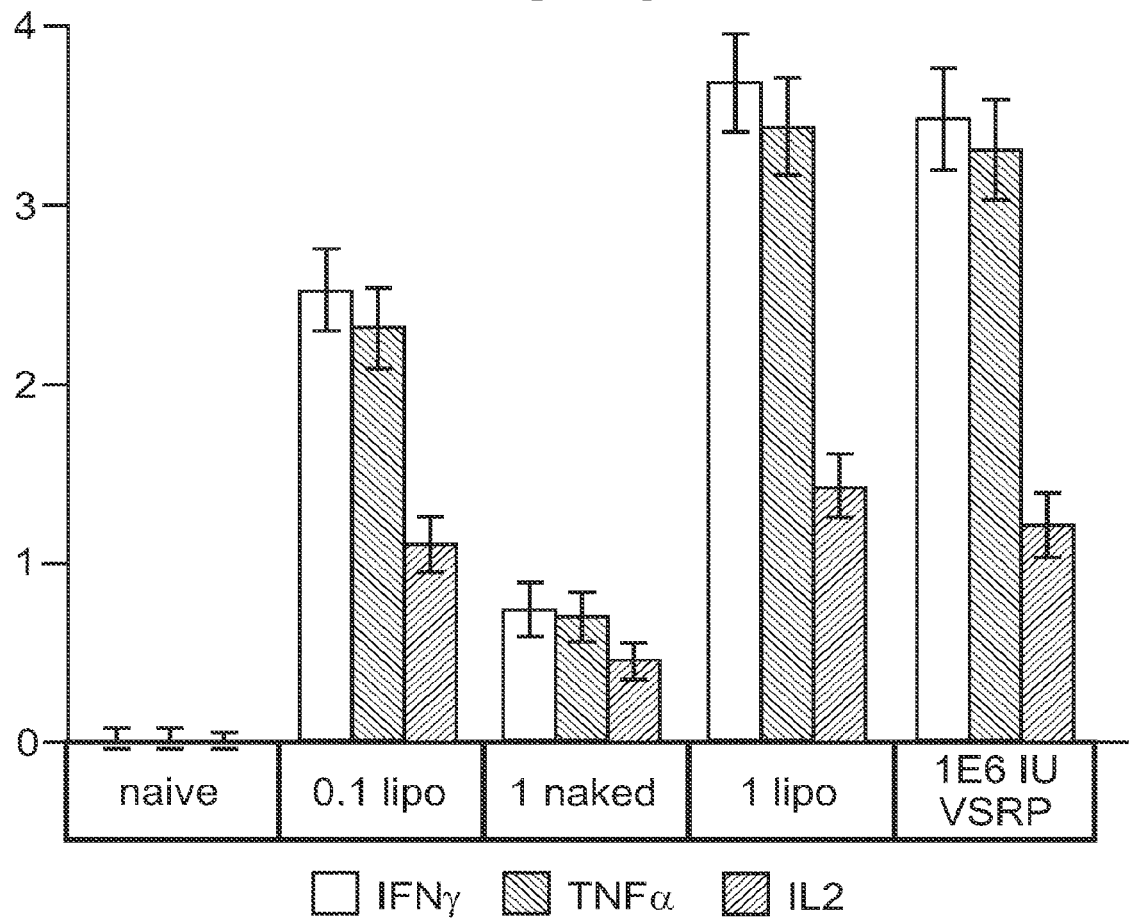
FIG. 13 shows intracellular cytokine production after restimulation with synthetic peptides representing the major epitopes in the F protein, 4 weeks after a second dose. The y-axis shows the % cytokine+ of CD8+CD4−.

FIG. 13 confirms that the RNA elicits a robust CD8 T cell response.

Further experiments compared F-specific IgG titers in mice receiving VRP, 0.1 µg liposome-encapsulated RNA, or 1 µg liposome-encapsulated RNA. Titer ratios (VRP: liposome) at various times after the second dose were as follows:

|  | 2 weeks | 4 weeks | 8 weeks |
| --- | --- | --- | --- |
| 0.1 µg | 2.9 | 1.0 | 1.1 |
| 1 µg | 2.3 | 0.9 | 0.9 |

Thus the liposome-encapsulated RNA induces essentially the same magnitude of immune response as seen with virion delivery.

Figure 11:
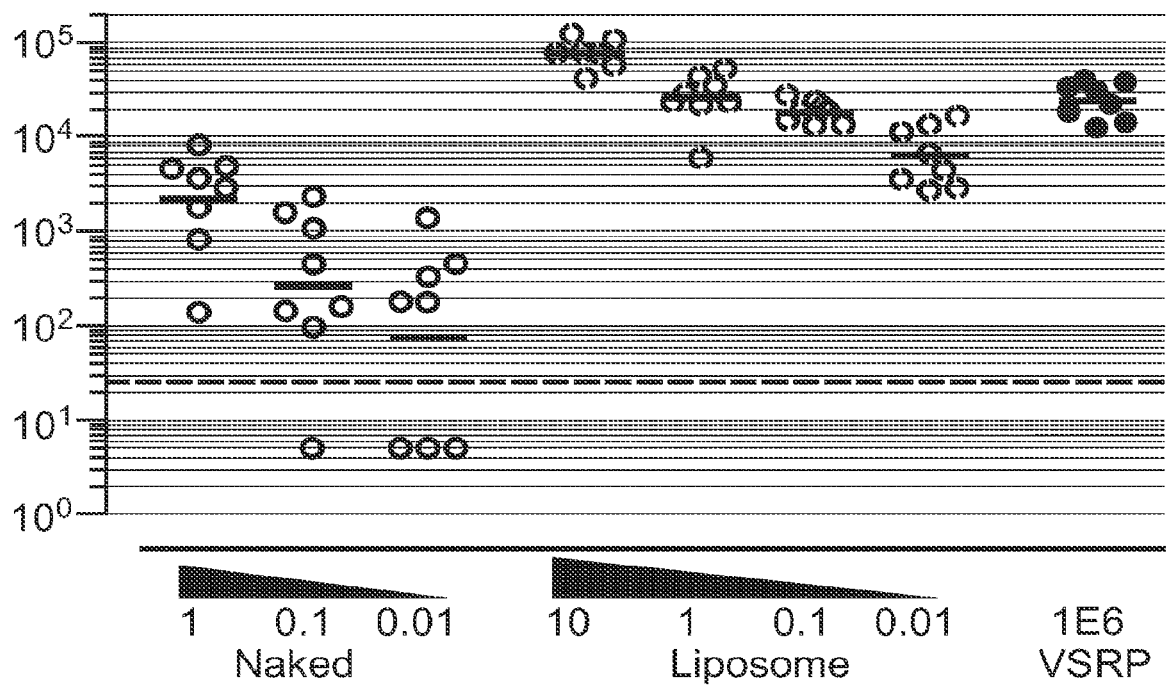
FIG. 11 shows F-specific IgG titers (2 weeks after second dose) after delivery of a replicon as naked RNA (0.01-1 μg), liposome-encapsulated RNA (0.01-10 μg), or packaged as a virion (VRP, $10^6$ infectious units or IU).

Further experiments showed superior F-specific IgG responses with a 10 μg dose, equivalent responses for 1 μg and 0.1 μg doses, and a lower response with a 0.01 μg dose. FIG. 11 shows IgG titers in mice receiving the replicon in naked form at 3 different doses, in liposomes at 4 different doses, or as VRP ($10^6$ IU). The response seen with 1 μg liposome-encapsulated RNA was statistically insignificant (ANOVA) when compared to VRP, but the higher response seen with 10 μg liposome-encapsulated RNA was statistically significant ($p<0.05$) when compared to both of these groups.

A further study confirmed that the 0.1 μg of liposome-encapsulated RNA gave much higher anti-F IgG responses (15 days post-second dose) than 0.1 μg of delivered DNA, and even was more immunogenic than 20 μg plasmid DNA encoding the F antigen, delivered by electroporation (Elgen™ DNA Delivery System, Inovio).

Liposome Manufacturing Methods

In general, eight different methods have been used for preparing liposomes according to the invention. These are referred to in the text as methods (A) to (H) and they differ mainly in relation to filtration and TFF steps. Details are as follows:

(A) Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 755 μL of the stock was added to 1.245 mL ethanol to make a working lipid stock solution of 2 mL. This amount of lipids was used to form liposomes with 250 μg RNA. A 2 mL working solution of RNA was also prepared from a stock solution of ~1 μg/μL in 100 mM citrate buffer (pH 6). Three 20 mL glass vials (with stir bars) were rinsed with RNase Away solution (Molecular BioProducts, San Diego, CA) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL of citrate buffer (pH 6) was loaded in another 3 cc syringe. Syringes containing RNA and the lipids were connected to a T mixer (PEEK™ 500 μm ID junction, Idex Health Science, Oak Harbor, WA) using FEP tubing (fluorinated ethylene-propylene; al FEP tubing has a 2 mm internal diameter×3 mm outer diameter, supplied by Idex Health Science). The outlet from the T mixer was also FEP tubing. The third syringe containing the citrate buffer was connected to a separate piece of FEP tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 hour. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation, AnnArbor, MI, USA). Before passing the liposomes, 4 mL of 1 M NaOH, 4 mL of 1 M NaCl and 10 mL of 100 mM citrate buffer (pH 6) were successively passed through the Mustang membrane. Liposomes were warmed for 10 min at 37° C. before passing through the membrane. Next, liposomes were concentrated to 2 mL and dialyzed against 10-15 volumes of 1×PBS using TFF before recovering the final product. The TFF system and hollow fiber filtration membranes were purchased from Spectrum Labs and were used according to the manufacturer's guidelines. Polysulfone hollow fiber filtration membranes (part number P/N: X1AB-100-20P) with a 100 kD pore size cutoff and 8 $cm^2$ surface area were used. For in vitro and in vivo experiments, formulations were diluted to the required RNA concentration with 1×PBS.

(B) As method (A) except that, after rocking, 226.7 μL of the stock was added to 1.773 mL ethanol to make a working lipid stock solution of 2 mL, thus modifying the lipid:RNA ratio.

(C) As method (B) except that the Mustang filtration was omitted, so liposomes went from the 20 mL glass vial into the TFF dialysis.

(D) As method (C) except that the TFF used polyethersulfone (PES) hollow fiber membranes (part number $P-C_{1-100}E-100-01N$) with a 100 kD pore size cutoff and 20 $cm^2$ surface area.

(E) As method (D) except that a Mustang membrane was used, as in method (A).

(F) As method (A) except that the Mustang filtration was omitted, so liposomes went from the 20 mL glass vial into the TFF dialysis.

(G) As method (D) except that a 4 mL working solution of RNA was prepared from a stock solution of ~1 μg/μL in 100 mM citrate buffer (pH 6). Then four 20 mL glass vials were prepared in the same way. Two of them were used for the RNA working solution (2 mL in each vial) and the others for collecting the lipid and RNA mixes, as in (C). Rather than use T mixer, syringes containing RNA and the lipids were connected to a Mitos Droplet junction Chip (a glass microfluidic device obtained from Syrris, Part no. 3000158) using PTFE tubing (0.03 inches internal diameter×1/16 inch outer diameter) using a 4-way edge connector (Syrris). Two RNA streams and one lipid stream were driven by syringe pumps and the mixing of the ethanol and aqueous phase was done at the X junction (100 μm×105 μm) of the chip. The flow rate of all three streams was kept at 1.5 mL/min, hence the ratio of total aqueous to ethanolic flow rate was 2:1. The tube outlet was positioned to collect the mixtures in a 20 mL glass vial (while stirring). The stir bar was taken out and the ethanol/aqueous solution was allowed to equilibrate to room temperature for 1 h. Then the mixture was loaded in a 5 cc syringe, which was fitted to another piece of the PTFE tubing; in another 5 cc syringe with equal length of PTFE tubing, an equal volume of 100 mM citrate buffer (pH 6) was loaded. The two syringes were driven at 3 mL/min flow rate using a syringe pump and the final mixture collected in a 20 mL glass vial (while stirring). Next, liposomes were concentrated to 2 mL and dialyzed against 10-15 volumes of 1×PBS using TFF, as in (D).

(H) As method (A) except that the 2 mL working lipid stock solution was made by mixing 120.9 µL of the lipid stock with 1.879 mL ethanol. Also, after mixing in the T mixer the liposomes from the 20 mL vial were loaded into Pierce Slide-A-Lyzer Dialysis Cassette (Thermo Scientific, extra strength, 0.5-3 mL capacity) and dialyzed against 400-500 mL of 1×PBS overnight at 4° C. in an autoclaved plastic container before recovering the final product.

RSV Immunogenicity

Figure 14:
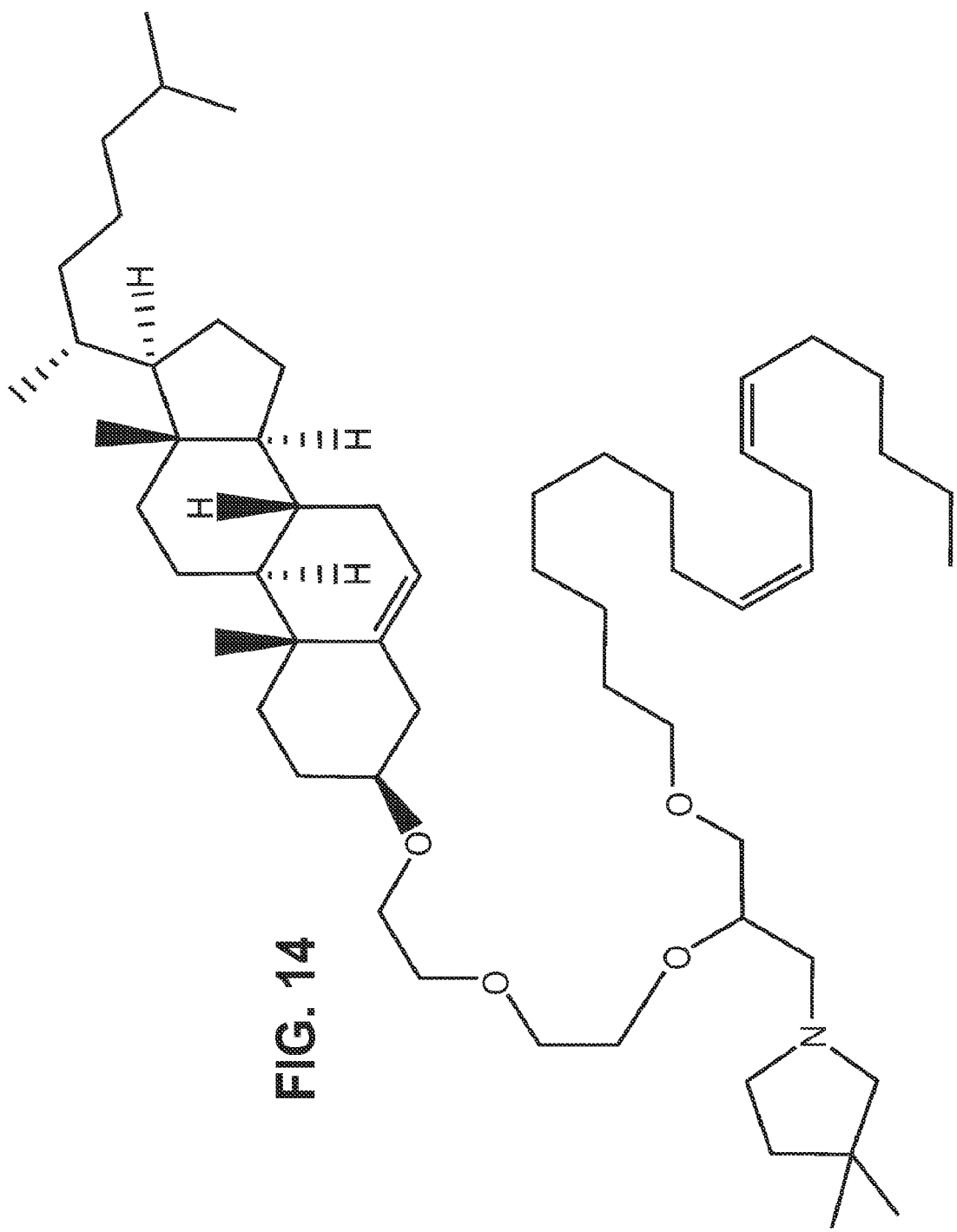
FIG. 14 shows the structure of lipid "RV05".

The vA317 self-replicating replicon encoding RSV F protein was administered to BALB/c mice, 4 or 8 animals per group, by bilateral intramuscular vaccinations (50 µL per leg) on days 0 and 21 with the replicon (1 µg) alone or formulated as liposomes with DlinDMA ("RV01") or DOTAP ("RV13") or the lipid shown in FIG. 14 ("RV05"). The RV01 liposomes had 40% DlinDMA, 10% DSPC, 48% cholesterol and 2% PEG-DMG, but with differing amounts of RNA. The RV05 liposomes had either 40% RV05, 10% DSPC, 48% cholesterol and 2% PEG-DMG or 60% RV05, 38% cholesterol and 2% PEG-DMG. The RV13 liposomes had 40% DOTAP, 10% DOPE, 48% cholesterol and 2% PEG-DMG. In all cases the PEG was PEG-2000 (i.e. 2 kDa PEG). For comparison, naked plasmid DNA (20 µg) expressing the same RSV-F antigen was delivered either using electroporation or with RV01(10) liposomes (0.1 µg DNA). Four mice were used as a naïve control group.

Liposomes were prepared by method (A) or method (B). For some liposomes made by method (A) a double or half amount of RNA was used. Z average particle diameter and polydispersity index were:

| RV | Zav (nm) | pdI | Preparation |
|---|---|---|---|
| RV01 (10) | 158.6 | 0.088 | (A) |
| RV01 (08) | 156.8 | 0.144 | (A) |
| RV01 (05) | 136.5 | 0.136 | (B) |
| RV01 (09) | 153.2 | 0.067 | (A) |
| RV01 (10) | 134.7 | 0.147 | (A) |
| RV05 (01) | 148 | 0.127 | (A) |
| RV05 (02) | 177.2 | 0.136 | (A) |
| RV13 (02) | 128.3 | 0.179 | (A) |

Serum was collected for antibody analysis on days 14, 36 and 49. Spleens were harvested from mice at day 49 for T cell analysis.

F-specific serum IgG titers (GMT) were as follows:

| RV | Day 14 | Day 36 |
|---|---|---|
| Naked DNA plasmid | 439 | 6712 |
| Naked A317 RNA | 78 | 2291 |
| RV01 (10) | 3020 | 26170 |
| RV01 (08) | 2326 | 9720 |
| RV01 (05) | 5352 | 54907 |
| RV01 (09) | 4428 | 51316 |
| RV05 (01) | 1356 | 5346 |
| RV05 (02) | 961 | 6915 |
| RV01 (10) DNA | 5 | 13 |
| RV13 (02) | 644 | 3616 |

The proportion of T cells which are cytokine-positive and specific for RSV F51-66 peptide are as follows, showing only figures which are statistically significantly above zero:

| RV | CD4+ CD8− | | | | CD4− CD8+ | | | |
|---|---|---|---|---|---|---|---|---|
| | IFNγ | IL2 | IL5 | TNFα | IFNγ | IL2 | IL5 | TNFα |
| Naked DNA plasmid | 0.04 | 0.07 | | 0.10 | 0.57 | 0.29 | | 0.66 |
| Naked A317 RNA | 0.04 | 0.05 | | 0.08 | 0.57 | 0.23 | | 0.67 |
| RV01 (10) | 0.07 | 0.10 | | 0.13 | 1.30 | 0.59 | | 1.32 |
| RV01 (08) | 0.02 | 0.04 | | 0.06 | 0.46 | 0.30 | | 0.51 |
| RV01 (05) | 0.08 | 0.12 | | 0.15 | 1.90 | 0.68 | | 1.94 |
| RV01 (09) | 0.06 | 0.08 | | 0.09 | 1.62 | 0.67 | | 1.71 |
| RV01 (10) DNA | | | | 0.03 | | | | 0.08 |
| RV13 (02) | 0.03 | 0.04 | | 0.06 | 1.15 | 0.41 | | 1.18 |

Thus the liposome formulations significantly enhanced immunogenicity relative to the naked RNA controls, as determined by increased F-specific IgG titers and T cell frequencies. Plasmid DNA formulated with liposomes, or delivered naked using electroporation, was significantly less immunogenic than liposome-formulated self-replicating RNA.

Further RV01 liposomes were prepared by method (H), again using 2 kDa PEG conjugated to DMG, and either encapsulating 150 µg RNA (vA375 replicon encoding surface fusion glycoprotein of RSV) or encapsulating only buffer. Thus these liposomes had 4000 DlinDMA, 10% DSPC, 48% Chol, and 2% PEG-DMG. Sizes and encapsulation were as follows:

| RV | Zav (nm) | pdI | RNA | Encapsulat" |
|---|---|---|---|---|
| RV01 (36) | 152.1 | 0.053 | + | 92.5% |
| RV01 (36) | 144 | 0.13 | − | − |

The liposomes were administered to BALB/c mice (10 per group) by bilateral intramuscular injection (50 µl per leg) on days 0 & 21. Doses were 0.01, 0.03, 0.1, 0.3 or 1 µg. F-specific serum IgG and PRNT60 titers (GMT) were as follows, 2 weeks after the first or second injection:

| RV | RNA (µg) | 2wp1 | 2wp2 | PRNT60 (2wp2) |
|---|---|---|---|---|
| Buffer control | 0 | − | − | 10 |
| RV01 (36) | 0 | − | − | 10 |
| RV01 (36) | 0.01 | 3399 | 50691 | 37 |
| RV01 (36) | 0.03 | 3446 | 53463 | 83 |
| RV01 (36) | 0.1 | 8262 | 76808 | 238 |
| RV01 (36) | 0.3 | 5913 | 82599 | 512 |
| RV01 (36) | 1 | 8213 | 85138 | 441 |

Cytomegalovirus Immunogenicity

RV01 liposomes with DLinDMA as the cationic lipid and 2 kDa PEG were used to deliver RNA replicons encoding CMV glycoproteins. The "vA160" replicon encodes full-length glycoproteins H and L (gH/gL), whereas the "vA322" replicon encodes a soluble form (gHsol/gL). The two proteins are under the control of separate subgenomic promoters in a single replicon; co-administration of two separate vectors, one encoding gH and one encoding gL, did not give good results.

BALB/c mice, 10 per group, were given bilateral intramuscular vaccinations (50 µL per leg) on days 0, 21 and 42 with VRPs expressing gH/gL (1×10$^6$ IU), VRPs expressing gHsol/gL (1×10$^6$ IU) and PBS as the controls. Two test groups received 1 µg of the vA160 or vA322 replicon formulated in liposomes (40% DlinDMA, 10% DSPC, 48% Chol, 2% PEG-DMG; made using method (D) but with 150 µg RNA batch size).

The vA160 liposomes had a Zav diameter of 168.8 nm, a pdI of 0.144, and 87.4% encapsulation. The vA322 liposomes had a Zav diameter of 162 nm, a pdI of 0.131, and 90% encapsulation.

The replicons were able to express two proteins from a single vector.

Sera were collected for immunological analysis on day 63 (3wp3). CMV neutralization titers (the reciprocal of the serum dilution producing a 50% reduction in number of positive virus foci per well, relative to controls) were as follows:

| gH/gL VRP | gHsol/gL VRP | gH/gL liposome | gHsol/gL liposome |
|---|---|---|---|
| 4576 | 2393 | 4240 | 10062 |

RNA expressing either a full-length or a soluble form of the CMV gH/gL complex thus elicited high titers of neutralizing antibodies, as assayed on epithelial cells. The average titers elicited by the liposome-encapsulated RNAs were at least as high as for the corresponding VRPs.

Repeat experiments confirmed that the replicon was able to express two proteins from a single vector. The RNA replicon gave a 3wp3 titer of 11457, compared to 5516 with VRPs.

Expression Kinetics

A self-replicating RNA replicon ("vA311") that expresses a luciferase reporter gene (luc) was used for studying the kinetics of protein expression after injection. BALB/c mice, 5 animals per group, received bilateral intramuscular vaccinations (50 μL per leg) on day 0 with:

Group 1 DNA expressing luciferase, delivered using electroporation (10 μg)
Group 2 self-replicating RNA (1 μg) formulated in liposomes (40% DlinDMA, 10% DSPC, 48% cholesterol, 2% PEG-2000 conjugated to DMG
Group 3 self-replicating RNA (1 μg) formulated with a cationic nanoemulsion (CNE17)
Group 4 self-replicating RNA (1 μg) formulated with a different cationic nanoemulsion
Group 5 VRP (1×10⁶ IU) expressing luciferase Prior to vaccination mice were depilated. Mice were anesthetized (2% isoflurane in oxygen), hair was first removed with an electric razor and then chemical Nair. Bioluminescence data was then acquired using a Xenogen IVIS 200 imaging system (Caliper Life Sciences) on days 3, 7, 14, 21, 28, 35, 42, 49, 63 and 70. Five minutes prior to imaging mice were injected intraperitoneally with 8 mg/kg of luciferin solution. Animals were then anesthetized and transferred to the imaging system. Image acquisition times were kept constant as bioluminescence signal was measured with a cooled CCD camera.

In visual terms, luciferase-expressing cells were seen to remain primarily at the site of RNA injection, and animals imaged after removal of quads showed no signal.

In quantitative terms, luciferase expression was measured as average radiance over a period of 70 days (p/s/cm²/sr), and results were as follows for the 5 groups:

| Days | 1 | 2 | 3 | 4 | 5 |
|---|---|---|---|---|---|
| 3 | 8.69E+07 | 3.33E+06 | 2.11E+06 | 9.71E+06 | 1.46E+07 |
| 7 | 1.04E+08 | 8.14E+06 | 1.83E+07 | 5.94E+07 | 1.64E+07 |
| 14 | 8.16E+07 | 2.91E+06 | 9.22E+06 | 3.48E+07 | 8.49E+05 |
| 21 | 1.27E+07 | 3.13E+05 | 6.79E+04 | 5.07E+05 | 6.79E+05 |
| 28 | 1.42E+07 | 6.37E+05 | 2.36E+04 | 4.06E+03 | 2.00E+03 |
| 35 | 1.21E+07 | 6.12E+05 | 2.08E+03 | | |
| 42 | 1.49E+07 | 8.70E+05 | | | |
| 49 | 1.17E+07 | 2.04E+05 | | | |
| 63 | 9.69E+06 | 1.72E+03 | | | |
| 70 | 9.29E+06 | | | | |

The self-replicating RNA formulated with cationic nanoemulsions showed measurable bioluminescence at day 3, which peaked at day 7 and then reduced to background levels by days 28 to 35. When formulated in liposomes the RNA showed measurable bioluminescence at day 3, which peaked at day 7 and reduced to background levels by day 63. RNA delivered using VRPs showed enhanced bioluminescence at day 21 when compared to the formulated RNA, but expression had reduced to background levels by day 28. Electroporated DNA showed the highest level of bioluminescence at all time points measured and levels of bioluminescence did not reduce to background levels within the 70 days of the experiment.

Delivery Volume

Hydrodynamic delivery employs the force generated by the rapid injection of a large volume of solution to overcome the physical barriers of cell membranes which prevent large and membrane-impermeable compounds from entering cells. This phenomenon has previously been shown to be useful for the intracellular delivery of DNA vaccines.

A typical mouse delivery volume for intramuscular injection is 50 μl into the hind leg, which is a relatively high volume for a mouse leg muscle. In contrast, a human intramuscular dose of ~0.5 ml is relatively small. If immunogenicity in mice would be volume-dependent then the replicon vaccines' efficacy might be due, at least in part, on hydrodynamic forces, which would not be encouraging for use of the same vaccines in humans and larger animals.

The vA317 replicon was delivered to BALB/c mice, 10 per group, by bilateral intramuscular vaccinations (5 or 50 per leg) on day 0 and 21:

Group 1 received naked replicon, 0.2 μg in 50 μL per leg
Group 2 received naked replicon, 0.2 μg in 5 μL per leg
Group 3 received emulsion-formulated replicon (0.2 μg, 50 μL per leg)
Group 4 received emulsion-formulated replicon (0.2 μg, 5 μL per leg)
Group 5 received liposome-formulated replicon (0.2 μg, 50 μL per leg)
Group 6 received liposome-formulated replicon (0.2 μg, 5 μL per leg)

The liposomes for groups 5 & 6 were 40% DlinDMA, 10% DSPC, 48% cholesterol, and 2% PEG-2000 conjugated to DMG.

Serum was collected for antibody analysis on days 14 and 35. F-specific serum IgG GMTs were:

| Day | 1 | 2 | 3 | 4 | 5 | 6 |
|---|---|---|---|---|---|---|
| 14 | 42 | 21 | 783 | 760 | 2669 | 2610 |
| 35 | 241 | 154 | 2316 | 2951 | 17655 | 18516 |

Thus immunogenicity of the formulated replicon did not vary according to the delivered volume, thus indicating that these RNA vaccines do not rely on hydrodynamic delivery for their efficacy.

Cotton Rats

A study was performed in cotton rats (*Sigmodon hispidis*) instead of mice. At a 1 µg dose liposome encapsulation increased F-specific IgG titers by 8.3-fold compared to naked RNA and increased PRNT titers by 9.5-fold. The magnitude of the antibody response was equivalent to that induced by $5 \times 10^6$ IU VRP. Both naked and liposome-encapsulated RNA were able to protect the cotton rats from RSV challenge ($1 \times 10^5$ plaque forming units), reducing lung viral load by at least 3.5 logs. Encapsulation increased the reduction by about 2-fold.

Further work in cotton rats used four different replicons: vA317 expresses full-length RSV-F; vA318 expresses truncated (transmembrane and cytoplasmic tail removed) RSV-F; vA142 expresses RSV-F with its fusion peptide deleted; vA140 expresses the truncated RSV-F also without its peptide. Cotton rats, 4 to 8 animals per group, were given intramuscular vaccinations (100 µL in one leg) on days 0 and 21 with the four different replicons at two doses (1.0 and 0.1 µg) formulated in liposomes made using 2 kDa PEG-conjugated DMG by method (D), but with a 150 µg RNA batch size. Control groups received a RSV-F subunit protein vaccine (5 µg) adjuvanted with alum (8 animals/group), VRPs expressing full-length RSV-F ($1 \times 10^6$ IU, 8 animals/group), or naïve control (4 animals/group). Serum was collected for antibody analysis on days 0, 21 and 34.

F-specific serum IgG titers and RSV serum neutralizing antibody titers on day 21 and 34 were:

| Group | IgG, day 21 | IgG, day 34 | NT, day 21 | NT, day 34 |
|---|---|---|---|---|
| 1 µg vA317 | 915 | 2249 | 115 | 459 |
| 0.1 µg vA317 | 343 | 734 | 87 | 95 |
| 1 µg vA318 | 335 | 1861 | 50 | 277 |
| 0.1 µg vA318 | 129 | 926 | 66 | 239 |
| 1 µg vA142 | 778 | 4819 | 92 | 211 |
| 0.1 µg vA142 | 554 | 2549 | 78 | 141 |
| 1 µg vA140 | 182 | 919 | 96 | 194 |
| 0.1 µg vA140 | 61 | 332 | 29 | 72 |
| 5 µg F trimer subunit/alum | 13765 | 86506 | 930 | 4744 |
| $1 \times 10^6$ IU VRP-F full | 1877 | 19179 | 104 | 4528 |
| Naïve | 5 | 5 | 10 | 15 |

All four replicons evaluated in this study (vA317, vA318, vA 142, vA 140) were immunogenic in cotton rats when delivered by liposome, although serum neutralization titers were at least ten-fold lower than those induced by adjuvanted protein vaccines or by VRPs. The liposome/RNA vaccines elicited serum F-specific IgG and RSV neutralizing antibodies after the first vaccination, and a second vaccination boosted the response effectively. F-specific IgG titers after the second vaccination with 1 µg replicon were 2- to 3-fold higher than after the second vaccination with 0.1 µg replicon. The four replicons elicited comparable antibody titers, suggesting that full length and truncated RSV-F, each with or without the fusion peptide, are similarly immunogenic in cotton rats.

Further work in cotton rats again used the vA317, vA318 and vA 142 replicons. Cotton rats, 2-8 animals per group, were given intramuscular vaccinations (100 µL in one leg) on days 0 and 21 with the replicons (0.1 or 1 µg) encapsulated in RV01 liposomes (with PEG-2000) made by method (D) but with a 150 µg RNA batch size. Control groups received the RSV-F subunit protein vaccine (5 µg) adjuvanted with alum or VRPs expressing full-length RSV-F ($1 \times 10^6$ IU, 8 animals/group). All these animals received a third vaccination (day 56) with RSV-F subunit protein vaccine (5 µg) adjuvanted with alum. In addition there was a naïve control (4 animals/group). In addition, an extra group was given bilateral intramuscular vaccinations (50 µL per leg) on days 0 and 56 with 1 µg vA317 RNA in liposomes but did not receive a third vaccination with the subunit protein vaccine.

Serum was collected for antibody analysis on days 0, 21, 35, 56, 70, plus days 14, 28 & 42 for the extra group. F-specific serum IgG titers (GMT) were as follows:

| | Day 21 | Day 35 | Day 56 | Day 70 |
|---|---|---|---|---|
| 1 µg vA318 | 260 | 1027 | 332 | 14263 |
| 0.1 µg vA318 | 95 | 274 | 144 | 2017 |
| 1 µg vA142 | 483 | 1847 | 1124 | 11168 |
| 0.1 µg vA142 | 314 | 871 | 418 | 11023 |
| 1 µg vA317 | 841 | 4032 | 1452 | 13852 |
| $1 \times 10^6$ VRP (F-full) | 2075 | 3938 | 1596 | 14574 |
| 5 µg F trimer subunit/alum | 12685 | 54526 | 25846 | 48864 |
| Naïve | 5 | 5 | 5 | 5 |

Serum neutralisation titers were as follows (60% RSV neutralization titers for 2 pools of 3-4 animals per group, GMT of these 2 pools per group):

| | Day 21 | Day 35 | Day 56 | Day 70 |
|---|---|---|---|---|
| 1 µg vA318 | 58 | 134 | 111 | 6344 |
| 0.1 µg vA318 | 41 | 102 | 63 | 6647 |
| 1 µg vA142 | 77 | 340 | 202 | 5427 |
| 0.1 µg vA142 | 35 | 65 | 56 | 2223 |
| 1 µg vA317 | 19 | 290 | 200 | 4189 |
| $1 \times 10^6$ VRP (F-full) | 104 | 1539 | 558 | 2876 |
| 5 µg F trimer subunit/alum | 448 | 4457 | 1630 | 3631 |
| Naïve | 10 | 10 | 10 | |

Serum titers and neutralising titers for the extra group were as follows:

| Day | 14 | 21 | 28 | 35 | 42 | 56 | 70 |
|---|---|---|---|---|---|---|---|
| IgG | 397 | 561 | 535 | 501 | 405 | 295 | 3589 |
| NT | 52 | 82 | 90 | 106 | 80 | 101 | 1348 |

Thus the replicons are confirmed as immunogenic in cotton rats, eliciting serum F-specific IgG and RSV neutralizing antibodies after the first vaccination. A second vaccination boosted the responses effectively. F-specific IgG titers after the second vaccination with 1.0 µg replicon were 1.5 to 4-fold higher than after the second vaccination with 0.1 µg replicon.

The third vaccination (protein at day 56) did not boost titers in cotton rats previously vaccinated with F trimer subunit + alum, but it did provide a large boost to titers in cotton rats previously vaccinated with replicon. In most cases the RSV serum neutralization titers after two replicon vaccinations followed by protein boost were equal to or greater than titers induced by two or three sequential protein vaccinations.

This study also evaluated the kinetics of the antibody response to 1.0 µg vA317. F-specific serum IgG and RSV neutralization titers induced by a single vaccination reached their peak around day 21 and were maintained through at least day 56 (50-70% drop in F-specific IgG titer, little change in RSV neutralization titer). A homologous second vaccination was given to these animals on day 56, and boosted antibody titers to a level at least equal to that achieved when the second vaccination was administered on day 21.

Further experiments involved a viral challenge. The vA368 replicon encodes the full-length wild type surface fusion glycoprotein of RSV with the fusion peptide deleted, with expression driven by the EV71 IRES. Cotton rats, 7 per group, were given intramuscular vaccinations (100 μL per leg) on days 0 and 21 with vA368 in liposomes prepared by method (H), 175 μg RNA batch size, or with VRPs having the same replicon. The liposomes included 2 kDa PEG, conjugated to DMG. A control group received 5 μg alum-adjuvanted protein, and a naïve control group was also included.

All groups received an intranasal challenge (i.n.) with 1×10⁶ PFU RSV four weeks after the final immunization. Serum was collected for antibody analysis on days 0, 21, 35. Viral lung titers were measured 5 days post challenge. Results were as follows:

|  | Liposome | VRP | Protein | Naïve |
|---|---|---|---|---|
| F-specific Serum IgG titers (GMT) | | | | |
| Day 21 | 370 | 1017 | 28988 | 5 |
| Day 35 | 2636 | 2002 | 113843 | 5 |

-continued

|  | Liposome | VRP | Protein | Naïve |
|---|---|---|---|---|
| Neutralising titers (GMT) | | | | |
| Day 21 | 47 | 65 | 336 | 10 |
| Day 35 | 308 | 271 | 5188 | 10 |
| Lung viral load (pfu per gram of lung) | | | | |
| Day 54 | 422 | 225 | 124 | 694110 |

Thus the RNA vaccine reduced the lung viral load by over three logs, from approximately 10⁶ PFU/g in unvaccinated control cotton rats to less than 10¹ PFU/g in vaccinated cotton rats.

Large Mammal Study

A large-animal study was performed in cattle. Calves (4-6 weeks old, ~60-80 kg, 5 per group) were immunised with 66 μg of replicon vA317 encoding full-length RSV F protein at days 0, 21, 86 and 146. The replicons were formulated inside liposomes made by method (E) but with a 1.5 mg RNA batch size; they had 40% DlinDMA, 10% DSPC, 48% cholesterol, and 2% PEG-2000 conjugated to DMG. PBS alone was used as a negative control, and a licensed vaccine was used as a positive control ("Triangle 4" from Fort Dodge, containing killed virus). All calves received 15 μg F protein adjuvanted with the MF59 emulsion on day 146.

The RNA vaccines encoded human RSV F whereas the "Triangle 4" vaccine contains bovine RSV F, but the RSV F protein is highly conserved between BRSV and HRSV.

Calves received 2 ml of each experimental vaccine, administered intramuscularly as 2×1 ml on each side of the neck. In contrast, the "Triangle 4" vaccine was given as a single 2 ml dose in the neck.

Serum was collected for antibody analysis on days 0, 14, 21, 35, 42, 56, 63, 86, 100, 107, 114, 121, 128, 135, 146, 160, 167, 174, 181, 188, 195, and 202. If an individual animal had a titer below the limit of detection it was assigned a titer of 5.

Figure 15:
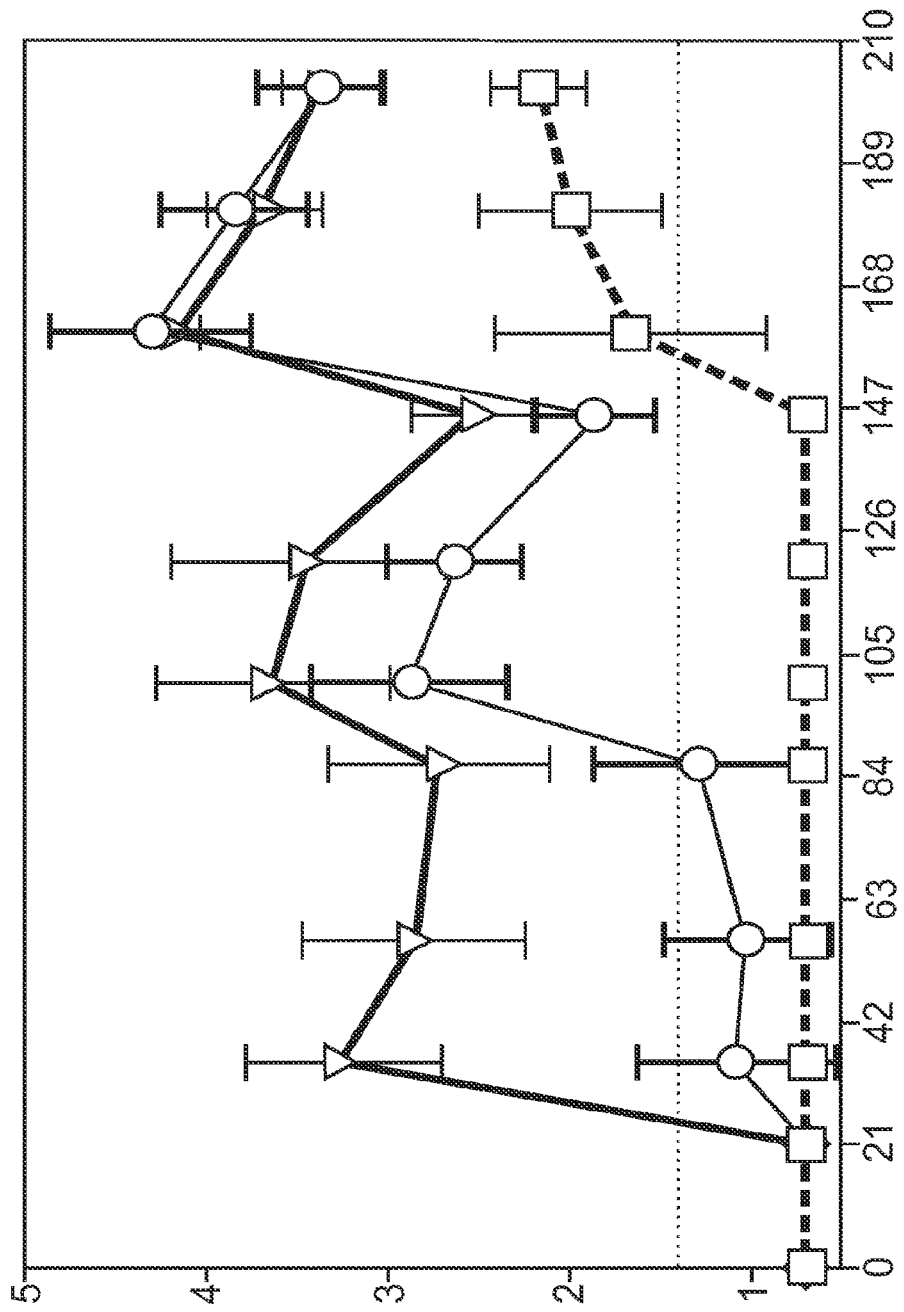
FIG. 15 shows F-specific IgG titers (mean $\log_{10}$ titers±std dev) over 210 days after immunisation of calves. The three lines are easily distinguished at day 63 and are, from bottom to top: PBS negative control; liposome-delivered RNA; and the "Triangle 4" product.

FIG. 15 shows F-specific IgG titers over 210 days. Over the first 63 days the RNA replicon was immunogenic in the cows via liposomes, although it gave lower titers than the licensed vaccine. All vaccinated cows showed F-specific antibodies after the second dose, and titers were very stable from the period of 2 to 6 weeks after the second dose (and were particularly stable for the RNA vaccines). Titres up to day 202 were as follows:

|  | D0 | 3wp1 D21 | 2wp2 D35 | 5wp2 D56 | ~9wp2 D86 | 2wp3 D100 | 5wp3 D121 | 8wp3 D146 | 2wp4 D160 | 5wp4 D181 | 8wp4 D202 |
|---|---|---|---|---|---|---|---|---|---|---|---|
| PBS | 5 | 5 | 5 | 5 | 5 | 5 | 5 | 5 | 46 | 98 | 150 |
| Liposome | 5 | 5 | 12 | 11 | 20 | 768 | 428 | 74 | 20774 | 7022 | 2353 |
| Triangle 4 | 5 | 5 | 1784 | 721 | 514 | 3406 | 2786 | 336 | 13376 | 4775 | 2133 |

RSV serum neutralizing antibody titers were as follows:

|  | D0 | 2wp2 D35 | 5wp2 D56 | 2wp3 D100 | 3wp3 D107 | 4wp3 D114 | 8wp3 D146 | 2wp4 D160 | 3wp4 D167 | 4wp4 D174 |
|---|---|---|---|---|---|---|---|---|---|---|
| PBS | 12 | 10 | 10 | 14 | 18 | 20 | 14 | 10 | 10 | 10 |
| Liposome | 13 | 10 | 10 | 20 | 13 | 17 | 13 | 47 | 26 | 21 |
| Triangle 4 | 12 | 15 | 13 | 39 | 38 | 41 | 13 | 24 | 26 | 15 |

The material used for the second liposome dose was not freshly prepared, and the same lot of RNA showed a decrease in potency in a mouse immunogenicity study. Therefore it is possible that the vaccine would have been more immunogenic if fresh material had been used for all vaccinations.

When assayed with complement, neutralizing antibodies were detected in all vaccinated cows. In this assay, all vaccinated calves had good neutralizing antibody titers after the second RNA vaccination Furthermore, the RNA vaccine elicited F-specific serum IgG titers that were detected in a few calves after the second vaccination and in all calves after the third.

MF59-adjuvanted RSV-F was able to boost the IgG response in all previously vaccinated calves, and to boost complement-independent neutralization titers of calves previously vaccinated with RNA.

Proof of concept for RNA vaccines in large animals is particularly important in light of the loss in potency observed previously with DNA-based vaccines when moving from small animal models to larger animals and humans. A typical dose for a cow DNA vaccine would be 0.5-1 mg [43, 44] and so it is very encouraging that immune responses were induced with only 66 μg of RNA.

Effect of PEG Length

As mentioned above, liposomes were prepared using DMG to which five different PEGs were conjugated. The average molecular weight of the PEG was 500 Da, 750 Da, 1 kDa, 2 kDa or 3 kDa.

Liposomes formed using the shortest PEGs (500 Da and 750 Da) were unstable or aggregated during TFF purification. PEG-750 gave liposomes with a significantly higher Zaverage diameter (669 nm) and polydispersity index (0.21), with 77% encapsulation. The PEG-500 liposomes visibly aggregated in solution during the TFF process and the experiment was terminated. Thus these short PEG liposomes were unstable, but the longer PEGs formed stable liposomes.

The different PEG lengths (FIG. 16) had a small effect on liposome diameter and polydispersity index. The Z-average diameter was 197 nm (0.119 pdI) for the 1 kDa PEG, 142 nm (0.137 pdI) for the 2 kDa PEG, and 147 nm (0.075 pdI) for the 3 kDa PEG. RNA encapsulation increased gradually as the PEG length increased, from 81.7% to 85.9% to 91.5% (although this relationship was not always seen in subsequent experiments).

The liposomes were administered to mice by intramuscular injection on day 0. Serum SEAP levels were measured at days 1, 3 and 6 by chemiluminescent assay. As shown in FIG. 3, the three PEG lengths were all effective, but varying the length of the PEG had some effect on serum SEAP levels, with PEG 2000 giving the highest expression.

Different Lipids and PEG Lengths

The vA317 replicon was administered in liposomes having a variety of different lipids with different PEG lengths. The liposomes all had 40% DlinDMA, 10% DSPC and 48% cholesterol, but the remaining 2% was varied, with different PEGylated lipids (e.g. FIGS. 17A to 17E) and different PEG lengths.

Figure 17A:
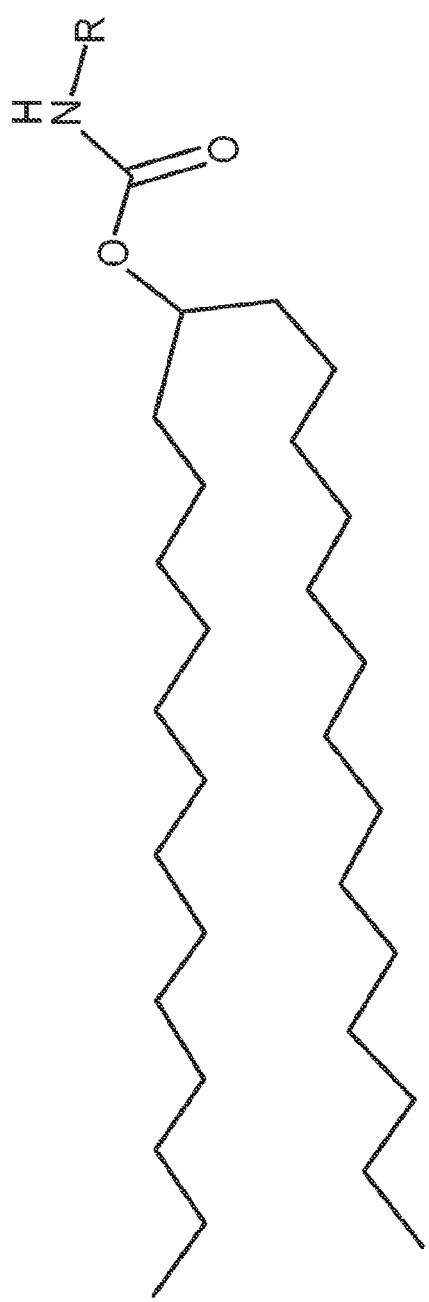
FIGS. 17A to 17E show structures of various PEG-conjugated lipids, where R is PEG of a desired length.
Figure 17B:
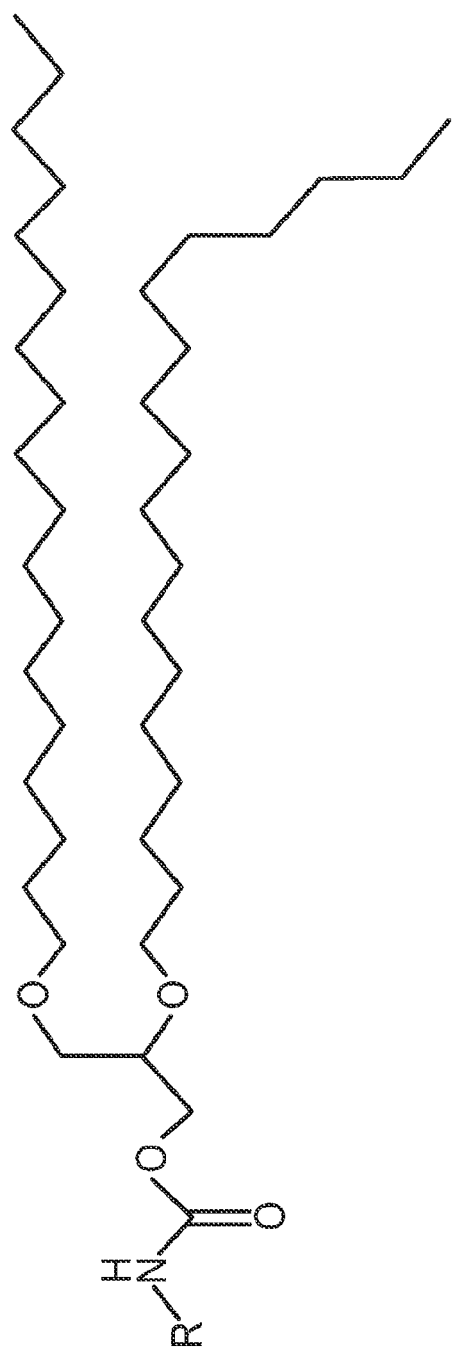
Figure 17C:
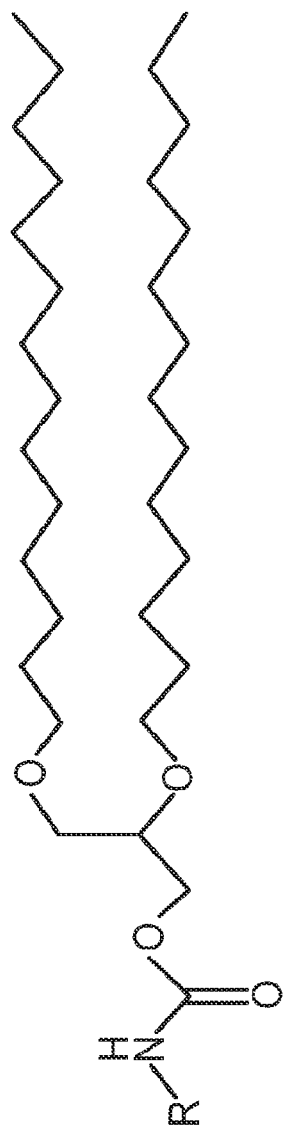
Figure 17D:
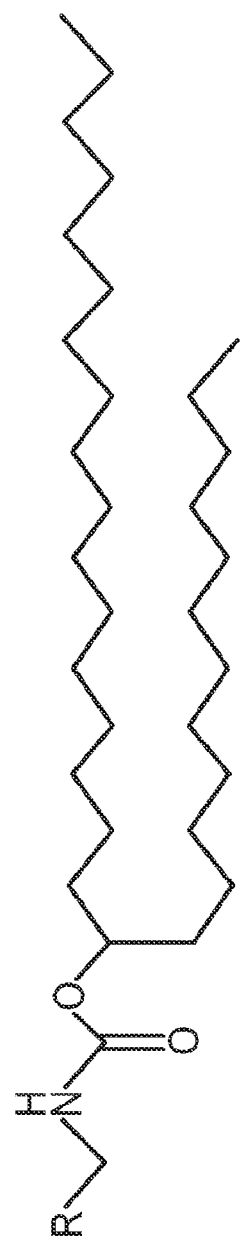
Figure 17E:
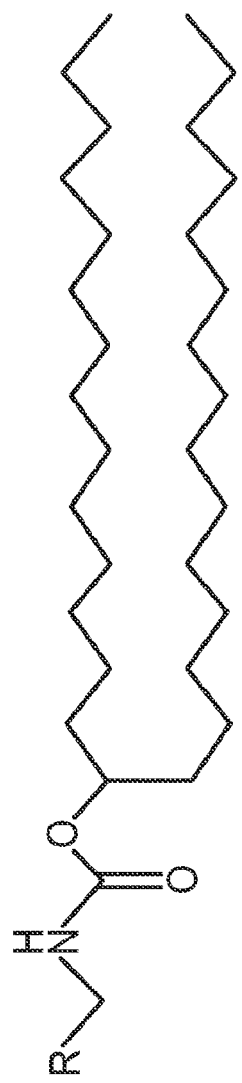

Physical characteristics of the liposomes, made by method (H), were:

| Name | PEGylated lipid | PEG length | Zav (nm) | pdI | % encapsulat" |
|---|---|---|---|---|---|
| A | DMG | 2000 | 136.3 | 0.087 | 85.35 |
| B | DMG | 3000 | 120.9 | 0.087 | 72.06 |
| C | DMG | 1000 | 175.9 | 0.111 | 92.52 |
| D | FIG. 17A | 2000 | 157.9 | 0.094 | 97.44 |
| E | FIG. 17D | 2000 | 122.2 | 0.122 | 77.84 |
| F | FIG. 17E | 2000 | 129.8 | 0.125 | 82.57 |
| G | Cholesterol | 2000 | 122.9 | 0.087 | 87.1 |
| H | FIG. 17C | 2000 | 138 | 0.137 | 78.48 |
| I | FIG. 17B | 2000 | 113.4 | 0.091 | 89.12 |

BALB/c mice, 8 per group, were given bilateral intramuscular vaccinations (50 μL per leg) on days 0 and 21 with the replicon, either naked (1 μg) or encapsulated in these liposomes (0.1 μg). Serum was collected for antibody analysis on days 14, and 35.

F-specific serum IgG titers (GMT) were as follows, 2 weeks after the two injections (2wp1):

| RV | 2wp1 | 2wp2 |
|---|---|---|
| Naked RNA | 216 | 1356 |
| A | 3271 | 15659 |
| B | 3860 | 22378 |
| C | 1691 | 7412 |
| D | 1025 | 1767 |
| E | 1618 | 9536 |
| F | 2684 | 11221 |
| G | 3514 | 10566 |
| H | 4142 | 22810 |
| I | 952 | 10410 |

The results show a trend, indicating that higher molecular weight PEG head groups are more immunogenic. As the length of DMG-conjugated PEG increases from 1000 Da to 3000 Da the 2wp2 F-specific IgG titers increase from 7412 to 15659 to 22378.

Changing the linker region from ester to ether did not impact the titers substantially. Also, at the same molecular weight of the head group (2000) there was a trend that increasing the length of the lipid tails lowers the titers (H with C14 dialkyl vs. I with C18 dialkyl). Replacing a PEG di-alkyl lipid tail with cholesterol had little impact on immunogenicity (A with DMG vs. G with cholesterol).

Figure 18:
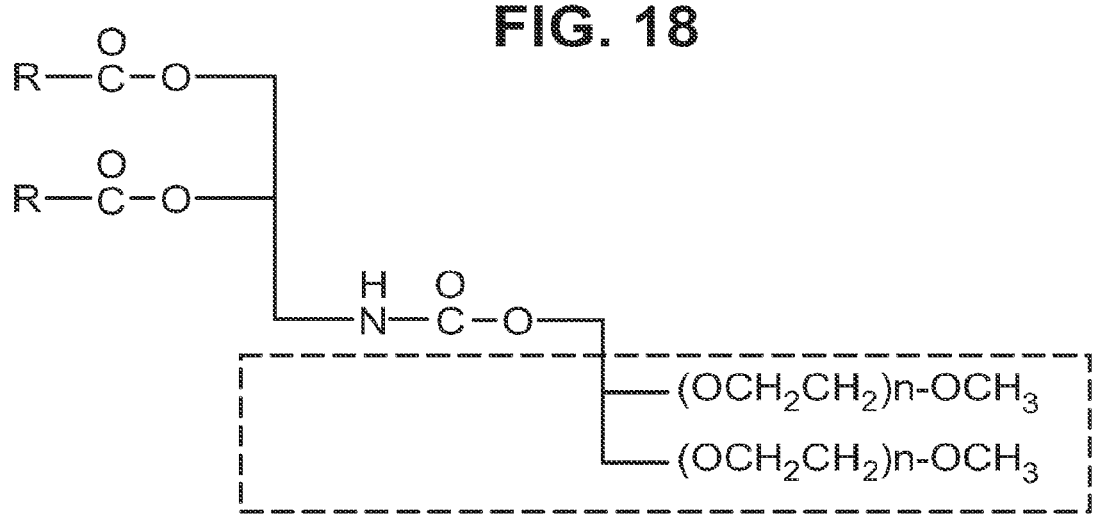
FIG. 18 shows the structure of a useful "split" PEG-conjugated lipid. The box shows the total MW of PEG in the lipid (which, in the specific example below, was 2000).

Similar experiments were performed with different lipids in which the 2 kDa of PEG is split into 2×1 kDa groups (FIG. 18, with total MW in the boxed region being 2000). The vA317 replicon was again used, with BALB/c mice, 8 per group, given bilateral intramuscular vaccinations (50 μL per leg) on days 0 & 21 with 1 μg naked RNA or 0.1 μg liposome-encapsulated RNA. The liposomes all had 40% cationic lipid (DlinDMA), 10% DSPC and 48% cholesterol, but the remaining 2% was varied, with different PEGylated lipids (but all with 2 kDa PEG). They were made by method (H).

Physical characteristics of the liposomes were:

| Name | PEGylated lipid | Zav (nm) | pdI | % encapsul" |
|---|---|---|---|---|
| A | DMG | 121 | 0.101 | 84.84 |
| B | Split; R = C14 saturated | 141.3 | 0.049 | 95.41 |
| C | Split; R = C16 saturated | 114.6 | 0.101 | 96.79 |
| D | Split; R = C18 saturated | 116.5 | 0.088 | 98.63 |
| E | Split; R = C18, 1 unsaturated | 129.4 | 0.149 | 93.37 |

Further liposomes were made with RV05. The liposomes had 40% cationic lipid (RV05) and 2% PEGylated DMG (2 kDa PEG), while the remaining components varied (but cholesterol was always included). The liposomes were made by method (H) but with pH 5. Physical characteristics were:

| Name | Other components | Zav (nm) | pdI | % encapsul" |
|---|---|---|---|---|
| F | 10% DSPC, 48% chol | 102.2 | 0.12 | 76.81 |
| G | 10% DSPC, 46% chol, 2% αGC | 103.7 | 0.107 | 72.58 |
| H | 10% DPyPE, 48% chol | 99.6 | 0.115 | 78.34 |
| I | 10% 18:3 PC, 48% chol | 130 | 0.14 | 87.92 |
| J | 10% 18:2 PC, 48% chol | 101.1 | 0.133 | 76.64 |
| K | 30% 18:2 PC, 28% chol | 134.3 | 0.158 | 57.76 |

αGC = α-galactosylceramide

BALB/c mice, 8 per group, were given bilateral intramuscular vaccinations (50 μL per leg) on days 0 and 21 with the replicon, either naked (1 μg) or encapsulated (0.1 μg). Serum was collected for antibody analysis on days 14, and 35. F-specific serum IgG titers (GMT) were as follows, 2 weeks after the two injections (2wp1):

|     | RV        | 2wp1 | 2wp2  |
| --- | --------- | ---- | ----- |
|     | Naked RNA | 321  | 915   |
|     | A         | 2761 | 17040 |
|     | B         | 866  | 3657  |
|     | C         | 1734 | 5209  |
|     | D         | 426  | 2079  |
|     | E         | 2696 | 15794 |
|     | F         | 551  | 955   |
|     | G         | 342  | 2531  |
|     | H         | 1127 | 3881  |
|     | I         | 364  | 1741  |
|     | J         | 567  | 5679  |
|     | K         | 1251 | 5303  |

Splitting the PEG head groups thus lowered in vivo titers. Including a double bond (1 degree of instauration per alkyl tail) in the PEG lipid tails increased IgG titers, 6 fold at day 14 and 7 fold at day 35. For a cationic lipid with an asymmetrical lipid tails (alkyl + cholesterol), changing the neutral lipid from DSPC (saturated C18 lipid tail) to 18:2 or 18:3 PC (with 2 and 3 unsaturated double bonds per tail) increased total IgG titers. Comparable results were observed with replacement of DSPC with DPyPE.

It will be understood that the invention has been described by way of example only and modifications may be made whilst remaining within the scope and spirit of the invention.

TABLE 1

| | useful phospholipids |
| --- | --- |
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidy1-rac-(1-glycerol . . . ) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol . . . ) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol . . . ) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol . . . ) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(1-glycerol . . . ) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |
| DSPG | 1,2-Distearoyl-sn-Glycero-3[Phosphatidyl-rac-(1-glycerol . . . ) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero-3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(1-glycerol) . . . ] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

REFERENCES

[1] Johanning et al. (1995) *Nucleic Acids Res* 23: 1495-1501.
[2] Heyes et al. (2005) *J Controlled Release* 107:276-87.
[3] WO2005/121348.
[4] *Liposomes: Methods and Protocols, Volume 1: Pharmaceutical Nanocarriers: Methods and Protocols.* (ed. Weissig). Humana Press, 2009. ISBN 160327359X.
[5] *Liposome Technology*, volumes I, II & III. (ed. Gregoriadis). Informa Healthcare, 2006.
[6] *Functional Polymer Colloids and Microparticles volume 4 (Microspheres, microcapsules & liposomes)*. (eds. Arshady & Guyot). Citus Books, 2002.
[7] Jeffs et al. (2005) *Pharmaceutical Research* 22 (3):362-372.
[8] WO2005/113782.
[9] WO2011/005799.
[10] El Ouahabi et al. (1996) *FEBS Letts* 380:108-12.
[11] Giuliani et al. (2006) *Proc Natl Acad Sci USA* 103(29): 10834-9.
[12] WO2009/016515.
[13] WO02/34771.
[14] WO2005/032582.
[15] WO2010/119343.
[16] WO2006/110413.
[17] WO2005/111066.
[18] WO2005/002619.
[19] WO2006/138004.
[20] WO2009/109860.
[21] WO02/02606.
[22] WO03/018054.
[23] WO2006/091517.
[24] WO2008/020330.
[25] WO2006/089264.
[26] WO2009/104092.
[27] WO2009/031043.
[28] WO2007/049155.
[29] Gennaro (2000) *Remington: The Science and Practice of Pharmacy.* 20th edition, ISBN: 0683306472.
[30] Romberg et al. (2008) *Pharmaceutical Research* 25:55-71.
[31] Hoekstra et al., Biochimica et Biophysica Acta 1660 (2004) 41-52
[32] WO2009/086558
[33] *Methods In Enzymology* (S. Colowick and N. Kaplan, eds., Academic Press, Inc.)
[34] *Handbook of Experimental Immunology*, Vols. I-IV (D. M. Weir and C. C. Blackwell, eds, 1986, Blackwell Scientific Publications)
[35] Sambrook et al. (2001) *Molecular Cloning: A Laboratory Manual*, 3rd edition (Cold Spring Harbor Laboratory Press).
[36] *Handbook of Surface and Colloidal Chemistry* (Birdi, K. S. ed., CRC Press, 1997)
[37] Ausubel et al. (eds) (2002) *Short protocols in molecular biology*, 5th edition (Current Protocols).
[38] *Molecular Biology Techniques: An Intensive Laboratory Course*, (Ream et al., eds., 1998, Academic Press)
[39] PCR (*Introduction to Biotechniques Series*), 2nd ed. (Newton & Graham eds., 1997, Springer Verlag)
[40] Yoneyama & Fujita (2007) *Cytokine & Growth Factor Reviews* 18:545-51.
[41] Maurer et al. (2001) *Biophysical Journal*, 80: 2310-2326.
[42] Perri et al. (2003) *J Virol* 77:10394-10403.
[43] Boxus et al. (2007) *J Virol* 81:6879-89.
[44] Taylor et al. (2005) *Vaccine* 23:1242-50.

The invention claimed is:

1. A method for raising a protective immune response in a vertebrate, the method comprising administering to the vertebrate an effective amount of a liposome within which at least one ribonucleic acid (RNA) that encodes an immunogen of interest is encapsulated, wherein the immunogen of interest elicits in the vertebrate a protective immune response against a bacterium, a virus, a fungus, a parasite, or an allergen, wherein the liposome comprises at least one lipid that includes a polyethylene glycol (PEG) moiety, wherein the PEG moiety is present on at least the exterior of the liposome, wherein the average molecular mass of the PEG moiety is between 1 kDa and 3 kDa, wherein the at least one lipid that includes the PEG moiety is not a 1,2-dimyristoyl-sn-glycero-3-phosphoethanolamine-N-[methoxy (polyethylene glycol)].

2. The method of claim 1, wherein the liposome has a diameter in the range of 80-160 nm.

3. The method of claim 1, wherein the liposome further comprises a cationic lipid.

4. The method of claim 1, wherein the liposome further comprises a zwitterionic lipid.

5. The method of claim 1, wherein the at least one RNA that encodes the immunogen of the interest is a self-replicating RNA, which further encodes a RNA-dependent RNA polymerase that can transcribe RNA from the self-replicating RNA.

6. The method of claim 5, wherein the self-replicating RNA has two open reading frames, wherein the first open reading frame encodes an alphavirus replicase and the second open reading frame encodes the immunogen of interest, and wherein the alphavirus replicase comprises the RNA-dependent RNA polymerase.

7. The method of claim 1, wherein the immunogen of interest elicits a protective immune response in the vertebrate against the bacterium, the virus, the fungus, or the parasite.

8. A method for raising a protective immune response in a vertebrate, the method comprising administering to the vertebrate an effective amount of a liposome within which at least one RNA that encodes an immunogen of interest is encapsulated, wherein the immunogen of interest is expressed and elicits in the vertebrate a protective immune response against a bacterium, a virus, a fungus, a parasite, or an allergen, wherein the liposome comprises at least one lipid that includes a PEG moiety, wherein the PEG moiety is present on at least the exterior of the liposome, wherein the PEG moiety has a number-averaged degree of polymerization of ethylene oxide between 22 and 67, wherein the at least one lipid that includes the PEG moiety is not a 1,2-dimyristoyl-sn-glycero-3-phosphoethanolamine-N-[methoxy (polyethylene glycol)].

9. A method for raising a protective immune response in a vertebrate, the method comprising administering to the vertebrate an effective amount of a liposome within which at least one RNA that encodes an immunogen of interest is encapsulated, wherein the immunogen of interest is expressed and elicits in the vertebrate a protective immune response against a virus, wherein the liposome comprises at least one lipid that includes a PEG moiety, wherein the PEG moiety is present on at least the exterior of the liposome, wherein the PEG moiety has a number-averaged degree of polymerization of ethylene oxide between 22 and 67, wherein the at least one lipid that includes the PEG moiety is not a 1,2-dimyristoyl-sn-glycero-3-phosphoethanolamine-N-[methoxy (polyethylene glycol)].

10. The method of claim 8, wherein the liposome has a diameter in the range of 80-160 nm.

11. The method of claim 9, wherein the liposome has a diameter in the range of 80-160 nm.

12. The method of claim 8, wherein the liposome further comprises a cationic lipid.

13. The method of claim 9, wherein the liposome further comprises a cationic lipid.

14. The method of claim 8, wherein the liposome further comprises a zwitterionic lipid.

15. The method of claim 9, wherein the liposome further comprises a zwitterionic lipid.

16. The method of claim 8, wherein the at least one RNA that encodes the immunogen of the interest is a self-replicating RNA, which further encodes a RNA-dependent RNA polymerase that can transcribe RNA from the self-replicating RNA.

17. The method of claim 9, wherein the at least one RNA that encodes the immunogen of the interest is a self-replicating RNA, which further encodes a RNA-dependent RNA polymerase that can transcribe RNA from the self-replicating RNA.

18. The method of claim 16, wherein the self-replicating RNA has two open reading frames, wherein the first open reading frame encodes an alphavirus replicase and the second open reading frame encodes the immunogen of interest, and wherein the alphavirus replicase comprises the RNA-dependent RNA polymerase.

19. The method of claim 17, wherein the self-replicating RNA has two open reading frames, wherein the first open reading frame encodes an alphavirus replicase and the second open reading frame encodes the immunogen of interest, and wherein the alphavirus replicase comprises the RNA-dependent RNA polymerase.

20. The method of claim 4, wherein the zwitterionic lipid is 1,2-distearoyl-sn-glycero-3-phosphocholine (DSPC).

21. The method of claim 14, wherein the zwitterionic lipid is DSPC.

22. The method of claim 15, wherein the zwitterionic lipid is DSPC.

23. The method of claim 1, wherein the liposome further comprises cholesterol.

24. The method of claim 8, wherein the liposome further comprises cholesterol.

25. The method of claim 9, wherein the liposome further comprises cholesterol.

* * * * *